United States Patent
Harb et al.

(10) Patent No.: US 12,173,324 B2
(45) Date of Patent: *Dec. 24, 2024

(54) DIFFERENTIATION OF PANCREATIC ENDOCRINE CELLS

(71) Applicant: Vertex Pharmaceuticals Incorporated, Boston, MA (US)

(72) Inventors: George Harb, Boston, MA (US); Chunhui Xie, Belmont, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/988,257

(22) Filed: Nov. 16, 2022

(65) Prior Publication Data

US 2023/0092449 A1    Mar. 23, 2023

Related U.S. Application Data

(63) Continuation of application No. 17/390,839, filed on Jul. 30, 2021.

(60) Provisional application No. 63/059,433, filed on Jul. 31, 2020.

(51) Int. Cl.
*C12N 5/071* (2010.01)
*A61K 35/39* (2015.01)

(52) U.S. Cl.
CPC ............ *C12N 5/0676* (2013.01); *A61K 35/39* (2013.01); *C12N 2501/11* (2013.01); *C12N 2501/15* (2013.01); *C12N 2501/155* (2013.01); *C12N 2501/415* (2013.01)

(58) Field of Classification Search
CPC .............................. C12N 5/0676; A61K 35/39
See application file for complete search history.

(56) References Cited

U.S. PATENT DOCUMENTS

| | | | |
|---|---|---|---|
| 9,062,290 B2 | 6/2015 | Rezania | |
| 9,096,832 B2 | 8/2015 | Xu | |
| 9,585,917 B2 | 3/2017 | Martinson et al. | |
| 9,744,195 B2 | 8/2017 | Xu | |
| 10,030,229 B2 | 7/2018 | Peterson et al. | |
| 10,358,628 B2 | 7/2019 | Rezania | |
| 10,370,645 B2 | 8/2019 | D'Amour et al. | |
| 10,443,042 B2 | 10/2019 | Melton et al. | |
| 10,494,609 B2 | 12/2019 | Rezania | |
| 10,947,511 B2 | 3/2021 | Rezania | |
| 11,085,027 B2 | 8/2021 | Melton et al. | |
| 11,466,256 B2 | 10/2022 | Pagliuca et al. | |
| 11,525,120 B2 | 12/2022 | Pagliuca et al. | |
| 12,006,516 B2 | 6/2024 | Harb | |
| 12,049,645 B2 | 7/2024 | Harb | |
| 2007/0259421 A1 | 11/2007 | D'Amour et al. | |
| 2008/0267926 A1 | 10/2008 | Martinson et al. | |
| 2011/0008819 A1 | 1/2011 | Chipperfield et al. | |
| 2015/0240212 A1 | 8/2015 | Peterson et al. | |
| 2016/0177269 A1 | 6/2016 | Melton et al. | |
| 2016/0272944 A1 | 9/2016 | Ding et al. | |
| 2017/0009210 A1 | 1/2017 | Ikeda et al. | |
| 2017/0029778 A1 | 2/2017 | Peterson et al. | |
| 2020/0332262 A1 | 10/2020 | Poh et al. | |
| 2021/0017157 A1 | 1/2021 | Thiel et al. | |
| 2021/0198632 A1 | 7/2021 | Pagliuca et al. | |
| 2021/0214690 A1 | 7/2021 | Melton et al. | |
| 2021/0238553 A1 | 8/2021 | Pagliuca et al. | |
| 2021/0353686 A1 | 11/2021 | Ito et al. | |
| 2021/0403876 A1 | 12/2021 | Pagliuca et al. | |
| 2022/0090020 A1 | 3/2022 | Harb et al. | |
| 2022/0162562 A1 | 5/2022 | Peterson et al. | |
| 2022/0233646 A1 | 7/2022 | Carey | |
| 2023/0075375 A1 | 3/2023 | Pagliuca et al. | |

FOREIGN PATENT DOCUMENTS

| | | |
|---|---|---|
| JP | 2019/068849 | 5/2019 |
| WO | WO 2009/132083 A2 | 10/2009 |
| WO | WO 2010/002846 A1 | 1/2010 |
| WO | WO 2011/143299 A2 | 11/2011 |
| WO | 2017/177163 A1 | 10/2017 |
| WO | 2017/222879 A1 | 12/2017 |
| WO | WO 2019/018818 A1 | 1/2019 |
| WO | WO 2019/169351 A1 | 9/2019 |
| WO | WO 2019/183597 A1 | 9/2019 |
| WO | WO 2019/213366 A1 | 11/2019 |

(Continued)

OTHER PUBLICATIONS

Jensen et al. Independent development of pancreatic α- and β-cells from neurogenin3-expressing precursors: a role for the Notch pathway in repression of premature differentiation. Diabetes 2000, 49:163-176. (Year: 2000).*
Velazco-Cruz et al. Acquisition of dynamic function in human stem cell-derived β cells. Stem Cell Reports 2019, 12:351-365. (Year: 2019).*
Anlauf et al. Expression of the two isoforms of the vesicular monoamine transporter (VMAT1 and VMAT2) in the endocrine pancreas and pancreatic endocrine tumors. Journal of Histochemistry & Cytochemistry 2003, 51;8:1027-1040. (Year: 2003).*
Al-Masri et al., Effect of forkhead box O1 (FOXO1) on beta cell development in the human fetal pancreas. Diabetologia. Apr. 2010;53(4):699-711.
Apelqvist et al., Notch signalling controls pancreatic cell differentiation. Nature. Aug. 26, 1999;400(6747):877-81. doi: 10.1038/23716.

(Continued)

*Primary Examiner* — Allison M Fox
*Assistant Examiner* — Jennifer S Spence
(74) *Attorney, Agent, or Firm* — Klarquist Sparkman, LLP; Susan Alpert Siegel; Sheree Lynn Rybak

(57) ABSTRACT

Disclosed herein are compositions and methods related to differentiation of stem cells into pancreatic endocrine cells. In some aspects, the methods provided herein relate to generation of pancreatic β cell, α cell, δ cells, and EC cells in vitro. In some aspects, the disclosure provides pharmaceutical compositions including the cells generated according to the methods disclosed herein, as well as methods of treatment making use thereof.

21 Claims, 13 Drawing Sheets

(56) References Cited

FOREIGN PATENT DOCUMENTS

| WO | WO 2019/217487 A1 | 11/2019 |
|---|---|---|
| WO | WO 2019/222487 A1 | 11/2019 |
| WO | WO 2020/033879 A1 | 2/2020 |
| WO | WO 2020/264072 A1 | 12/2020 |
| WO | WO 2022/026932 A2 | 2/2022 |
| WO | WO 2022/026933 A2 | 2/2022 |
| WO | WO 2022/147056 A1 | 7/2022 |
| WO | WO 2022/192300 A1 | 9/2022 |

OTHER PUBLICATIONS

Balboa et al., Functional, metabolic and transcriptional maturation of human pancreatic islets derived from stem cells. Nat Biotechnol. Jul. 2022;40(7):1042-1055. doi: 10.1038/s41587-022-01219-z. Epub Mar. 3, 2022.
Bouchi et al., FOXO1 inhibition yields functional insulin-producing cells in human gut organoid cultures. Nat Commun. Jun. 30, 2014;5:4242. doi: 10.1038/ncomms5242. Author Manuscript, 24 pages.
Chen et al., A small molecule that directs differentiation of human ESCs into the pancreatic lineage. Nat Chem Biol. Apr. 2009;5(4):258-65. doi: 10.1038/nchembio.154. Epub Mar. 15, 2009.
D'Amour et al., Production of pancreatic hormone-expressing endocrine cells from human embryonic stem cells. Nat Biotechnol. Nov. 2006;24(11):1392-401. doi: 10.1038/nbt1259. Epub Oct. 19, 2006.
Hering et al., Phase 3 Trial of Transplantation of Human Islets in Type 1 Diabetes Complicated by Severe Hypoglycemia. Diabetes Care. Jul. 2016;39(7):1230-40. doi: 10.2337/dc15-1988. Epub Apr. 18, 2016.
Kimura et al., Small molecule AT7867 proliferates PDX1-expressing pancreatic progenitor cells derived from human pluripotent stem cells. Stem Cell Res. Oct. 2017;24:61-68.
Nagashima et al., Discovery of novel forkhead box O1 inhibitors for treating type 2 diabetes: improvement of fasting glycemia in diabetic db/db mice. Mol Pharmacol. Nov. 2010; 78(5):961-70. doi: 10.1124/mol.110.065714. Epub Aug. 24, 2010.
Sasaki et al., Transient FOXO1 inhibition in pancreatic endoderm promotes the generation of NGN3+ endocrine precursors from human iPSCs. Stem Cell Res. Apr. 2020;44:101754.
Segerstolpe et al., Single-Cell Transcriptome Profiling of Human Pancreatic Islets in Health and Type 2 Diabetes. Cell Metab. Oct. 11, 2016;24(4):593-607. doi: 10.1016/j.cmet.2016.08.020. Epub Sep. 22, 2016.
Sharon et al., Wnt Signaling Separates the Progenitor and Endocrine Compartments during Pancreas Development. Cell Rep. May 21, 2019;27(8):2281-2291.e5. doi: 10.1016/j.celrep.2019.04.083.
Talchai et al., Legacy Effect of Foxo1 in Pancreatic Endocrine Progenitors on Adult β-Cell Mass and Function. Diabetes. Aug. 2015;64(8):2868-79. doi: 10.2337/db14-1696. Epub Mar. 17, 2015.
Yu et al., FoxO1 inhibition promotes differentiation of human embryonic stem cells into insulin producing cells. Exp Cell Res. Jan. 1, 2018;362(1):227-234.
Peterson Q.P. et al., "A Method for the Generation of Human Stem Cell-Derived Alpha Cells", Nature Communications 11(2241):1-14 (2020).
Schweicher J. et al., "Membranes to Achieve Immunoprotection of Transplanted Islets", Front Biosci 29:49-76 (2014).
Street C.N. et al., "Islet Graft Assessment in the Edmonton Protocol", Diabetes 53:3107-3114 (2004).
Street C.N. et al., "Stem Cell-Based Approaches to Solving the Problem of Tissue Supply for Islet Transplantation In Type 1 Diabetes", The International Journal of Biochemistry & Cell Biology 36:667-683 (2004).
Co-pending U.S. Appl. No. 18/055,327, inventors Felicia J. Pagliuca et al., filed Nov. 14, 2022.
Co-pending U.S. Appl. No. 18/054,860, inventors Felicia Pagliuca et al., filed Nov. 11, 2022.
Co-pending U.S. Appl. No. 18/051,721, inventors George Harb et al., filed Nov. 1, 2022.
Co-pending U.S. Appl. No. 17/985,746, inventors Felicia J. Pagliuca et al., filed Nov. 11, 2022.
Vertex Press Release, "Vertex to Acquire ViaCyte, With the Goal of Accelerating its Potentially Curative VX-880 Programs in Type 1 Diabetes", (Jul. 11, 2022).
Wang D. et al., "Targeted Disruption of the B2-Microglobulin Gene Minimizes the Immunogenicity of Human Embryonic Stem Cells", Stem Cells Translational Medicine 4:1234-1245 (2015).
Invitation to Pay Additional Fees dated Oct. 21, 2021 received in International Application No. PCT/US2021/44080.
Xin Y. et al., "Pseudotime Ordering of Single Human Beta-Cells Reveals States of Insulin Production and Unfolded.Protein Response", Diabetes 67:1783-1794 (Sep. 2018) (including single-cell sequencing data stored in the Gene Expression Omnibus database under accession No. GSE114297; https://www.ncbi.nlm.nih.gov/geo/query/acc.cgi?acc=GSE114297.
Co-pending U.S. Appl. No. 18/391,867, inventors Yeh-Chuin Poh et al., filed on Dec. 21, 2023.
Co-pending U.S. Appl. No. 18/391,831, inventors Yeh-Chuin Poh et al., filed on Dec. 21, 2023.
Co-pending U.S. Appl. No. 18/391,799, inventors George Harb et al., filed on Dec. 21, 2023.
Bottino R. et al., "Pancreas and Islet Cell Transplantation", Best Practice & Research Clinical Gastroenterology 16 (3):457-474 (2002).
Pileggi A. et al., "Reversal of Diabetes by Pancreatic Islet Transplantation into a Subcutaneous, Neovascularized Device", Transplantation 81(9):1318-1324 (Mar. 15, 2006).
Akinci E. et al., "Reprogramming of Various Cell Types to a Beta-Like State by Pdx1, Ngn3 and MafA", Plos One 8(11): e82424 (Nov. 2013).
Banerjee M. et al., "A Simple Two-Step Protocol for the Purification of Human Pancreatic Beta Cells", Diabetologia 52:621-625 (2009).
Ehrhart M. et al., "Chromogranin A in the Pancreatic Islet: Cellular and Subcellular Distribution", The Journal of Histochemistry and Cytochemistry 34(12): 1673-1682 (1986).
Germanos M. et al., "Inside the Insulin Secretory Granule", Metabolites 11:515 (2021).
Lee D.D. et al., "Cellular Therapies for Type I Diabetes", Horm Metab Res. 40(2): 147-154 (Feb. 2008).
Shultz M.D. et al., "Identification of NVP-TNKS656: The Use of Structure-Efficiency Relationships to Generate a Highly Potent, Selective, and Orally Active Tankyrase Inhibitor", Journal of Medicinal Chemistry 56:6495-6511 (2013).
Millman et al., "Generation of stem cell-derived beta-cells from patients with type 1 diabetes," *Nature Communications* 7(11463), pp. 1-8, May 10, 2016.
U.S. Appl. No. 18/824,576, Harb and Xie.
U.S. Appl. No. 18/824,588, Harb and Xie.
U.S. Appl. No. 18/904,543, Harb and Xie.
Kumar et al., "Recent Development in Beta-Cell Differentiation of Pluripotent Stem Cells Induces by Small and Large Molecules," *International Journal of Moleculer Sciences*15(12):23418-23447, Dec. 17, 2014.
Ma et al., "Chemical strategies for pancreatic beta cell differentiation, reprogramming, and regeneration," *Acta Biochemica et Biophysica Sinica (Shanghai)* 49(4):289-301, Feb. 22, 2017.
Thakur et al., "Small Molecule-Induced Pancreatic Beta-Like Cell Development: Mechanistic Approaches and Available Strategies," *International Journal of Molecular Sciences* 21(7):2388, Mar. 30, 2020.
European Patent Office communication pursuant to Rule 114(2) EPC citing Third Party Observation in European Patent Application No. 21849911.9, 5 pages, (mailed Aug. 14, 2024).
Rezania et al., "Reversal of diabetes with insulin-producing cells derived in vitro from human pluripotent stem cells," *Nature Biotechnology* 32(11): 1121-1133 with the Supplemental Information (e-Pub Sep. 11, 2014), 55 pages total.

\* cited by examiner

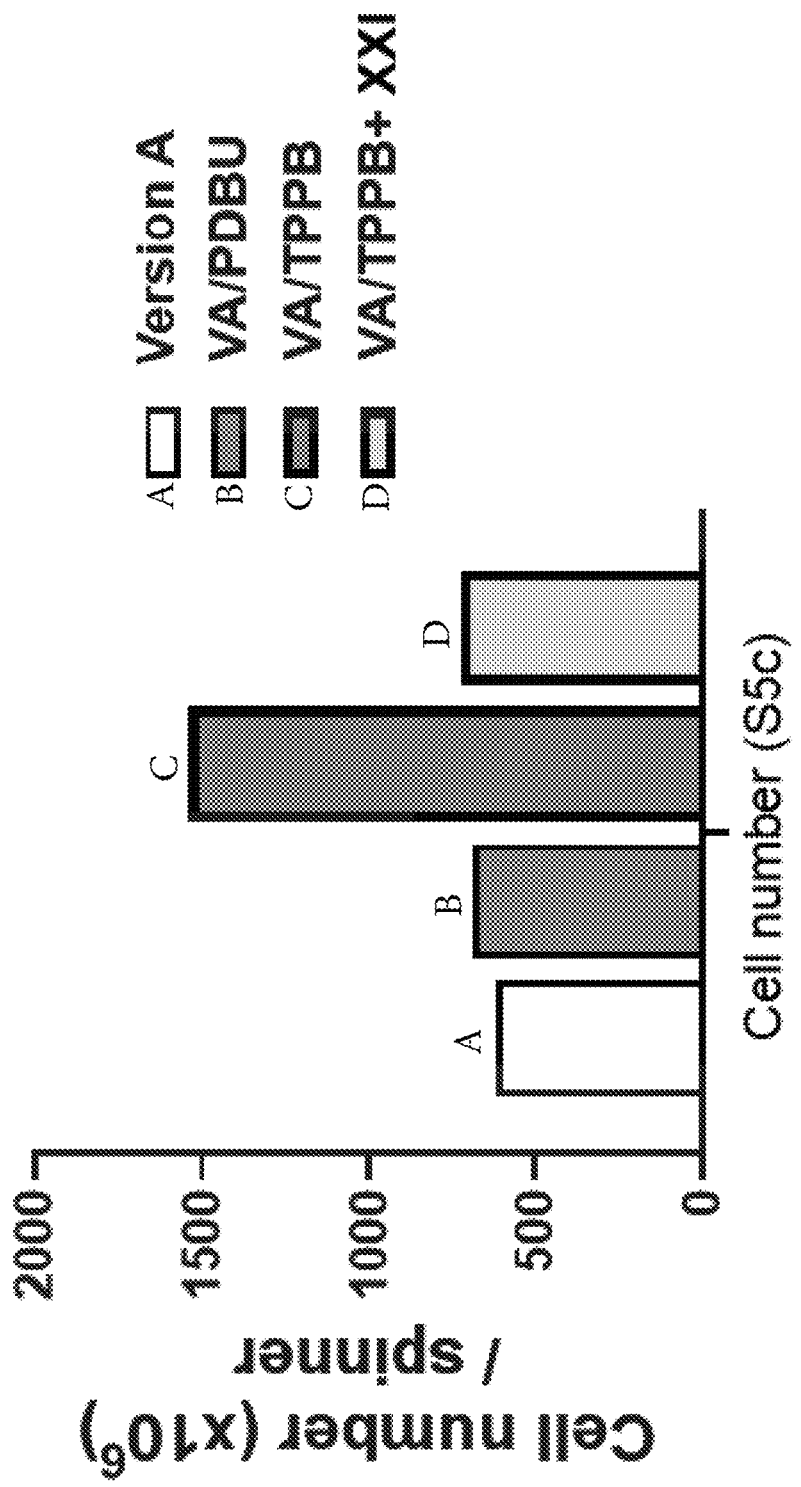

DIFFERENTIATION OF PANCREATIC ENDOCRINE CELLS

CROSS-REFERENCE TO RELATED APPLICATIONS

This application is a continuation of U.S. application Ser. No. 17/390,839, filed Jul. 30, 2021, which claims priority under 35 U.S.C. 119(e) to U.S. Provisional Patent Application No. 63/059,433, filed Jul. 31, 2020, which are hereby incorporated by reference in their entirety.

BACKGROUND

Generation of stem cell derived β-cells can provide a potentially useful step toward the generation of islets and pancreatic organs. One of the rapidly growing diseases that may be treatable by stem cell derived tissues is diabetes. Type 1 diabetes results from autoimmune destruction of β-cells in the pancreatic islet. Type 2 diabetes results from peripheral tissue insulin resistance and β-cell dysfunction. Diabetic patients, particularly those suffering from type 1 diabetes, can potentially be cured through transplantation of new β-cells. Patients transplanted with cadaveric human islets can be made insulin independent for 5 years or longer via this strategy, but this approach is limited because of the scarcity and quality of donor islets. Generation of an unlimited supply of human β-cells from stem cells can extend this therapy to millions of new patients and can be an important test case for translating stem cell biology into the clinic.

INCORPORATION BY REFERENCE

All publications, patents, and patent applications mentioned in this specification are herein incorporated by reference to the same extent as if each individual publication, patent, or patent application was specifically and individually indicated to be incorporated by reference. Absent any indication otherwise, publications, patents, and patent applications mentioned in this specification are incorporated herein by reference in their entireties.

SUMMARY

Disclosed herein, in some aspects, is a method that comprises: (a) differentiating PDX1-positive, NKX6.1-negative pancreatic progenitor cells into PDX1-positive, NKX6.1-positive pancreatic progenitor cells by contacting said PDX1-positive, NKX6.1-negative pancreatic progenitor cells with a ROCK inhibitor, a growth factor from TGF-β superfamily, a growth factor from FGF family, a RA signaling pathway activator, and a SHH pathway inhibitor, thereby generating a population of cells comprising PDX1-positive, NKX6.1-positive pancreatic progenitor cells; (b) contacting said population of cells comprising PDX1-positive, NKX6.1-positive pancreatic progenitor cells with a first composition comprising a PKC activator, a γ-secretase inhibitor, a ROCK inhibitor, a growth factor from TGFβ superfamily, a growth factor from FGF family, a RA signaling pathway activator, and a SHH pathway inhibitor, for a first time period; and (c) after said first time period, contacting said population of cells comprising PDX1-positive, NKX6.1-positive pancreatic progenitor cells with a second composition comprising a PKC activator, a γ-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, for a second time period.

Disclosed herein, in some aspects, is a method that comprises: (a) contacting a population of cells comprising PDX1-positive, NKX6.1-positive pancreatic progenitor cells with a first composition comprising a PKC activator, a γ-secretase inhibitor, and a factor selected from the group consisting of: a ROCK inhibitor, a growth factor from TGFβ superfamily, a growth factor from FGF family, a RA signaling pathway activator, and a SHH pathway inhibitor, for a first time period; and (b) after said first time period, contacting said population of cells comprising PDX1-positive, NKX6.1-positive pancreatic progenitor cells with a second composition comprising a PKC activator, a γ-secretase inhibitor, and a factor selected from the group consisting of: a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, for a second time period.

In some cases, the method further comprises after said second time period, contacting said population of cells comprising PDX1-positive, NKX6.1-positive pancreatic progenitor cells with a third composition that differentiates at least some of said PDX1-positive, NKX6.1-positive pancreatic progenitor cells into NKX6.1-positive, ISL1-positive endocrine cells, thereby generating a population of cells comprising NKX6.1-positive, ISL1-positive endocrine cells.

Disclosed herein, in some aspects, is a method that comprises: (a) contacting a population of cells comprising PDX1-positive, NKX6.1-positive pancreatic progenitor cells with a first composition comprising a PKC activator and a factor selected from the group consisting of: a ROCK inhibitor, a growth factor from TGFβ superfamily, a growth factor from FGF family, a RA signaling pathway activator, and a SHH pathway inhibitor, for a first time period; (b) after said first time period, contacting said population of cells comprising PDX1-positive, NKX6.1-positive pancreatic progenitor cells with a second composition comprising a PKC activator and a factor selected from the group consisting of: a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, for a second time period; and (c) after said second time period, contacting said population of cells comprising PDX1-positive, NKX6.1-positive pancreatic progenitor cells with a third composition that differentiates at least some of said PDX1-positive, NKX6.1-positive pancreatic progenitor cells into NKX6.1-positive, ISL1-positive endocrine cells, thereby generating a population of cells comprising NKX6.1-positive, ISL1-positive endocrine cells, wherein said population of cells comprising NKX6.1-positive, ISL1-positive endocrine cells comprises: (i) an increased proportion of cells expressing glucagon; (ii) a reduced proportion of cells expressing VMAT1; (iii) an increased proportion of cells expressing somatostatin; or (iv) an increased proportion of cells expressing C-peptide, as compared to a corresponding population of cells which is generated without said contacting of said PDX1-positive, NKX6.1-positive pancreatic progenitor cells with said PKC activator in said first composition or in said second composition.

In some cases, said third composition comprises a TGF-β signaling pathway inhibitor, a thyroid hormone (TH) signaling pathway activator, and an epigenetic modifying compound. In some cases, said third composition comprises a differentiation factor selected from the group consisting of: a TGF-β signaling pathway inhibitor, a thyroid hormone signaling pathway activator, an epigenetic modifying compound, a growth factor from EGF family, a RA signaling pathway activator, a SHH pathway inhibitor, a γ-secretase inhibitor, a protein kinase inhibitor, a ROCK inhibitor, and a BMP signaling pathway inhibitor. In some cases, said third composition comprises said TGF-β signaling pathway inhibitor, said thyroid hormone signaling pathway activator, said epigenetic modifying compound, said growth factor from EGF family, said RA signaling pathway activator, said SHH pathway inhibitor, said γ-secretase inhibitor, said protein kinase inhibitor, said ROCK inhibitor, and said BMP signaling pathway inhibitor. In some cases, said third composition does not comprise said PKC activator. In some cases, the first composition comprises said ROCK inhibitor, said growth factor from TGFβ superfamily, said growth factor from FGF family, said RA signaling pathway activator, and said SHH pathway inhibitor. In some cases, the second composition comprises said TGF-β signaling pathway inhibitor, said growth factor from EGF family, said RA signaling pathway activator, said SHH pathway inhibitor, said TH signaling pathway activator, said protein kinase inhibitor, said ROCK inhibitor, said BMP signaling pathway inhibitor, and said epigenetic modifying compound. In some cases, said population of cells comprising NKX6.1-positive, ISL1-positive endocrine cells comprises: (i) an increased proportion of cells expressing somatostatin; (ii) an increased proportion of cells expressing glucagon; (iii) a reduced proportion of cells expressing VMAT1; or (iv) an increased proportion of cells expressing C-peptide, as compared to a corresponding population of cells which is generated without said contacting of said PDX1-positive, NKX6.1-positive pancreatic progenitor cells with said PKC activator in said first composition or in said second composition. In some cases, said population of cells comprising NKX6.1-positive, ISL1-positive endocrine cells comprises: (i) an increased proportion of cells expressing somatostatin; (ii) an increased proportion of cells expressing glucagon; (iii) a reduced proportion of cells expressing VMAT1; and (iv) an increased proportion of cells expressing C-peptide, as compared to a corresponding population of cells which is generated without said contacting of said PDX1-positive, NKX6.1-positive pancreatic progenitor cells with said PKC activator in said first composition or in said second composition. In some cases, said population of cells comprising NKX6.1-positive, ISL1-positive endocrine cells comprises: at least about 4% cells expressing somatostatin, at least about 15% cells expressing glucagon, at most about 35% cells expressing VMAT1, or at least about 40% cells expressing C-peptide, as measured by flow cytometry. In some cases, said population of cells comprising NKX6.1-positive, ISL1-positive endocrine cells comprises: at least about 100% more cells expressing somatostatin, at least about 200% more cells expressing glucagon, at least about 50% fewer cells expressing VMAT1, or at least about 20% more cells expressing C-peptide, as measured by flow cytometry, as compared to a corresponding population of cells which is generated without said contacting of said PDX1-positive, NKX6.1-positive pancreatic progenitor cells with said PKC activator in said first composition or in said second composition. In some cases, first time period is from one to three days. In some cases, said first time period is about two days. In some cases, said second time period is from one to three days. In some cases, said second time period is about two days. In some cases, said PKC activator is selected from the group consisting of: phorbol 12,13-dibutyrate (PDBU), FR 236924, Prostratin, SC-9, and TPPB. In some cases, said PKC activator comprises PDBU. In some cases, said PKC activator is contacted to said population of cells comprising PDX1-positive, NKX6.1-positive pancreatic progenitor cells at a concentration from 100 nM to 1000 nM. In some cases, said PKC activator is contacted to said population of cells comprising PDX1-positive, NKX6.1-positive pancreatic progenitor cells at a concentration about 500 nM. In some cases, said γ-secretase inhibitor comprises XXI. In some cases, said γ-secretase inhibitor is contacted to said population of cells comprising PDX1-positive, NKX6.1-positive pancreatic progenitor cells at a concentration from 0.5 μM to 10 μM. In some cases, said γ-secretase inhibitor is contacted to said population of cells comprising PDX1-positive, NKX6.1-positive pancreatic progenitor cells at a concentration about 2 μM.

In some cases, the method further comprises: obtaining said population of cells comprising PDX1-positive, NKX6.1-positive pancreatic progenitor cells by contacting a population of cells comprising PDX1-positive, NKX6.1-negative pancreatic progenitor cells with a composition comprising said PDX1-positive, NKX6.1-negative pancreatic progenitor cells with a ROCK inhibitor, a growth factor from TGFβ superfamily, a growth factor from FGF family, a RA signaling pathway activator, and a SHH pathway inhibitor, and differentiating said PDX1-positive, NKX6.1-negative pancreatic progenitor cells into said PDX1-positive, NKX6.1-positive pancreatic progenitor cells. In some cases, the method further comprises: differentiating FOXA2-positive, PDX1-negative primitive gut tube cells into said PDX1-positive, NKX6.1-negative pancreatic progenitor cells by contacting said FOXA2-positive, PDX1-negative primitive gut tube cells with a ROCK inhibitor, a growth factor from FGF family, a BMP signaling pathway inhibitor, a PKC activator, a retinoic acid signaling pathway activator, a SHH pathway inhibitor, and a growth factor from TGF-β superfamily. In some cases, the method further comprises: differentiating definitive endoderm cells into said FOXA2-positive, PDX1-negative gut tube cells by contacting said definitive endoderm cells with a growth factor from FGF family.

Disclosed herein, in some aspects, is a method, comprising: (a) differentiating pluripotent stem cells in a population into definitive endoderm cells by contacting said pluripotent stem cells with a growth factor from TGF-β superfamily and a WNT signaling pathway activator; (b) differentiating said definitive endoderm cells into FOXA2-positive, PDX1-negative primitive gut tube cells by contacting said definitive endoderm cells with a growth factor from FGF family; (c) differentiating said FOXA2-positive, PDX1-negative primitive gut tube cells into PDX1-positive, NKX6.1-negative pancreatic progenitor cells by contacting said FOXA2-positive, PDX1-negative primitive gut tube cells with a ROCK inhibitor, a growth factor from FGF family, a BMP signaling pathway inhibitor, a PKC activator, a retinoic acid signaling pathway activator, a SHH pathway inhibitor, and a growth factor from TGF-β superfamily; (d) differentiating said PDX1-positive, NKX6.1-negative pancreatic progenitor cells into PDX1-positive, NKX6.1-positive pancreatic progenitor cells by contacting said PDX1-positive, NKX6.1-negative pancreatic progenitor cells with a ROCK inhibitor, a growth factor from TGFβ superfamily, a growth factor from FGF family, a RA signaling pathway activator, and a SHH pathway inhibitor; (e) incubating said PDX1-positive, NKX6.1-positive pancreatic progenitor cells with a first composition comprising a PKC activator, a γ-secretase inhibitor, a factor selected from the group consisting of: a ROCK inhibitor, a growth factor from TGFβ superfamily, a growth factor from FGF family, a RA signaling pathway activator, and a SHH pathway inhibitor, for a first time period of one to three days; and (f) after (e), incubating said PDX1-positive, NKX6.1-positive pancreatic progenitor cells with a second composition comprising said PKC activator, said γ-secretase inhibitor, a factor selected from the group consisting of: a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, for a second time period of one to three days; (g) after (f), differentiating said PDX1-positive, NKX6.1-positive pancreatic progenitor cells into a cell population comprising NKX6.1-positive, ISL1-positive endocrine cells by contacting said PDX1-positive, NKX6.1-positive pancreatic progenitor cells with a TGF-β signaling pathway inhibitor, a growth factor from EGF family, a RA signaling pathway activator, a SHH pathway inhibitor, a TH signaling pathway activator, a γ-secretase inhibitor, a protein kinase inhibitor, a ROCK inhibitor, a BMP signaling pathway inhibitor, and an epigenetic modifying compound. In some cases, said SHH pathway inhibitor comprises SANT1; said RA signaling pathway activator comprises retinoic acid; said γ-secretase inhibitor comprises XXI; said growth factor from the EGF family comprises betacellulin; said BMP signaling pathway inhibitor comprises LDN or DMH; said TGF-β signaling pathway inhibitor comprises Alk5 inhibitor II; said thyroid hormone signaling pathway activator comprises GC-1; said protein kinase inhibitor comprises staurosporine; said ROCK inhibitor comprises thiazovivin; or said epigenetic modifying compound comprises DZNep, GSK126, or EPZ6438.

Disclosed herein, in some aspects, is a method that comprises: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and a γ-secretase inhibitor and one or more of a ROCK inhibitor, a growth factor from the TGFβ superfamily, a growth factor from the FGF family, a RA signaling pathway activator, and a SHH pathway inhibitor, thereby generating a second population of cells; and (c) contacting the second population of cells with a PKC activator, a γ-secretase inhibitor and one or more of a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells.

Disclosed herein, in some aspects, is a method that comprises contacting a population of cells with a γ-secretase inhibitor and one or both of a growth factor from the TGFβ superfamily and a growth factor from the FGF family. In some embodiments, the population of cells comprises PDX1-positive cells. In some embodiments, the population of cells comprises PDX1-positive, NKX6.1-negative cells. In some embodiments, the population of cells comprises PDX1-positive, NKX6.1-positive cells.

Disclosed herein, in some aspects, is a method that comprises (a) contacting a plurality of PDX1-positive, NKX6.1-negative pancreatic progenitor cells with one or more of a ROCK inhibitor, a growth factor from the TGFβ superfamily, a growth factor from the FGF family, a RA signaling pathway activator, and a SHH pathway inhibitor, for a period of no more than 1-5 days, thereby generating a first population of cells; (b) contacting the first population of cells with a γ-secretase inhibitor. In some embodiments, the contacting of step (a) is for a period of 4 or 5 days. In some embodiments, step (b) further comprises contacting the first population of cells with one or more of a PKC activator, a ROCK inhibitor, a growth factor from the TGFβ superfamily, a growth factor from the FGF family, a RA signaling pathway activator, and a SHH pathway inhibitor.

Disclosed herein, in some aspects, is a method that comprises: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and one or more of a ROCK inhibitor, a growth factor from the TGFβ superfamily, a growth factor from the FGF family, a RA signaling pathway activator, and a SHH pathway inhibitor, thereby generating a second population of cells; wherein the PKC activator is a benzolactam-derivative; and (c) contacting the second population of cells with the PKC activator, a γ-secretase inhibitor, and one or more of a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells.

In some cases, the benzolactam-derivative is TPPB. In some cases, step (b) further comprises contacting the first population of cells with a γ-secretase inhibitor. In some cases, the method further comprises: (d) contacting the third population of cells with one or more of a TGF-β signaling pathway inhibitor, a RA signaling pathway activator, a TH signaling pathway activator, a protein kinase inhibitor, a ROCK inhibitor, a BMP signaling pathway inhibitor, and an epigenetic modifying compound, thereby generating a fourth population of cells. In some cases, step (d) does not comprise contacting the third population of cells with a PKC activator. In some cases, step (d) does not comprise contacting the third population of cells with a γ-secretase inhibitor. In some cases, step (d) does not comprise contacting the third population of cells with a SHH pathway inhibitor. In some cases, step (d) does not comprise contacting the third population of cells with a growth factor from EGF family. In some cases, the method further comprises: (e) contacting the fourth population of cells with one or more of a serum albumin protein, vitamin C, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound, thereby generating a fifth population of cells. In some cases, step (e) comprises contacting the fourth population of cells with a PKC activator.

Disclosed herein, in some aspects, is a method that comprises: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and one or more of a ROCK inhibitor, a growth factor from the TGFβ superfamily, a growth factor from the FGF family, a RA signaling pathway activator, and a SHH pathway inhibitor, thereby generating a second population of cells; (c) contacting the second population of cells with a PKC activator and one or more of a γ-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells; (d) contacting the third population of cells with one or more of a TGF-β signaling pathway inhibitor, a RA signaling pathway activator, a TH signaling pathway activator, a protein kinase inhibitor, a ROCK inhibitor, a BMP signaling pathway inhibitor, and an epigenetic modifying compound, thereby generating a fourth population of cells; and (e) contacting the fourth population of cells with a PKC activator and one or more of a serum albumin protein, vitamin C, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound, thereby generating a fifth population of cells.

In some cases, step (e) comprises contacting the fourth population of cells with a serum albumin protein. In some cases, step (a) is performed over the course of 1, 2, 3, 4, 5 or 6 days. In some cases, step (a) is performed over the course of 3-5 days (e.g., 4 days). In some cases, step (b) is performed over the course of 1, 2, 3 or 4 days. In some cases, step (b) is performed over the course of 1-3 days (e.g., 2 days). In some cases, step (c) is performed over the course of 1, 2, 3, or 4 days. In some cases, step (c) is performed over the course of 1-3 days (e.g., 2 days). In some cases, step (d) is performed over the course of 1, 2, 3, 4, 5, 6, or 7 days. In some cases, step (d) is performed over the course of 4-6 days (e.g., 5 days). In some cases, step (e) is performed over the course of 1, 2, 3, 4, 5, 6, 7, 8, 9, 10, 11, 12, 13, 14, or 15 days. In some cases, step (e) is performed over the course of 10-12 days. In some cases, the first population of cells comprises PDX1-positive, NKX6.1-negative cells and/or PDX1-positive, NKX6.1-positive cells. In some cases, the second population of cells comprises PDX1-positive and NKX6.1-positive cells. In some cases, the third population of cells comprises PDX1-positive, NKX6.1-positive, ISL1-negative cells and/or PDX1-positive, NKX6.1-positive, ISL1-positive cells. In some cases, the fourth population of cells comprises PDX1-positive, NKX6.1-positive, ISL1-positive cells. In some cases, the fifth population of cells comprises cells that express C-peptide and ISL1 but not VMAT1. In some cases, 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the fourth population of cells express C-peptide and ISL1 but not VMAT1. In some cases, 40-60% of the cells in the fourth population of cells express C-peptide and ISL1 but not VMAT1. In some cases, the fourth population of cells comprises cells that express glucagon but not somatostatin. In some cases, 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the fourth population of cells express glucagon but not somatostatin. In some cases, 10-25% of the cells in the fourth population of cells express somatostatin but not glucagon. In some cases, the fourth population of cells comprises cells that express somatostatin but not glucagon. In some cases, 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the fourth population of cells express somatostatin but not glucagon. In some cases, step (a) comprises contacting a plurality of PDX1-positive, NKX6.1-negative pancreatic progenitor cells with a ROCK inhibitor, a growth factor from TGFβ superfamily, a growth factor from FGF family, a RA signaling pathway activator, and a SHH pathway inhibitor. In some cases, step (b) comprises contacting the first population of cells with a ROCK inhibitor, a growth factor from the TGFβ superfamily, a growth factor from the FGF family, a RA signaling pathway activator, and a SHH pathway inhibitor. In some cases, step (c) comprises contacting the second population of cells with a gamma-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound. In some cases, step (d) comprises contacting the third population of cells with serum albumin protein, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound. In some cases, the ROCK inhibitor for use in step (a), (b), (c), (d), and/or (e) is thiazovavin or Y-27632. In some cases, the growth factor from the TGFβ superfamily for use in steps (a) and/or (b) is activin A. In some cases, the growth factor from the FGF family for use in steps (a) and/or (b) is KGF. In some cases, the RA signaling pathway activator for use in steps (a), (b) and/or (c) is retinoic acid. In some cases, the SHH pathway inhibitor for use in steps (a), (b) and/or (c) is Sant-1. In some cases, the PKC activator for use in steps (b), (c) and/or (d) is selected from the group consisting of: phorbol 12,13-dibutyrate (PDBU), FR 236924, Prostratin, SC-9, and TPPB. In some cases, the PKC activator is PDBU. In some cases, the γ-secretase inhibitor for use in step (b) and/or (c) is XXI. In some cases, the TGF-β signaling pathway inhibitor for use in step (c), (d), and/or (e) is ALK5i. In some cases, the growth factor from the EGF family for use in step (c) is betacellulin. In some cases, the TH signaling pathway activator for use in step (c), (d), and/or (e) is T3, GC-1 or a thyroid hormone derivative. In some cases, the protein kinase inhibitor for use in step (c), (d), and/or (e) is staurosporine. In some cases, the BMP signaling pathway inhibitor for use in step (c), (d), and/or (e) is LDN193189 or DMH-1. In some cases, the epigenetic modifying compound for use in step (c), (d), and/or (e) is DZNep.

Disclosed herein, in some aspects, is an in vitro composition that comprises PDX1-positive, NKX6.1-positive pancreatic progenitor cells; NKX6.1-positive, ISL1-positive endocrine cells; a PKC activator; and a γ-secretase inhibitor.

Disclosed herein, in some aspects, is an in vitro composition that comprises PDX1-positive, NKX6.1-negative pancreatic progenitor cells; PDX1-positive, NKX6.1-positive pancreatic progenitor cells; a PKC activator; and a γ-secretase inhibitor. In some embodiments, at least 10%, 20%, 30%, 40%, 50%, 60%, 70%, 80%, or 90% of the cells in the composition are PDX1-positive, NKX6.1-positive pancreatic progenitor cells. In some embodiments, less than 90%, 80%, 70%, 60%, 50%, 40%, 30%, 20%, or 10% of the cells in the composition are PDX1-positive, NKX6.1-negative pancreatic progenitor cells.

In some embodiments of the composition, said PKC activator is selected from the group consisting of: phorbol 12,13-dibutyrate (PDBU), FR 236924, Prostratin, SC-9, and TPPB. In some cases, the γ-secretase inhibitor is DAPT (N—[N-(3,5-Difluorophenacetyl)-L-alanyl]-S-phenylglycine t-butyl ester). In some cases, the γ-secretase inhibitor is XXI.

In some embodiments of the composition, the composition further comprises a growth factor from the FGF family. In some embodiments, the growth factor from the FGF family is KGF. In some embodiments, the composition further comprises a growth factor of the TGFβ superfamily. In some embodiments, the growth factor of the TGFβ superfamily is activin A.

Disclosed herein, in some aspects, is an in vitro composition that comprises PDX1-positive, NKX6.1-positive pancreatic progenitor cells; NKX6.1-positive, ISL1-positive endocrine cells; and a PKC activator; wherein the PKC activator is a benzolactam derivative.

In some embodiments of the composition, the PKC activator is TPPB. In some cases, the composition further comprises a γ-secretase inhibitor. In some cases, the γ-secretase inhibitor is DAPT. In some cases, the γ-secretase inhibitor is XXI. In some cases, the composition further comprises a differentiation factor selected from the group consisting of: a TGF-β signaling pathway inhibitor, a thyroid hormone signaling pathway activator, an epigenetic modifying compound, a growth factor from EGF family, a RA signaling pathway activator, a SHH pathway inhibitor, a protein kinase inhibitor, a ROCK inhibitor, and a BMP signaling pathway inhibitor. In some cases, the composition further comprises serum albumin protein. In some cases, the composition further comprises serum albumin protein, a TGF-β signaling pathway inhibitor, a thyroid hormone signaling pathway activator, an epigenetic modifying compound, a SHH pathway inhibitor, a protein kinase inhibitor, a ROCK inhibitor, and a BMP signaling pathway inhibitor. In some cases, the ROCK inhibitor is thiazovavin. In some cases, the RA signaling pathway activator is retinoic acid. In some cases, the SHH pathway inhibitor is Sant-1. In some cases, the TGF-β signaling pathway inhibitor is ALK5i. In some cases, the growth factor from the EGF family is betacellulin. In some cases, the thyroid hormone signaling pathway activator is T3, GC-1 or a thyroid hormone derivative. In some cases, the protein kinase inhibitor is staurosporine. In some cases, the BMP signaling pathway inhibitor is LDN193189 or DMH-1. In some cases, the epigenetic modifying compound is DZNep.

Disclosed herein, in some aspects, is a composition that comprises an in vitro cell population, wherein said cell population comprises: (a) at least about 35% cells expressing C-peptide and not expressing VMAT1; and (b) at most about 35% cells expressing VMAT1, or at least about 15% cells expressing glucagon (e.g., as measured by flow cytometry). In some aspects, the disclosure provides a composition that comprises an in vitro cell population, wherein said cell population comprises: at least about 35% cells expressing C-peptide and not expressing VMAT1; and (i) at most about 35% cells expressing VMAT1, and/or (ii) at least about 15% cells expressing glucagon. In some embodiments, the percentages of cells are measured by flow cytometry.

In some cases, said cell population comprises at most about 30% cells expressing VMAT1 and at least about 20% cells expressing glucagon. In some cases, said cell population comprises at most about 30% cells expressing VMAT1 and at least about 20% cells expressing glucagon, as measured by flow cytometry. In some cases, said cell population comprises at least about 15% cells expressing glucagon and not expressing somatostatin. In some cases, said cell population comprises at least about 4% cells expressing somatostatin and not expressing glucagon.

Disclosed herein, in some aspects, is a composition that comprises a population of cells, wherein: a) 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the population of cells express C-peptide and ISL1 but not VMAT1; b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and/or c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

Disclosed herein, in some aspects, is a composition that comprises a population of cells, wherein: a) 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the population of cells express C-peptide and ISL1 but not VMAT1; b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

Disclosed herein, in some aspects, is a composition that comprises a population of cells, wherein: a) 5-35%, 5-30%, 5-25%, 5-20%, 5-15%, 10-35%, 10-30%, 10-25%, 10-20%, 10-15%, 15-35%, 15-30%, 15-25%, 15-20%, 20-35%, 20-30%, 20-25%, 25-35%, 25-30%, or 30-35%, of the cells in the population of cells express VMAT1 but not C-peptide; b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and/or c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

Disclosed herein, in some aspects, is a composition that comprises a population of cells, wherein: a) 5-35%, 5-30%, 5-25%, 5-20%, 5-15%, 10-35%, 10-30%, 10-25%, 10-20%, 10-15%, 15-35%, 15-30%, 15-25%, 15-20%, 20-35%, 20-30%, 20-25%, 25-35%, 25-30%, or 30-35%, of the cells in the population of cells express VMAT1 but not C-peptide; b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

In some embodiments of the composition, 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the population of cells express C-peptide and ISL1 but not VMAT1.

In some embodiments of the composition, 40-60% of the cells in the population of cells express C-peptide and ISL1 but not VMAT1; 10-25%, of the cells in the population of cells express glucagon but not somatostatin; and 4-10% of the cells in the population of cells express somatostatin but not glucagon. In some cases, less than 25%, less than 20%, less than 18%, less than 15%, less than 12%, or less than 10% of the cells in the population of cells express VMAT1 but not C-peptide. In some cases, the population of cells are generated from stem cells in vitro. In some cases, the cells expressing C-peptide and not expressing VMAT1 exhibit glucose-stimulated insulin secretion response in vitro. In some cases, secretion of insulin by the cells expressing C-peptide and not expressing VMAT1 in response to a glucose challenge is proportional to glucose concentration of the glucose challenge. In some cases, the cells expressing C-peptide and not expressing VMAT1 secrete insulin in response to one or more glucose challenges. In some cases, the cells expressing C-peptide and not expressing VMAT1 secrete insulin in response to a first glucose challenge, a second glucose challenge, and a third glucose challenge, wherein the first glucose challenge, the second glucose challenge, and the third glucose challenge are applied sequentially.

Disclosed herein, in some aspects, is an in vitro composition comprising PDX1-positive cells, a γ-secretase inhibitor, and one or both of a growth factor from the TGFβ superfamily and a growth factor from the FGF family. In some embodiments, the composition of cells comprises PDX1-positive, NKX6.1-negative cells. In some embodiments, the composition of cells comprises PDX1-positive, NKX6.1-positive cells.

In some embodiments, the composition further comprises any one of or combination of a PKC activator, a growth factor from the FGF family, a ROCK inhibitor, a growth factor from the TGFβ superfamily, a sonic hedgehog pathway inhibitor, and a retinoic acid signaling pathway activator.

Disclosed herein, in some aspects, is an in vitro composition comprising PDX1-positive, NKX6.1-negative pancreatic progenitor cells; PDX1-positive, NKX6.1-positive pancreatic progenitor cells; and a γ-secretase inhibitor. In some embodiments, the γ-secretase inhibitor is XXI.

In some embodiments, at least 10%, at least 20%, at least 30%, at least 40%, at least 50%, at least 60%, at least 70%, at least 80%, or at least 90% of the cells in the composition are PDX1-positive, NKX6.1-positive pancreatic progenitor cells. In some embodiments, less than 90%, less than 80%, less than 70%, less than 60%, less than 50%, less than 40%, less than 30%, less than 20%, or less than 10% of the cells in the composition are PDX1-positive, NKX6.1-negative pancreatic progenitor cells.

In some embodiments, the composition further comprises a growth factor from the FGF family. In some embodiments, the composition further comprises a sonic hedgehog pathway inhibitor. In some embodiments, the composition further comprises a ROCK inhibitor. In some embodiments, the composition further comprises a growth factor from the TGFβ superfamily. In some embodiments, the composition further comprises a retinoic acid signaling pathway activator. In some embodiments, the composition further comprises a PKC activator.

In some embodiments, the composition further comprises any two of a PKC activator, a growth factor from the FGF family, a ROCK inhibitor, a growth factor from the TGFβ superfamily, a sonic hedgehog pathway inhibitor, and a retinoic acid signaling pathway activator. In some embodiments, the composition further comprises any three of a PKC activator, a growth factor from the FGF family, a ROCK inhibitor, a growth factor from the TGFβ superfamily, a sonic hedgehog pathway inhibitor, and a retinoic acid signaling pathway activator. In some embodiments, the composition further comprises any four of a PKC activator, a growth factor from the FGF family, a ROCK inhibitor, a growth factor from the TGFβ superfamily, a sonic hedgehog pathway inhibitor, and a retinoic acid signaling pathway activator. In some embodiments, the composition further comprises any five of a PKC activator, a growth factor from the FGF family, a ROCK inhibitor, a growth factor from the TGFβ superfamily, a sonic hedgehog pathway inhibitor, and a retinoic acid signaling pathway activator. In some embodiments, the composition further comprises any six of a PKC activator, a growth factor from the FGF family, a ROCK inhibitor, a growth factor from the TGFβ superfamily, a sonic hedgehog pathway inhibitor, and a retinoic acid signaling pathway activator.

In some embodiments of the composition, the growth factor from the FGF family is KGF. In some embodiments, the sonic hedgehog pathway inhibitor is SANT-1. In some embodiments, the ROCK inhibitor is thiazovivin. In some embodiments, the growth factor from the TGFβ superfamily is activin A. In some embodiments, the retinoic acid signaling pathway activator is retinoic acid. In some embodiments, the PKC activator is PDBU.

Disclosed herein, in some aspects, is a population of in vitro differentiated cells comprising NKX6.1-positive, ISL1-positive cells and NKX6.1-negative, ISL1-positive cells; wherein the population comprises more NKX6.1-negative, ISL1-positive cells than NKX6.1-positive, ISL1-positive cells; and wherein at least 73% of the cells in the population are ISL1-positive cells. In some embodiments, less than 12% of the cells in the population are NKX6.1-negative, ISL1-negative cells.

Disclosed herein, in some aspects, is a population of in vitro differentiated cells comprising NKX6.1-positive, ISL1-positive cells and NKX6.1-negative, ISL1-positive cells; wherein at least 40% of the cells in the population are NKX6.1-negative, ISL1-positive cells. In some embodiments, less than 12% of the cells in the population are NKX6.1-negative, ISL1-negative cells.

Disclosed herein, in some aspects, is a population of in vitro differentiated cells comprising NKX6.1-positive, ISL1-positive cells and NKX6.1-negative, ISL1-positive cells; and wherein less than 12% of the cells in the population are NKX6.1-negative, ISL1-negative cells.

In some embodiments, less than 10%, less than 8%, less than 6%, or less than 4% of the cells in the population are NKX6.1-negative, ISL1-negative cells. In some embodiments, at least 60%, at least 65%, at least 70%, at least 73%, at least 75%, or at least 80% of the cells in the population are ISL1-positive cells. In some embodiments, 2-12%, 4-12%, 6-12%, 8-12%, 2-8%, 4-8%, 3-6% or 3-5% of the cells in the population are NKX6.1-negative, ISL1-negative cells. In some embodiments, 50-90%, 50-85%, 50-80%, 50-75%, 50-70%, 50-60%, 60-90%, 60-85%, 60-80%, 60-75%, 60-70%, 65-90%, 65-85%, 65-80%, 65-75%, 65-70%, 70-90%, 70-85%, 70-80%, 70-75%, 75-90%, 75-85%, 75-80%, 80-90%, 80-85%, or 85-90% of the cells in the population are ISL1-positive cells.

In some embodiments, the population comprises more NKX6.1-negative, ISL1-positive cells than NKX6.1-positive, ISL1-positive cells. In some embodiments, at least 40% of the cells in the population are NKX6.1-negative, ISL1-positive cells. In some embodiments, at least 45%, at least 50%, about 40-50%, about 45-55%, or about 50-55% of the cells in the population are NKX6.1-negative, ISL1-positive cells. In some embodiments, at least 74%, at least 75%, at least 80%, at least 85%, at least 90%, about 85-95%, or about 90-95% of the cells in the population are ISL1-positive cells.

In some embodiments, the population comprises more stem cell-derived alpha cells than stem cell-derived beta cells. In some embodiments, the population of cells is derived from stem cells in vitro.

In some embodiments, the population further comprises a medium. In some embodiments, the medium comprises a sugar. In some embodiments, the sugar is sucrose or glucose. In some embodiments, the medium comprises the sugar at a concentration of between about 0.05% and about 1.5%. In some embodiments, the medium is a CMRL medium; or wherein the medium is HypoThermosol® FRS Preservation Media.

In some embodiments, the population of cells is in a cell cluster. In some embodiments, the population of cells are in one or more cell cluster. In some embodiments, the cell cluster is between about 125 and about 225 microns in diameter, between about 130 and about 160 microns in diameter, between about 170 and about 225 microns in diameter, between about 140 and about 200 microns in diameter, between about 140 and about 170 microns in diameter, between about 160 and about 220 microns in diameter, between about 170 and about 215 microns in diameter, or between about 170 and about 200 microns in diameter.

In some embodiments, the population has a genetic disruption in the beta-2-microglobulin gene.

In some embodiments, the population comprises NKX6.1-positive, ISL1-positive cells that express lower levels of MAFA than NKX6.1-positive, ISL1-positive cells from the pancreas of a healthy control adult subject. In some embodiments, the population comprises NKX6.1-positive, ISL1-positive cells that express higher levels of MAFB than NKX6.1-positive, ISL1-positive cells from the pancreas of a healthy control adult subject. In some embodiments, the population comprises NKX6.1-positive, ISL1-positive cells that express higher levels of SIX2, HOPX, IAPP and/or UCN3 than NKX6.1-positive, ISL 1-positive cells from the pancreas of a healthy control adult subject.

In some embodiments, the population comprises NKX6.1-positive, ISL1-positive cells that do not express MAFA. In some embodiments, the population comprises NKX6.1-positive, ISL1-positive cells that express MAFB.

In some embodiments, the population is contained in a device for implantation into a subject. In some aspects, the present disclosure provides an implantable encapsulation device comprising the population. In some embodiments, the device has been implanted in a subject having diabetes. In some embodiments, the subject has Type I Diabetes. In some aspects, the present disclosure provides a method of treating a subject, the method comprising administering to the subject a composition comprising the population, or implanting in the subject the device.

Disclosed herein, in some aspects, is a pharmaceutical composition that comprises the composition disclosed herein, or the cell population produced according to the method disclosed herein, and a pharmaceutically acceptable excipient or carrier.

Disclosed herein, in some aspects, is a device that comprises the composition disclosed herein, or the cell population produced according to the method disclosed herein, wherein the device is configured to produce and release insulin when implanted into a subject.

Disclosed herein, in some aspects, is a method of treating a subject that comprises administering the subject with the composition disclosed hereinv, or the cell population produced according to the method disclosed herein, or the device disclosed herein.

BRIEF DESCRIPTION OF THE DRAWINGS

The features of the present disclosure are set forth with particularity in the appended claims. A better understanding of the features and advantages of the present will be obtained by reference to the following detailed description that sets forth illustrative embodiments, in which the principles of the disclosure are utilized, and the accompanying drawings of which:

FIGS. 11A-11C summarize the percentage of NKX6.1-positive/negative and ISL1-positive/negative cells (FIG. 11B) in the in vitro cell populations generated according to three exemplary differentiation protocols: a) Version A without PDBU or TPPB (Version A); b) with PDBU (VA/PDBU); or c) with TPPB (VA/TPPB), as measured by flow cytometry (FIG. 11A). FIG. 11C shows the cell yield for Version A, VA/PDBU, VA/TPPB, as well as VA/TPPB+XXI.

DETAILED DESCRIPTION

Figure 1:
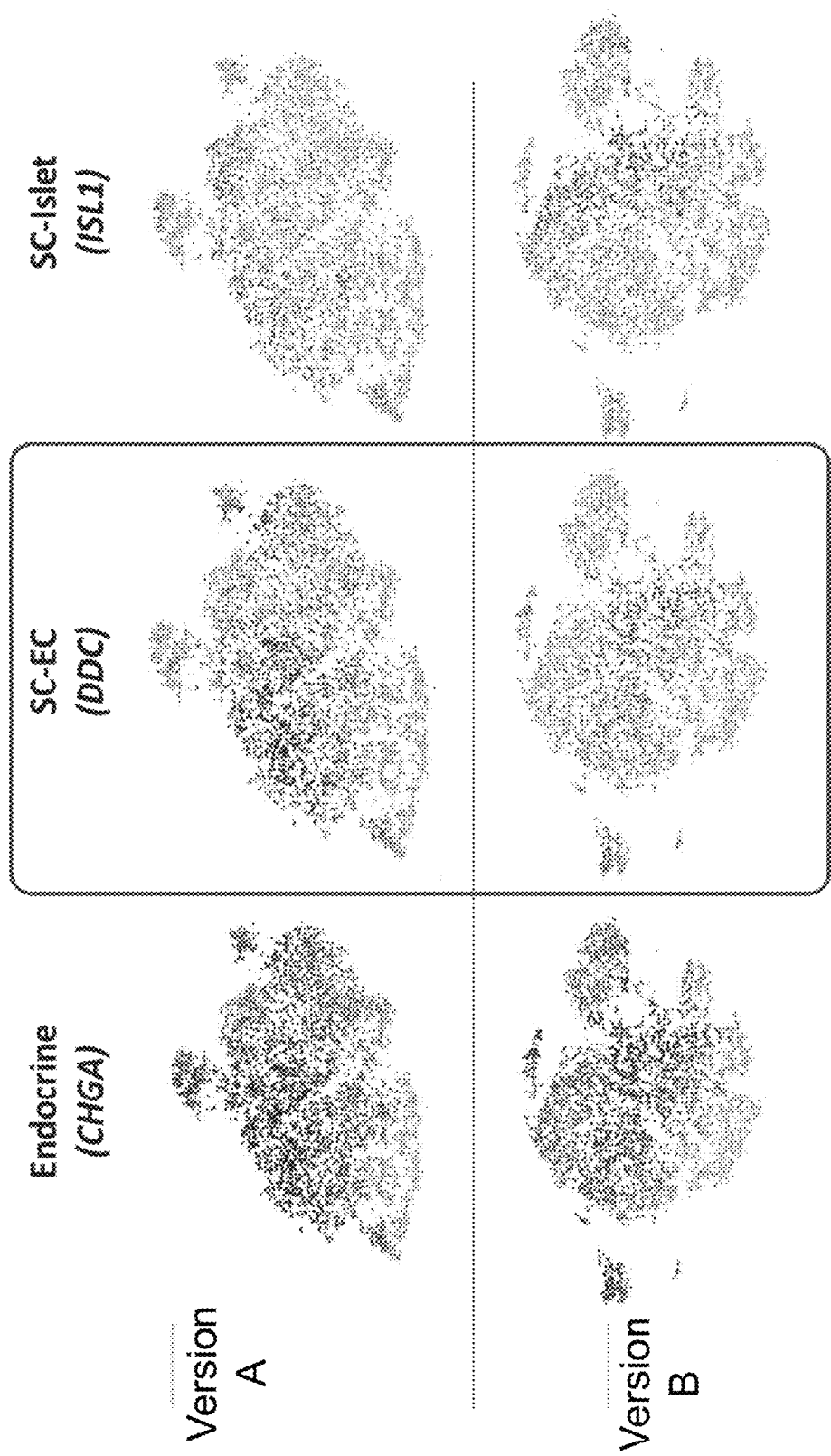
FIG. 1 shows single-cell sequencing results of in vitro endocrine cell populations generated according to two exemplary differentiation protocols (Version A and Version B), with or without PDBU applied on S4d5 to S5d2.

The following description and examples illustrate embodiments of the present disclosure in detail. It is to be understood that this disclosure is not limited to the particular embodiments described herein and as such can vary. Those of skill in the art will recognize that there are numerous variations and modifications of this disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "diabetes" and its grammatical equivalents as used herein can refer to is a disease characterized by high blood sugar levels over a prolonged period. For example, the term "diabetes" and its grammatical equivalents as used herein can refer to all or any type of diabetes, including, but not limited to, type 1, type 2, cystic fibrosis-related, surgical, gestational diabetes, and mitochondrial diabetes. In some cases, diabetes can be a form of hereditary diabetes.

The term "endocrine cell(s)," if not particularly specified, can refer to hormone-producing cells present in the pancreas of an organism, such as "islet", "islet cells", "islet equivalent", "islet-like cells", "pancreatic islets" and their grammatical equivalents. In an embodiment, the endocrine cells can be differentiated from pancreatic progenitor cells or precursors. Islet cells can comprise different types of cells, including, but not limited to, pancreatic α cells, pancreatic β cells, pancreatic δ cells, pancreatic F cells, and/or pancreatic cells. Islet cells can also refer to a group of cells, cell clusters, or the like.

The terms "progenitor" and "precursor" cell are used interchangeably herein and refer to cells that have a cellular phenotype that is more primitive (e.g., is at an earlier step along a developmental pathway or progression than is a fully differentiated cell) relative to a cell which it can give rise to by differentiation. Often, progenitor cells can also have significant or very high proliferative potential. Progenitor cells can give rise to multiple distinct differentiated cell types or to a single differentiated cell type, depending on the developmental pathway and on the environment in which the cells develop and differentiate.

A "precursor thereof" as the term related to an insulin-positive endocrine cell can refer to any cell that is capable of differentiating into an insulin-positive endocrine cell, including for example, a pluripotent stem cell, a definitive endoderm cell, a primitive gut tube cell, a pancreatic progenitor cell, or endocrine progenitor cell, when cultured under conditions suitable for differentiating the precursor cell into the insulin-positive endocrine cell.

The terms "stem cell-derived β cell," "SC-β cell," "functional β cell," "functional pancreatic β cell," "mature SC-β cell," and their grammatical equivalents can refer to cells (e.g., non-native pancreatic β cells) that display at least one marker indicative of a pancreatic β cell (e.g., PDX-1 or NKX6.1), expresses insulin, and display a glucose stimulated insulin secretion (GSIS) response characteristic of an endogenous mature β cell. In some embodiments, the terms "SC-β cell" and "non-native β cell" as used herein are interchangeable. In some embodiments, the "SC-β cell" comprises a mature pancreatic cell. It is to be understood that the SC-β cells need not be derived (e.g., directly) from stem cells, as the methods of the disclosure are capable of deriving SC-β cells from any insulin-positive endocrine cell or precursor thereof using any cell as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc., as the invention is not intended to be limited in this manner). In some embodiments, the SC-β cells exhibit a response to multiple glucose challenges (e.g., at least one, at least two, or at least three or more sequential glucose challenges). In some embodiments, the response resembles the response of endogenous islets (e.g., human islets) to multiple glucose challenges. In some embodiments, the morphology of the SC-β cell resembles the morphology of an endogenous β cell. In some embodiments, the SC-β cell exhibits an in vitro GSIS response that resembles the GSIS response of an endogenous β cell. In some embodiments, the SC-β cell exhibits an in vivo GSIS response that resembles the GSIS response of an endogenous β cell. In some embodiments, the SC-β cell exhibits both an in vitro and in vivo GSIS response that resembles the GSIS response of an endogenous β cell. The GSIS response of the SC-β cell can be observed within two weeks of transplantation of the SC-β cell into a host (e.g., a human or animal) In some embodiments, the SC-β cells package insulin into secretory granules. In some embodiments, the SC-β cells exhibit encapsulated crystalline insulin granules. In some embodiments, the SC-β cells exhibit a stimulation index of greater than 1. In some embodiments, the SC-β cells exhibit a stimulation index of greater than 1.1. In some embodiments, the SC-β cells exhibit a stimulation index of greater than 2. In some embodiments, the SC-β cells exhibit cytokine-induced apoptosis in response to cytokines. In some embodiments, insulin secretion from the SC-β cells is enhanced in response to known antidiabetic drugs (e.g., secretagogues). In some embodiments, the SC-β cells are monohormonal. In some embodiments, the SC-β cells do not abnormally co-express other hormones, such as glucagon, somatostatin or pancreatic polypeptide. In some embodiments, the SC-β cells exhibit a low rate of replication. In some embodiments, the SC-β cells increase intracellular Ca2+ in response to glucose.

The terms "stem cell-derived α cell," "SC-α cell," "functional α cell," "functional pancreatic α cell," "mature SC-α cell," and their grammatical equivalents can refer to cells (e.g., non-native pancreatic α cells) that display at least one marker indicative of a pancreatic α cell (e.g., glucagon, expressing ISL1 but not NKX6.1), expresses glucagon, and secretes functional glucagon. In some embodiments, the "SC-α cell" does not express somatostatin. In some embodiments, the "SC-α cell" does not express insulin. In some embodiments, the terms "SC-α cell" and "non-native α cell" as used herein are interchangeable. In some embodiments, the "SC-α cell" comprises a mature pancreatic cell.

The terms "stem cell-derived δ cell," "SC-δ cell," "functional δ cell," "functional pancreatic δ cell," "mature SC-δ cell," and their grammatical equivalents can refer to cells (e.g., non-native pancreatic δ cells) that display at least one marker indicative of a pancreatic δ cell (e.g., somatostatin), expresses and secretes somatostatin. In some embodiments, "SC-δ cell" does not express glucagon. In some embodiments, "SC-δ cell" does not express insulin. In some embodiments, the terms "SC-δ cell" and "non-native δ cell" as used herein are interchangeable. In some embodiments, the "SC-δ cell" comprises a mature pancreatic cell.

The terms "stem cell-derived enterochromaffin (EC) cell," "SC-EC cell," and their grammatical equivalents can refer to cells (e.g., non-native pancreatic EC cells) that display at least one marker indicative of a pancreatic EC cell (e.g., VMAT1 (vesicular monoamine transporter 1), expressing NKX6.1 but not ISL1). In some embodiments, the terms "SC-EC cell" and "non-native EC cell" as used herein are interchangeable.

Similar to SC-β cells, it is to be understood that the SC-α, SC-δ cells, and SC-EC cells need not be derived (e.g., directly) from stem cells, as the methods of the disclosure are capable of deriving SC-α cells from other precursor cells generated during in vitro differentiation of SC-β cells as a starting point (e.g., one can use embryonic stem cells, induced-pluripotent stem cells, progenitor cells, partially reprogrammed somatic cells (e.g., a somatic cell which has been partially reprogrammed to an intermediate state between an induced pluripotent stem cell and the somatic cell from which it was derived), multipotent cells, totipotent cells, a transdifferentiated version of any of the foregoing cells, etc., as the invention is not intended to be limited in this manner).

As used herein, the term "insulin producing cell" and its grammatical equivalent refer to a cell differentiated from a pancreatic progenitor, or precursor thereof, which secretes insulin. An insulin-producing cell can include pancreatic β cell as that term is described herein, as well as pancreatic β-like cells (e.g., insulin-positive, endocrine cells) that synthesize (e.g., transcribe the insulin gene, translate the pro-insulin mRNA, and modify the proinsulin mRNA into the insulin protein), express (e.g., manifest the phenotypic trait carried by the insulin gene), or secrete (release insulin into the extracellular space) insulin in a constitutive or inducible manner A population of insulin producing cells e.g., produced by differentiating insulin-positive endocrine cells or a precursor thereof into SC-β cells according to the methods of the present disclosure can be pancreatic β cell or (β-like cells (e.g., cells that have at least one, or at least two least two) characteristic of an endogenous β cell and exhibit a glucose stimulated insulin secretion (GSIS) response that resembles an endogenous adult β cell. The population of insulin-producing cells, e.g. produced by the methods as disclosed herein can comprise mature pancreatic β cell or SC-β cells, and can also contain non-insulin-producing cells (e.g., cells of cell like phenotype with the exception they do not produce or secrete insulin).

The terms "insulin-positive β-like cell," "insulin-positive endocrine cell," and their grammatical equivalents can refer to cells (e.g., pancreatic endocrine cells) that displays at least one marker indicative of a pancreatic β cell and also expresses insulin but lack a glucose stimulated insulin secretion (GSIS) response characteristic of an endogenous β cell. Exemplary markers of "insulin-positive endocrine cell" include, but not limited to, NKX6.1 (NK6 homeobox 1), ISL1 (Islet1), and insulin. In some cases, the terms "insulin-positive endocrine cell" and "NKX6.1-positive, ISL1-positive cell" are used interchangeably.

The term "β cell marker" refers to, without limitation, proteins, peptides, nucleic acids, polymorphism of proteins and nucleic acids, splice variants, fragments of proteins or nucleic acids, elements, and other analyte which are specifically expressed or present in pancreatic β cells. Exemplary β cell markers include, but are not limited to, pancreatic and duodenal homeobox 1 (PDX1) polypeptide, insulin, c-peptide, amylin, E-cadherin, Hnf3β, PCI/3, B2, Nkx2.2, GLUT2, PC2, ZnT-8, ISL1, Pax6, Pax4, NeuroD, 1 Inf1b, Hnf-6, Hnf-3beta, and MafA, and those described in Zhang et al., Diabetes. 50(10):2231-6 (2001). In some embodiment, the β cell marker is a nuclear β-cell marker. In some embodiments, the β cell marker is PDX1 or PH3.

The term "pancreatic endocrine marker" can refer to without limitation, proteins, peptides, nucleic acids, polymorphism of proteins and nucleic acids, splice variants, fragments of proteins or nucleic acids, elements, and other analyte which are specifically expressed or present in pancreatic endocrine cells. Exemplary pancreatic endocrine cell markers include, but are not limited to, Ngn-3, NeuroD and Islet-1.

The term "pancreatic progenitor," "pancreatic endocrine progenitor," "pancreatic precursor," "pancreatic endocrine precursor" and their grammatical equivalents are used interchangeably herein and can refer to a stem cell which is capable of becoming a pancreatic hormone expressing cell capable of forming pancreatic endocrine cells, pancreatic exocrine cells or pancreatic duct cells. These cells are committed to differentiating towards at least one type of pancreatic cell, e.g. β cells that produce insulin; α cells that produce glucagon; δ cells (or D cells) that produce somatostatin; and/or F cells that produce pancreatic polypeptide. Such cells can express at least one of the following markers: NGN3, NKX2.2, NeuroD, ISL-1, Pax4, Pax6, or ARX.

The term "PDX1-positive pancreatic progenitor" as used herein can refer to a cell which is a pancreatic endoderm (PE) cell which has the capacity to differentiate into SC-β cells, such as pancreatic β cells. A PDX1-positive pancreatic progenitor expresses the marker PDX1. Other markers include, but are not limited to Cdcp1, or Ptf1a, or HNF6 or NRx2.2. The expression of PDX1 may be assessed by any method known by the skilled person such as immunochemistry using an anti-PDX1 antibody or quantitative RT-PCR. In some cases, a PDX1-positive pancreatic progenitor cell lacks expression of NKX6.1. In some cases, a PDX1-positive pancreatic progenitor cell can also be referred to as PDX1-positive, NKX6.1-negative pancreatic progenitor cell due to its lack of expression of NKX6.1. In some cases, the PDX1-positive pancreatic progenitor cells can also be termed as "pancreatic foregut endoderm cells."

The terms "PDX1-positive, NKX6.1-positive pancreatic progenitor," and "NKX6.1-positive pancreatic progenitor" are used interchangeably herein and can refer to a cell which is a pancreatic endoderm (PE) cell which has the capacity to differentiate into insulin-producing cells, such as pancreatic β cells. A PDX1-positive, NKX6.1-positive pancreatic progenitor expresses the markers PDX1 and NKX6-1. Other markers include, but are not limited to Cdcp1, or Ptf1a, or HNF6 or NRx2.2. The expression of NKX6-1 may be assessed by any method known by the skilled person such as immunochemistry using an anti-NKX6-1 antibody or quantitative RT-PCR. As used herein, the terms "NKX6.1" and "NKX6-1" are equivalent and interchangeable. In some cases, the PDX1-positive, NKX6.1-positive pancreatic progenitor cells can also be termed as "pancreatic foregut precursor cells."

The terms "NeuroD" and "NeuroD1" are used interchangeably and identify a protein expressed in pancreatic endocrine progenitor cells and the gene encoding it.

The term "epigenetics" refers to heritable changes in gene function that do not involve changes in the DNA sequence. Epigenetics most often denotes changes in a chromosome that affect gene activity and expression, but can also be used to describe any heritable phenotypic change that does not derive from a modification of the genome. Such effects on cellular and physiological phenotypic traits can result from external or environmental factors, or be part of normal developmental program. Epigenetics can also refer to functionally relevant changes to the genome that do not involve a change in the nucleotide sequence. Examples of mechanisms that produce such changes are DNA methylation and histone modification, each of which alters how genes are expressed without altering the underlying DNA sequence. Gene expression can be controlled through the action of repressor proteins that attach to silencer regions of the DNA. These epigenetic changes can last through cell divisions for the duration of the cell's life, and can also last for multiple generations even though they do not involve changes in the underlying DNA sequence of the organism. One example of an epigenetic change in eukaryotic biology is the process of cellular differentiation. During morphogenesis, totipotent stem cells become the various pluripotent cells, which in turn can become fully differentiated cells.

The term "epigenetic modifying compound" refers to a chemical compound that can make epigenetic changes genes, i.e., change gene expression(s) without changing DNA sequences. Epigenetic changes can help determine whether genes are turned on or off and can influence the production of proteins in certain cells, e.g., beta-cells. Epigenetic modifications, such as DNA methylation and histone modification, alter DNA accessibility and chromatin structure, thereby regulating patterns of gene expression. These processes are crucial to normal development and differentiation of distinct cell lineages in the adult organism. They can be modified by exogenous influences, and, as such, can contribute to or be the result of environmental alterations of phenotype or pathophenotype. Importantly, epigenetic modification has a crucial role in the regulation of pluripotency genes, which become inactivated during differentiation. Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

The term "differentiated cell" or its grammatical equivalents is meant any primary cell that is not, in its native form, pluripotent as that term is defined herein. Stated another way, the term "differentiated cell" can refer to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell leads to the pancreatic pathway, where ~98% of the cells become exocrine, ductular, or matrix cells, and ~2% become endocrine cells. Early endocrine cells are islet progenitors, which can then differentiate further into insulin-producing cells (e.g. functional endocrine cells) which secrete insulin, glucagon, somatostatin, or pancreatic polypeptide. Endoderm cells can also be differentiated into other cells of endodermal origin, e.g. lung, liver, intestine, thymus etc.

As used herein, the term "somatic cell" can refer to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for converting at least one insulin-positive endocrine cell or precursor thereof to an insulin-producing, glucose responsive cell can be performed both in vivo and in vitro (where in vivo is practiced when at least one insulin-positive endocrine cell or precursor thereof are present within a subject, and where in vitro is practiced using an isolated at least one insulin-positive endocrine cell or precursor thereof maintained in culture).

As used herein, the term "adult cell" can refer to a cell found throughout the body after embryonic development.

The term "endoderm cell" as used herein can refer to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of the respiratory and digestive tracts (e.g. the intestine), the liver and the pancreas.

The term "a cell of endoderm origin" as used herein can refer to any cell which has developed or differentiated from an endoderm cell. For example, a cell of endoderm origin includes cells of the liver, lung, pancreas, thymus, intestine, stomach and thyroid. Without wishing to be bound by theory, liver and pancreas progenitors (also referred to as pancreatic progenitors) are develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein can refer to a cell differentiated from an endoderm cell and which can be differentiated into a SC-β cell (e.g., a pancreatic β cell). A definitive endoderm cell expresses the marker Sox17. Other markers characteristic of definitive endoderm cells include, but are not limited to MIXL2, GATA4, HNF3b, GSC, FGF17, VWF, CALCR, FOXQ1, CXCR4, Cerberus, OTX2, goosecoid, C-Kit, CD99, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker PDX1 (e.g. they are PDX1-negative). Definitive endoderm cells have the capacity to differentiate into cells including those of the liver, lung, pancreas, thymus, intestine, stomach and thyroid. The expression of Sox17 and other markers of definitive endoderm may be assessed by any method known by the skilled person such as immunochemistry, e.g., using an anti-Sox17 antibody, or quantitative RT-PCR.

The term "pancreatic endoderm" can refer to a cell of endoderm origin which is capable of differentiating into multiple pancreatic lineages, including pancreatic β cells, but no longer has the capacity to differentiate into non-pancreatic lineages.

The term "primitive gut tube cell" or "gut tube cell" as used herein can refer to a cell differentiated from an endoderm cell and which can be differentiated into a SC-β cell (e.g., a pancreatic β cell). A primitive gut tube cell expresses at least one of the following markers: HNP1-β, HNF3-β or HNF4-α. In some cases, a primitive gut tube cell is FOXA2-positive and SOX2-positive, i.e., express both FOXA2 (also known as HNF3-β) and SOX2. In some cases, a primitive gut tube cell is FOXA2-positive and PDX1-negative, i.e., express FOXA2 but not PDX1. Primitive gut tube cells have the capacity to differentiate into cells including those of the lung, liver, pancreas, stomach, and intestine. The expression of HNF1-β and other markers of primitive gut tube may be assessed by any method known by the skilled person such as immunochemistry, e.g., using an anti-HNF1-β antibody.

The term "stem cell" as used herein, can refer to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" can refer to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retro-differentiation" by persons of ordinary skill in the art. As used herein, the term "pluripotent stem cell" includes embryonic stem cells, induced pluripotent stem cells, placental stem cells, etc.

The term "pluripotent" as used herein can refer to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g. iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and can refer to a pluripotent stem cell artificially derived (e.g., induced or by complete reversal) from a non-pluripotent cell, typically an adult somatic cell, for example, by inducing a forced expression of one or more genes.

The term "phenotype" can refer to one or a number of total biological characteristics that define the cell or organism under a particular set of environmental conditions and factors, regardless of the actual genotype.

The terms "subject," "patient," or "individual" are used interchangeably herein, and can refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject can refer to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g., dog, cat, horse, and the like, or production mammal, e g cow, sheep, pig, and the like. "Patient in need thereof" or "subject in need thereof" is referred to herein as a patient diagnosed with or suspected of having a disease or disorder, for instance, but not restricted to diabetes.

"Administering" used herein can refer to providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise the cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Some numerical values disclosed throughout are referred to as, for example, "X is at least or at least about 100; or 200 [or any numerical number]." This numerical value includes the number itself and all of the following:
  i) X is at least 100;
  ii) X is at least 200;
  iii) X is at least about 100; and
  iv) X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, "X is administered on or on about day 1 to 2; or 2 to 3 [or any numerical range]." This range includes the numbers themselves (e.g., the endpoints of the range) and all of the following:

i) X being administered on between day 1 and day 2;
ii) X being administered on between day 2 and day 3;
iii) X being administered on between about day 1 and day 2;
iv) X being administered on between about day 2 and day 3;
v) X being administered on between day 1 and about day 2;
vi) X being administered on between day 2 and about day 3;
vii) X being administered on between about day 1 and about day 2; and
viii) X being administered on between about day 2 and about day 3.

All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

In aspects, the present disclosure provides compositions and methods of differentiating pancreatic progenitor cells. The compositions and methods provided herein can, in some embodiments, offer pancreatic β cells, cell populations, or cell clusters that have high purity of pancreatic β cells, high insulin content, superior glucose-dependent insulin secretion response, as well as appropriate percentage of pancreatic α and δ cells and enterochromaffin cells, which can resemble native pancreatic islets both structurally and functionally.

In some aspects, provided herein is a method of differentiating pancreatic endocrine cells. In some cases, the method leads to generation of increased pancreatic β cells, increased pancreatic α cells, increased pancreatic δ cells, reduced enterochromaffin cells (EC cells), or any combination thereof. In some cases, the method results in generation of an in vitro cell composition comprising about 30%-40% pancreatic β cells, 30%-40% pancreatic α cells, 3-10% pancreatic δ cells, and/or less than 20% EC cells. In some cases, the cell composition generated according to the method disclosed herein has improved glucose-stimulated insulin secretion (GSIS) response as compared to cell compositions generated according to conventional methods. In some cases, the cell composition disclosed herein has dynamic GSIS response close to native pancreatic islets.

In some aspects, the methods provided herein take advantage of PKC activation during or after induction of NKX6.1 expression in PDX1-positive pancreatic progenitor cells, e.g., at the end stage of differentiating PDX1-positive pancreatic progenitor cells into PDX1-positive, NKX6.1-positive pancreatic progenitor cells. Without being bound by a certain theory, activation of PKC signaling in PDX1-positive, NKX6.1-positive pancreatic progenitor cells can affect the differentiation fate of certain cells, leading to increased percentage of pancreatic α cells and reduced percentage of EC cells.

In some aspects, the present disclosure provides a method that comprises: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and a γ-secretase inhibitor and one or more of a ROCK inhibitor, a growth factor from the TGFβ superfamily, a growth factor from the FGF family, a RA signaling pathway activator, and a SHH pathway inhibitor, thereby generating a second population of cells; and (c) contacting the second population of cells with a PKC activator, a γ-secretase inhibitor and one or more of a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells.

In some aspects, the present disclosure provides a method comprising: contacting a population of cells with a γ-secretase inhibitor and one or both of a growth factor from the TGFβ superfamily and a growth factor from the FGF family. In some embodiments, the population of cells comprises PDX1-positive cells. In some embodiments, the population of cells comprises PDX1-positive, NKX6.1-negative cells. In some embodiments, the population of cells comprises PDX1-positive, NKX6.1-positive cells.

In some aspects, the present disclosure provides a method comprising: (a) contacting a plurality of PDX1-positive, NKX6.1-negative pancreatic progenitor cells with one or more of a ROCK inhibitor, a growth factor from the TGFβ superfamily, a growth factor from the FGF family, a RA signaling pathway activator, and a SHH pathway inhibitor, for a period of no more than 1-5 days, thereby generating a first population of cells; (b) contacting the first population of cells with a γ-secretase inhibitor. In some embodiments, the contacting of step (a) is for a period of 4 or 5 days. In some embodiments, step (b) further comprises contacting the first population of cells with one or more of a PKC activator, a ROCK inhibitor, a growth factor from the TGFβ superfamily, a growth factor from the FGF family, a RA signaling pathway activator, and a SHH pathway inhibitor.

In some aspects, the present disclosure provides a method, comprising: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and one or more of a ROCK inhibitor, a growth factor from the TGFβ superfamily, a growth factor from the FGF family, a RA signaling pathway activator, and a SHH pathway inhibitor, thereby generating a second population of cells; wherein the PKC activator is a benzolactam-derivative; and (c) contacting the second population of cells with the PKC activator, a γ-secretase inhibitor and one or more of a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells. In some cases, the benzolactam-derivative is TPPB.

In some aspects, the present disclosure provides a method that comprises: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and one or more of a ROCK inhibitor, a growth factor from the TGFβ superfamily, a growth factor from the FGF family, a RA signaling pathway activator, and a SHH pathway inhibitor, thereby generating a second population of cells; (c) contacting the second population of cells with a PKC activator and one or more of a γ-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells; (d) contacting the third population of cells with one or more of a TGF-β signaling pathway inhibitor, a RA signaling pathway activator, a TH signaling pathway activator, a protein kinase inhibitor, a ROCK inhibitor, a BMP signaling pathway inhibitor, and an epigenetic modifying compound, thereby generating a fourth population of cells; and (e) contacting the fourth population of cells with a PKC activator and one or more of a serum albumin protein, vitamin C, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound, thereby generating a fifth population of cells.

In some aspects, the method disclosed herein comprises differentiating PDX1-positive pancreatic progenitor cells into PDX1-positive, NKX6.1-positive pancreatic progenitor cells by contacting said PDX1-positive pancreatic progenitor cells with a ROCK inhibitor, a growth factor from TGFβ superfamily, a growth factor from FGF family, a RA signaling pathway activator, and a SHH pathway inhibitor, thereby generating a population of cells comprising PDX1-positive, NKX6.1-positive pancreatic progenitor cells. In some cases, the method comprises contacting the population of cells comprising PDX1-positive, NKX6.1-positive pancreatic progenitor cells with a first composition comprising a PKC activator, a γ-secretase inhibitor, a ROCK inhibitor, a growth factor from TGFβ superfamily, a growth factor from FGF family, a RA signaling pathway activator, and a SHH pathway inhibitor, for a first time period. In some cases, the method comprises after the first time period, contacting the population of cells comprising PDX1-positive, NKX6.1-positive pancreatic progenitor cells with a second composition comprising the PKC activator, the γ-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, for a second time period. In some cases, the method comprises after the second time period, contacting the population of cells comprising PDX1-positive, NKX6.1-positive pancreatic progenitor cells with a third composition that differentiates at least some of the PDX1-positive, NKX6.1-positive pancreatic progenitor cells into NKX6.1-positive, ISL1-positive endocrine cells, thereby generating a population of cells comprising NKX6.1-positive, ISL1-positive endocrine cells.

In some cases, provided herein is an in vitro composition comprising a cell population, wherein the cell population comprises: (a) at least about 35% cells expressing C-peptide and not expressing VMAT1; and (b) at most about 35% cells expressing VMAT1, or at least about 15% cells expressing glucagon (e.g., as measured by flow cytometry). In some aspects, the disclosure provides a composition that comprises an in vitro cell population, wherein said cell population comprises: at least about 35% cells expressing C-peptide and not expressing VMAT1; and (i) at most about 35% cells expressing VMAT1, and/or (ii) at least about 15% cells expressing glucagon. In some embodiments, the percentages of cells are measured by flow cytometry. In some cases, said cell population comprises at most about 30% cells expressing VMAT1 and at least about 20% cells expressing glucagon.

In some cases, provided herein is an in vitro composition, comprising PDX1-positive, NKX6.1-positive pancreatic progenitor cells; NKX6.1-positive, ISL1-positive endocrine cells; and a PKC activator; wherein the PKC activator is a benzolactam derivative.

In some cases, provided herein is a composition comprising a population of cells, wherein: (a) 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the population of cells express C-peptide and ISL1 but not VMAT1; (b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and/or (c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

In some cases, provided herein is a composition comprising a population of cells, wherein: (a) 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the population of cells express C-peptide and ISL1 but not VMAT1; (b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and (c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

In some cases, the methods provided herein include PKC activation when differentiating PDX1-positive, NKX6.1-positive pancreatic progenitor cells into NKX6.1-positive, ISL1-positive endocrine cells. For instance, PKC activator can be introduced at an early stage of a time period when PDX1-positive, NKX6.1-positive pancreatic progenitor cells are contacted with differentiation factors that direct the differentiation of the PDX1-positive, NKX6.1-positive pancreatic progenitor cells into NKX6.1-positive, ISL1-positive endocrine cells. In some cases, the method comprises (a) contacting a population of cells comprising PDX1-positive, NKX6.1-positive pancreatic progenitor cells with a first composition comprising the PKC activator, a ROCK inhibitor, a growth factor from TGFβ superfamily, a growth factor from FGF family, a RA signaling pathway activator, and a SHH pathway inhibitor, for one to two days, thereby obtaining a first transformation cell population comprising PDX1-positive, NKX6.1-positive pancreatic progenitor cells; and (b) contacting the first transformation cell population comprising PDX1-positive, NKX6.1-positive pancreatic progenitor cells with a second composition comprising the PKC activator, a TGF-β signaling pathway inhibitor, a thyroid hormone signaling pathway activator, and an epigenetic modifying compound, for one to two days, thereby obtaining a second transformation cell population comprising NKX6.1-positive, ISL1-positive endocrine cells.

Methods of Generating Endocrine Cells

In aspects, the present disclosure relates to compositions and methods of generating endocrine cells from pancreatic progenitor cells or precursors. Certain exemplary detailed protocols of generating endocrine cells to provide at least one SC-β cell are described in U.S. Patent Application Publication No. US20150240212 and US20150218522, each of which is herein incorporated by reference in its entirety.

In some cases, the method of generating a population of endocrine cells leads to increased percentage of pancreatic α and/or β cells and decreased percentage of pancreatic EC cells when generating pancreatic β cells. In some embodiments, the methods disclosed herein may be used to obtain an enriched population of α cells. In some embodiments, the methods disclosed herein may be used to obtain an enriched population of δ cells. In some cases, a method for generating a population of endocrine cells comprises (a) contacting a population of cells comprising PDX1-positive, NKX6.1-positive pancreatic progenitor cells with a PKC activator for a first time period; and (b) after the first time period, contacting the population of cells comprising PDX1-positive, NKX6.1-positive pancreatic progenitor cells with a composition comprising a TGF-β signaling pathway inhibitor, a thyroid hormone signaling pathway activator, and an epigenetic modifying compound, thereby generating a population of cells comprising pancreatic endocrine cells. In some cases, the population of cells generated according to the method disclosed herein has: (i) an increased proportion of cells expressing somatostatin; (ii) an increased proportion of cells expressing glucagon; (iii) a reduced proportion of cells expressing VMAT1; or (iv) an increased proportion of cells expressing C-peptide, as compared to a corresponding population of cells which is generated without contacting of the PDX1-positive, NKX6.1-positive pancreatic progenitor cells with the PKC activator for the first time period.

In some cases, the method includes contacting the population of cells comprising PDX1-positive, NKX6.1-positive pancreatic progenitor cells with a first composition comprising a PKC activator, a γ-secretase inhibitor, and a factor selected from the group consisting of: a ROCK inhibitor, a growth factor from TGFβ superfamily, a growth factor from FGF family, a RA signaling pathway activator, and a SHH pathway inhibitor, for a first time period; after the first time period, contacting the population of cells comprising PDX1-positive, NKX6.1-positive pancreatic progenitor cells with a second composition comprising the PKC activator, the γ-secretase inhibitor, and a factor selected from the group consisting of: a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, for a second time period. In some cases, the first composition comprises PKC activator, a γ-secretase inhibitor, a ROCK inhibitor, a growth factor from TGFβ superfamily, a growth factor from FGF family, a RA signaling pathway activator, and a SHH pathway inhibitor. In some cases, the second composition comprises the PKC activator, the γ-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound.

In some cases, the composition that differentiates at least some of the PDX1-positive, NKX6.1-positive pancreatic progenitor cells into NKX6.1-positive, ISL1-positive endocrine cells comprises a differentiation factor selected from the group consisting of: a TGF-β signaling pathway inhibitor, a thyroid hormone signaling pathway activator, an epigenetic modifying compound, a growth factor from EGF family, a RA signaling pathway activator, a SHH pathway inhibitor, a γ-secretase inhibitor, a protein kinase inhibitor, a ROCK inhibitor, and a BMP signaling pathway inhibitor. In some cases, the composition comprises a TGF-β signaling pathway inhibitor, a thyroid hormone signaling pathway activator, an epigenetic modifying compound, a growth factor from EGF family, a RA signaling pathway activator, a SHH pathway inhibitor, a γ-secretase inhibitor, a protein kinase inhibitor, a ROCK inhibitor, and a BMP signaling pathway inhibitor.

In some cases, the method further comprises contacting PDX1-positive, NKX6.1-positive pancreatic progenitor cells with a composition comprising a PKC activator. For instance, the method comprises: (a) contacting a population of cells comprising PDX1-positive, NKX6.1-positive pancreatic progenitor cells with a first composition comprising the PKC activator, a ROCK inhibitor, a growth factor from TGFβ superfamily, a growth factor from FGF family, a RA signaling pathway activator, and a SHH pathway inhibitor, for one to two days, thereby obtaining a first transformation cell population comprising PDX1-positive, NKX6.1-positive pancreatic progenitor cells; and (b) contacting the first transformation cell population comprising PDX1-positive, NKX6.1-positive pancreatic progenitor cells with a second composition comprising the PKC activator, a TGF-β signaling pathway inhibitor, a thyroid hormone signaling pathway activator, and an epigenetic modifying compound, for one to two days, thereby obtaining a second transformation cell population comprising NKX6.1-positive, ISL1-positive endocrine cells. In some cases, the method further comprises contacting the second transformation cell population with a composition comprising a TGF-β signaling pathway inhibitor, a thyroid hormone signaling pathway activator, and an epigenetic modifying compound, thereby generating a population of cells comprising pancreatic endocrine cells.

In some cases, the population of cells comprising pancreatic endocrine cells generated according to the method provided herein comprises: at least about 4% cells expressing somatostatin, at least about 15% cells expressing glucagon, at most about 35% cells expressing VMAT1, or at least about 40% cells expressing C-peptide, as measured by flow cytometry. In some cases, the population of cells comprising pancreatic endocrine cells comprises: at least about 50% more cells expressing somatostatin, at least about 50% more cells expressing glucagon, at least about 20% fewer cells expressing VMAT1, or at least about 10% more cells expressing C-peptide, as compared to a corresponding population of cells which is generated without contacting with the PKC activator. In some cases, the population of cells comprising pancreatic endocrine cells comprises: at least about 100% more cells expressing somatostatin, at least about 200% more cells expressing glucagon, at least about 50% fewer cells expressing VMAT1, or at least about 20% more cells expressing C-peptide, as compared to a corresponding population of cells which is generated without contacting with the PKC activator.

In some aspects, the present disclosure provides for method that comprises contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells. In some cases, the method further comprises contacting the first population of cells with a PKC activator and a γ-secretase inhibitor and one or more of a ROCK inhibitor, a growth factor from the TGFβ superfamily, a growth factor from the FGF family, a RA signaling pathway activator, and a SHH pathway inhibitor, thereby generating a second population of cells. In some cases, the method further comprises contacting the second population of cells with a PKC activator, a γ-secretase inhibitor and one or more of a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells. In some cases, the method comprises: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and a γ-secretase inhibitor and one or more of a ROCK inhibitor, a growth factor from the TGFβ superfamily, a growth factor from the FGF family, a RA signaling pathway activator, and a SHH pathway inhibitor, thereby generating a second population of cells; and (c) contacting the second population of cells with a PKC activator, a γ-secretase inhibitor and one or more of a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells. In some cases, the method further comprises: (d) contacting the third population of cells with one or more of a serum albumin protein, vitamin C, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound, thereby generating a fourth population of cells. In some cases, step (d) comprises contacting the third population of cells with a PKC activator.

In some aspects, the present disclosure provides a method that comprises: (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and one or more of a ROCK inhibitor, a growth factor from the TGFβ superfamily, a growth factor from the FGF family, a RA signaling pathway activator, and a SHH pathway inhibitor, thereby generating a second population of cells; wherein the PKC activator is a benzolactam-derivative; and (c) contacting the second population of cells with a the PKC activator, a γ-secretase inhibitor, and one or more of a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells. In some cases, the benzolactam-derivative is TPPB. In some cases, the step (b) for generating the second population of cells comprises contacting the first population of cells with a γ-secretase inhibitor. In some cases, the method further comprises (d) contacting the third population of cells with one or more of a TGF-β signaling pathway inhibitor, a RA signaling pathway activator, a TH signaling pathway activator, a protein kinase inhibitor, a ROCK inhibitor, a BMP signaling pathway inhibitor, and an epigenetic modifying compound, thereby generating a fourth population of cells. In some cases, step (d) for generating the fourth population of cells does not comprise contacting the third population of cells with a PKC activator. In some cases, step (d) for generating the fourth population of cells does not comprise contacting the third population of cells with a γ-secretase inhibitor. In some cases, step (d) for generating the fourth population of cells does not comprise contacting the third population of cells with a SHH pathway inhibitor. In some cases, step (d) for generating the fourth population of cells does not comprise contacting the third population of cells with a growth factor from EGF family.

In some cases, the method further comprises: (e) contacting the fourth population of cells with one or more of a serum albumin protein, vitamin C, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound, thereby generating a fifth population of cells. In some cases, step (e) comprises contacting the fourth population of cells with a PKC activator.

In some aspects, the present disclosure provides a method that comprises (a) contacting a plurality of PDX1-positive, NKX6.1-negative pancreatic progenitor cells with one or more of a ROCK inhibitor, a growth factor from TGFβ superfamily, a growth factor from FGF family, a RA signaling pathway activator, and a SHH pathway inhibitor, thereby generating a first population of cells; (b) contacting the first population of cells with a PKC activator and one or more of a ROCK inhibitor, a growth factor from the TGFβ superfamily, a growth factor from the FGF family, a RA signaling pathway activator, and a SHH pathway inhibitor, thereby generating a second population of cells; (c) contacting the second population of cells with a PKC activator and one or more of a γ-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound, thereby generating a third population of cells; (d) contacting the third population of cells with one or more of a TGF-β signaling pathway inhibitor, a RA signaling pathway activator, a TH signaling pathway activator, a protein kinase inhibitor, a ROCK inhibitor, a BMP signaling pathway inhibitor, and an epigenetic modifying compound, thereby generating a fourth population of cells; and (e) contacting the fourth population of cells with a PKC activator and one or more of a serum albumin protein, vitamin C, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound, thereby generating a fifth population of cells. In some cases, the step (d) of the method provided herein comprises contacting the fourth population of cells with a serum albumin protein.

In some cases, step (a) for generating the first population of cells in the method disclosed herein is performed over the course of about 1, 2, 3, 4, 5 or 6 days. In some cases, step (a) for generating the first population of cells is performed over the course of 3-5 days, for instance 3-4 days, 4-5 days, about 3 days, about 4 days, or about 5 days. In some cases, the step (a) for generating the first population of cells is performed over the course of 4 days. In some cases, step (b) for generating the second population of cells in the method disclosed herein is performed over the course of 1, 2, 3 or 4 days. In some cases, step (b) for generating the second population of cells is performed over the course of 1-3 days, for instance, 1-2 days, 2-3 days, about 1 day, about 2 days, or about 3 days. In some cases, step (b) for generating the second population of cells is performed over the course of 2 days. In some cases, step (c) for generating the third population of cells in the method disclosed herein is performed over the course of 1, 2, 3, or 4 days. In some cases, step (c) for generating the third population of cells is performed over the course of 1-3 days, for instance, 1-2 days, 2-3 days, about 1 day, about 2 days, or about 3 days. In some cases, step (c) for generating the third population of cells is performed over the course of 2 days. In some cases, step (d) for generating the fourth population of cells in the method disclosed herein is performed over the course of 1, 2, 3, 4, 5, 6, or 7 days. In some cases, step (d) for generating the fourth population of cells is performed over the course of 4-6 days, for instance 5-6 days, 4-5 days, about 4 days, about 5 days, or about 6 days. In some cases, step (d) for generating the fourth population of cells is performed over the course of 5 days. In some cases, step (e) for generating the fifth population of cells in the method disclosed herein is performed over the course of 1, 2, 3, 4, 5, 6, 7, 8, 9, 10, 11, 12, 13, 14, or 15 days. In some cases, step (d) for generating the fourth population of cells is performed over the course of 10-12 days, for instance, 10-11 days, 11-12 days, about 10 days, about 11 days, about 12 days.

In some cases, the second population of cells comprises PDX1-positive and NKX6.1-positive cells. In some cases, the fourth population of cells comprises PDX1-positive, NKX6.1-positive, ISL1-positive cells. In some cases, the fifth population of cells comprises cells that express C-peptide and ISL1 but not VMAT1. In some cases, 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the fourth population of cells express C-peptide and ISL1 but not VMAT1. In some cases, 40-60% of the cells in the fourth population of cells express C-peptide and ISL1 but not VMAT1. In some cases, the fourth population of cells comprises cells that express glucagon but not somatostatin. In some cases, 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the fourth population of cells express glucagon but not somatostatin. In some cases, 10-25% of the cells in the fourth population of cells express somatostatin but not glucagon. In some cases, the fourth population of cells comprises cells that express somatostatin but not glucagon. In some cases, 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the fourth population of cells express somatostatin but not glucagon.

In some cases, the step of generating the first population of cells in the method provided herein comprises contacting a plurality of PDX1-positive, NKX6.1-negative pancreatic progenitor cells with a ROCK inhibitor, a growth factor from TGFβ superfamily, a growth factor from FGF family, a RA signaling pathway activator, and a SHH pathway inhibitor. In some cases, the step of generating the second population of cells in the method provided herein comprises contacting the first population of cells with a ROCK inhibitor, a growth factor from the TGFβ superfamily, a growth factor from the FGF family, a RA signaling pathway activator, and a SHH pathway inhibitor. In some cases, the step of generating the third population of cells in the method provided herein comprises contacting the second population of cells with a gamma-secretase inhibitor, a TGF-β signaling pathway inhibitor, a growth factor from EGF family, a RA signaling pathway activator, a SHH pathway inhibitor, a TH signaling pathway activator, a protein kinase inhibitor, a ROCK inhibitor, a BMP signaling pathway inhibitor, and an epigenetic modifying compound. In some cases, the step of generating the fourth population of cells in the method provided herein comprises contacting the third population of cells with serum albumin protein, a TGF-β signaling pathway inhibitor, a SHH pathway inhibitor, a TH signaling pathway activator, a protein kinase inhibitor, a ROCK inhibitor, a BMP signaling pathway inhibitor, and an epigenetic modifying compound. In some cases, the ROCK inhibitor for use in the method provided herein is thiazovavin. In some cases, the growth factor from the TGFβ superfamily for use in the steps of generating the first population of cells and/or the second population of cells in the method provided herein is activin A. In some cases, the growth factor from the FGF family for use in the steps of generating the first population of cells and/or the second population of cells in the method provided herein is KGF. In some cases, the RA signaling pathway activator for use in the steps of generating the first population of cells, the second population of cells, and/or the third population of cells in the method provided herein is retinoic acid. In some cases, the SHH pathway inhibitor for use in the steps of generating the first population of cells, the second population of cells, and/or the third population of cells in the method provided herein is Sant-1. In some cases, the PKC activator for use in the steps of generating the second population of cells, the third population of cells, and/or the fourth population of cells in the method provided herein is selected from the group consisting of: phorbol 12,13-dibutyrate (PDBU), FR 236924, Prostratin, SC-9, and TPPB. In some cases, the PKC activator is PDBU. In some cases, the γ-secretase inhibitor for use in the steps of generating the second population of cells, and/or the third population of cells in the method provided herein is XXI. In some cases, the TGF-β signaling pathway inhibitor for use in the steps of generating the third population of cells, and/or the fourth population of cells in the method provided herein is ALK5i. In some cases, the growth factor from the EGF family for use in the steps of generating the third population of cells in the method provided herein is betacellulin. In some cases, the TH signaling pathway activator for use in the steps of generating the third population of cells and/or the fourth population of cells in the method provided herein is T3, GC-1 or a thyroid hormone derivative. In some cases, the protein kinase inhibitor for use in the steps of generating the third population of cells, and/or the fourth population of cells in the method provided herein is staurosporine. In some cases, the BMP signaling pathway inhibitor for use in the steps of generating the third population of cells, and/or the fourth population of cells in the method provided herein is LDN193189 or DMH-1. In some cases, the epigenetic modifying compound for use in the steps of generating the third population of cells, and/or the fourth population of cells in the method provided herein is DZNep.

In some cases, the first time period during which the pancreatic progenitor cells are treated with PKC activator is at least two days, three days, or four days. In some cases, the first time period is at most four days, three days, or two days. In some cases, the first time period is from two to four days. In some cases, the second time period during which the pancreatic progenitor cells are treated with PKC activator is at least two days. In some cases, the second time period is at most four days. In some cases, the second time period is from two to four days. In some cases, treatment of PKC activator as discussed herein during the transition between differentiation of PDX1-positive, NKX6.1-positive pancreatic progenitor cells and differentiation of NKX6.1-positive, ISL1-positive endocrine cells is for at least two days, three days, or four days. In some cases, treatment of PKC activator as discussed herein during the transition between differentiation of PDX1-positive, NKX6.1-positive pancreatic progenitor cells and differentiation of NKX6.1-positive, ISL1-positive endocrine cells is for at most two days, three days, or four days. In some cases, treatment of PKC activator as discussed herein during the transition between differentiation of PDX1-positive, NKX6.1-positive pancreatic progenitor cells and differentiation of NKX6.1-positive, ISL1-positive endocrine cells is for from two days to four days.

In some embodiments, a PKC activator is contacted to a population of differentiating cells at two or more different time points during the differentiation process. In some embodiments, the PKC activator is contacted to a population of cells, wherein the cells comprise PDX1-positive, NKX6.1-negative cells. In some embodiments, the PKC activator is contacted to a population of cells, wherein the cells comprise PDX1-positive, NKX6.1-positive cells. In some embodiments, the PKC activator is contacted to a population of cells, wherein the cells comprise insulin-positive cells. In some embodiments, the PKC activator is contacted to a population of cells at each of the following differentiation stages: when the cells comprise PDX1-positive, NKX6.1-negative cells; when the cells comprise PDX1-positive, NKX6.1-positive cells; and when the cells comprise insulin-positive cells. In some embodiments, the same type of PKC activator (e.g., a phorbol ester or benzolactam-derivative) is administered to the different population of cells at the two or more different time points. For example, in some embodiments, a phorbol ester (e.g., PDBU) is administered to a cell population comprising PDX1-positive, NKX6.1-negative cells, and a phorbol ester (e.g., PDBU) is administered to a cell population comprising PDX-positive, NKX6.1-positive cells during the same differentiation protocol. In some embodiments, one or more different PKC activators (e.g., a phorbol ester and a benzolactam-derivative) are administered to the different population of cells at the two or more different time points. For example, in some embodiments, a phorbol ester (e.g., PDBU) is administered to a cell population comprising PDX1-positive, NKX6.1-negative cells, and a benzolactam derivative (e.g., TPPB) is administered to a cell population comprising PDX-positive, NKX6.1-positive cells during the same differentiation protocol.

In some cases, non-limiting examples of the PKC activator of the method described herein include phorbol 12,13-dibutyrate (PDBU), FR 236924, Prostratin, SC-9, and TPPB. In some cases, the PKC activator comprises PDBU. In some cases, the PKC activator comprises TPPB. In some cases, the PKC activator is contacted to the population of cells comprising PDX1-positive, NKX6.1-positive pancreatic progenitor cells at a concentration from 50 nM to 2000 nM, from 75 nM to 1500 nM, from 100 nM to 1000 nM, from 200 nM to 750 nM, or from 400 nM to 600 nM. In some cases, the PKC activator is at a concentration from 100 nM to 1000 nM. In some cases, the PKC activator is at a concentration at least about 100 nM, 200 nM, 300 nM, 400 nM, 500 nM, 600 nM, 700 nM, 800 nM, 900 nM, or 1000 nM. In some cases, the PKC activator is at a concentration at most about 100 nM, 200 nM, 300 nM, 400 nM, 500 nM, 600 nM, 700 nM, 800 nM, 900 nM, or 1000 nM. In some cases, the PKC activator is at a concentration about 100 nM, 200 nM, 300 nM, 400 nM, 500 nM, 600 nM, 700 nM, 800 nM, 900 nM, or 1000 nM. In some cases, the PKC activator is at a concentration about 500 nM.

In some cases, non-limiting examples of the gamma secretase inhibitor used in the methods described herein include XXI and DAPT. In some cases, the gamma secretase inhibitor comprises XXI. In some cases, the gamma secretase inhibitor is contacted to the population of cells comprising PDX1-positive, NKX6.1-positive pancreatic progenitor cells at a concentration from 0.2 µM to 20 µM, from 0.3 µM to 15 µM, or from 0.5 µM to 10 µM, from 1 µM to 5 µM, or from 1.5 µM to 2.5 µM. In some cases, the gamma secretase inhibitor is at a concentration about 0.5 µM, 0.75 µM, 1 µM, 1.25 µM, 1.5 µM, 1.75 µM, 2 µM, 2.25 µM, 2.5 µM, 3 µM, 4 µM, 5 µM, 7.5 µM, 10 µM, 15 µM, or 20 µM. In some cases, the gamma secretase inhibitor is at a concentration at least about 0.5 µM, 0.75 µM, 1 µM, 1.25 µM, 1.5 µM, 1.75 µM, 2 µM, 2.25 µM, 2.5 µM, 3 µM, 4 µM, or 5 µM. In some cases, the gamma secretase inhibitor is at a concentration at most about 1 µM, 1.25 µM, 1.5 µM, 1.75 µM, 2 µM, 2.25 µM, 2.5 µM, 3 µM, 4 µM, 5 µM, 7.5 µM, 10 µM, 15 µM, or 20 µM.

Cell Compositions

In some aspects, provided herein are cell compositions that include SC-β cells, SC-α cells, SC-δ cells, and SC-EC cells. In some cases, the cell compositions provided herein have desirable amount (e.g., percentage) of SC-β cells, SC-α cells, and SC-δ cells, and limited amount of SC-EC cells. In some cases, the cell constituent of the cell compositions resembles a native pancreatic islet.

In some cases, the SC-β cells of the disclosure share many characteristic features of β cells which are important for normal β cell function. In some embodiments, the SC-β cell exhibits a glucose stimulated insulin secretion (GSIS) response in vitro. In some embodiments, the SC-β cell exhibits a GSIS response in vivo. In some embodiments, the SC-β cell exhibits in vitro and in vivo GSIS responses. In some embodiments, the GSIS responses resemble the GSIS responses of an endogenous mature pancreatic β cell. In some embodiments, the SC-β cell exhibits a GSIS response to at least one glucose challenge. In some embodiments, the SC-β cell exhibits a GSIS response to at least two sequential glucose challenges. In some embodiments, the SC-β cell exhibits a GSIS response to at least three sequential glucose challenges. In some embodiments, the GSIS responses resemble the GSIS response of endogenous human islets to multiple glucose challenges. In some embodiments, the GSIS response is observed immediately upon transplanting the cell into a human or animal. In some embodiments, the GSIS response is observed within approximately 24 hours of transplanting the cell into a human or animal. In some embodiments, the GSIS response is observed within approximately one week of transplanting the cell into a human or animal. In some embodiments, the GSIS response is observed within approximately two weeks of transplanting the cell into a human or animal. In some embodiments, the stimulation index of the cell as characterized by the ratio of insulin secreted in response to high glucose concentrations compared to low glucose concentrations is similar to the stimulation index of an endogenous mature pancreatic β cell. In some embodiments, the SC-β cell exhibits a stimulation index of greater than 1. In some embodiments, the SC-β cell exhibits a stimulation index of greater than or equal to 1. In some embodiments, the SC-β cell exhibits a stimulation index of greater than 1.1. In some embodiments, the SC-β cell exhibits a stimulation index of greater than or equal to 1.1. In some embodiments, the SC-β cell exhibits a stimulation index of greater than 2. In some embodiments, the SC-β cell exhibits a stimulation index of greater than or equal to 1. In some embodiments, the SC-β cell exhibits a stimulation index of at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 or greater.

In some embodiments, the disclosure provides for an in vitro composition, comprising PDX1-positive, NKX6.1-positive pancreatic progenitor cells; a PKC activator; and a γ-secretase inhibitor. In some embodiments, the disclosure provides for an in vitro composition, comprising NKX6.1-positive, ISL1-positive endocrine cells; a PKC activator; and a γ-secretase inhibitor. In some embodiments, the disclosure provides for an in vitro composition, comprising PDX1-positive, NKX6.1-positive pancreatic progenitor cells; NKX6.1-positive, ISL1-positive endocrine cells; a PKC activator; and a γ-secretase inhibitor. In some embodiments, the PKC activator is selected from the group consisting of: phorbol 12,13-dibutyrate (PDBU), FR 236924, Prostratin, SC-9, and TPPB. In some embodiments, the γ-secretase inhibitor is DAPT or XXI.

In some aspects, the present disclosure provides an in vitro composition that comprises PDX1-positive, NKX6.1-negative pancreatic progenitor cells; PDX1-positive, NKX6.1-positive pancreatic progenitor cells; a PKC activator; and a γ-secretase inhibitor. In some embodiments, at least 10%, 20%, 30%, 40%, 50%, 60%, 70%, 80%, or 90% of the cells in the composition are PDX1-positive, NKX6.1-positive pancreatic progenitor cells. In some embodiments, less than 90%, 80%, 70%, 60%, 50%, 40%, 30%, 20%, or 10% of the cells in the composition are PDX1-positive, NKX6.1-negative pancreatic progenitor cells. In some embodiments, the PKC activator is selected from the group consisting of: phorbol 12,13-dibutyrate (PDBU), FR 236924, Prostratin, SC-9, and TPPB. In some embodiments, the γ-secretase inhibitor is DAPT or XXI. In some embodiments, the composition further comprises a growth factor from the FGF family. In some embodiments, the growth factor from the FGF family is KGF. In some embodiments, the composition further comprises a growth factor of the TGFβ superfamily. In some embodiments, the growth factor of the TGFβ superfamily is activin A.

In some aspects, the present disclosure provides an in vitro composition comprising PDX1-positive cells, a γ-secretase inhibitor, and one or both of a growth factor from the TGFβ superfamily and a growth factor from the FGF family. In some embodiments, the composition of cells comprises PDX1-positive, NKX6.1-negative cells. In some embodiments, the composition of cells comprises PDX1-positive, NKX6.1-positive cells. In some embodiments, the composition further comprises any one of or combination of a PKC activator, a growth factor from the FGF family, a ROCK inhibitor, a growth factor from the TGFβ superfamily, a sonic hedgehog pathway inhibitor, and a retinoic acid signaling pathway activator.

In some aspects, the present disclosure provides an in vitro composition comprising PDX1-positive, NKX6.1-negative pancreatic progenitor cells; PDX1-positive, NKX6.1-positive pancreatic progenitor cells; and a γ-secretase inhibitor. In some embodiments, the γ-secretase inhibitor is XXI. In some embodiments, the γ-secretase inhibitor is DAPT.

In some embodiments, at least 10%, at least 20%, at least 30%, at least 40%, at least 50%, at least 60%, at least 70%, at least 80%, or at least 90% of the cells in the composition are PDX1-positive, NKX6.1-positive pancreatic progenitor cells. In some embodiments, less than 90%, less than 80%, less than 70%, less than 60%, less than 50%, less than 40%, less than 30%, less than 20%, or less than 10% of the cells in the composition are PDX1-positive, NKX6.1-negative pancreatic progenitor cells.

In some embodiments, the composition further comprises a growth factor from the FGF family. In some embodiments, the composition further comprises a sonic hedgehog pathway inhibitor. In some embodiments, the composition further comprises a ROCK inhibitor. In some embodiments, the composition further comprises a growth factor from the TGFβ superfamily. In some embodiments, the composition further comprises a retinoic acid signaling pathway activator. In some embodiments, the composition further comprises a PKC activator.

In some embodiments, the composition further comprises two or more (e.g., any two, any three, any four, any five, or any six) of a PKC activator, a growth factor from the FGF family, a ROCK inhibitor, a growth factor from the TGFβ superfamily, a sonic hedgehog pathway inhibitor, and a retinoic acid signaling pathway activator. In some embodiments of the composition, the growth factor from the FGF family is KGF. In some embodiments, the sonic hedgehog pathway inhibitor is SANT-1. In some embodiments, the ROCK inhibitor is thiazovivin. In some embodiments, the growth factor from the TGFβ superfamily is activin A. In some embodiments, the retinoic acid signaling pathway activator is retinoic acid. In some embodiments, the PKC activator is PDBU.

In some aspects, the present disclosure provides a population of in vitro differentiated cells comprising NKX6.1-positive, ISL1-positive cells and NKX6.1-negative, ISL1-positive cells. In some embodiments, the population comprises more NKX6.1-negative, ISL1-positive cells than NKX6.1-positive, ISL1-positive cells. In some embodiments, at least 73% of the cells in the population are ISL1-positive cells. In some embodiments, at least 40% of the cells in the population are NKX6.1-negative, ISL1-positive cells. In some embodiments, less than 12% of the cells in the population are NKX6.1-negative, ISL1-negative cells.

In some aspects, the present disclosure provides a population of in vitro differentiated cells comprising NKX6.1-positive, ISL1-positive cells and NKX6.1-negative, ISL1-positive cells, where less than 12% of the cells (e.g., about 11%, about 10%, about 9%, about 8%, about 7%, about 6%, about 5%, about 4%, about 3%, about 2%, about 1%, or less) in the population are NKX6.1-negative, ISL1-negative cells. In some embodiments, less than 10%, less than 8%, less than 6%, less than 4%, 1-11%, 2-10%, 2-12%, 4-12%, 6-12%, 8-12%, 2-8%, 4-8%, 3-6% or 3-5% of the cells in the population are NKX6.1-negative, ISL1-negative cells. In some embodiments, 2-12%, 4-12%, 6-12%, 8-12%, 2-8%, 4-8%, 3-6% or 3-5% of the cells in the population are NKX6.1-negative, ISL1-negative cells.

In some embodiments, at least 60%, at least 65%, at least 70%, at least 73%, at least 74%, at least 75%, at least 80%, at least 85%, at least 90%, about 85-95%, or about 90-95% of the cells in the population are ISL1-positive cells. In some embodiments, 50-90%, 50-85%, 50-80%, 50-75%, 50-70%, 50-60%, 60-90%, 60-85%, 60-80%, 60-75%, 60-70%, 65-90%, 65-85%, 65-80%, 65-75%, 65-70%, 70-90%, 70-85%, 70-80%, 70-75%, 75-90%, 75-85%, 75-80%, 80-90%, 80-85%, or 85-90% of the cells in the population are ISL1-positive cells. In some embodiments, at least 74%, at least 75%, at least 80%, at least 85%, at least 90%, about 85-95%, or about 90-95% of the cells in the population are ISL1-positive cells. In some embodiments, about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99% of the cells in the population are ISL1-positive cells.

In some embodiments, the population comprises more NKX6.1-negative, ISL1-positive cells than NKX6.1-positive, ISL1-positive cells. In some embodiments, at least 40% of the cells in the population are NKX6.1-negative, ISL1-positive cells. In some embodiments, at least 45%, at least 50%, about 40-50%, about 45-55%, or about 50-55% of the cells in the population are NKX6.1-negative, ISL1-positive cells. In some embodiments, about 40%, 41%, 42%, 43%, 44%, 45%, 46%, 47%, 48%, 49%, 50%, 51%, 52%, 53%, 54%, or about 55% of the cells in the population are NKX6.1-negative, ISL1-positive cells.

In some aspects, the present disclosure provides an in vitro composition that comprises PDX1-positive, NKX6.1-positive pancreatic progenitor cells; NKX6.1-positive, ISL1-positive endocrine cells; and a PKC activator; wherein the PKC activator is a benzolactam derivative. In some cases, the benzolactam is TPPB. In some cases, the composition further comprises a γ-secretase inhibitor. The γ-secretase inhibitor can be XXI.

In some cases, the composition provided herein comprises a differentiation factor selected from the group consisting of: a TGF-β signaling pathway inhibitor, a thyroid hormone signaling pathway activator, an epigenetic modifying compound, a growth factor from EGF family, a RA signaling pathway activator, a SHH pathway inhibitor, a protein kinase inhibitor, a ROCK inhibitor, and a BMP signaling pathway inhibitor. In some cases, the composition also comprises serum albumin protein.

In some cases, the composition provided herein comprises serum albumin protein, a TGF-β signaling pathway inhibitor, a thyroid hormone signaling pathway activator, an epigenetic modifying compound, a SHH pathway inhibitor, a protein kinase inhibitor, a ROCK inhibitor, and a BMP signaling pathway inhibitor.

In some cases, the ROCK inhibitor is thiazovavin. In some cases, the RA signaling pathway activator is retinoic acid. In some cases, the SHH pathway inhibitor is Sant-1. In some cases, the TGF-β signaling pathway inhibitor is ALK5i. In some cases, the growth factor from the EGF family is betacellulin. In some cases, the thyroid hormone signaling pathway activator is T3, GC-1 or a thyroid hormone derivative. In some cases, the protein kinase inhibitor is staurosporine. In some cases, the BMP signaling pathway inhibitor is LDN193189 or DMH-1. In some cases, the epigenetic modifying compound is DZNep.

In some cases, the cell compositions of the present disclosure have at least about 35% cells expressing C-peptide and not expressing VMAT1, as measured by flow cytometry. In some cases, the expression of C-peptide and absence of VMAT1 in a cell of the cell compositions suggest that the cell is a SC-β cell. In some cases, the cell compositions have at least about 30%, 32%, 33%, 34%, 35%, 36%, 37%, 38%, 39%, 40%, 41%, 42%, 43%, 44%, 45%, 46%, 47%, 48%, 49%, or 50% cells expressing C-peptide and not expressing VMAT1, as measured by flow cytometry. In some cases, the cell compositions have about 30%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% cells expressing C-peptide and not expressing VMAT1, as measured by flow cytometry. In some cases, the cell compositions have about 30% to about 60%, about 35% to about 55%, about 40% to about 50% cells expressing C-peptide and not expressing VMAT1, as measured by flow cytometry.

In some cases, the cell compositions of the present disclosure have at most about 35% cells expressing VMAT1, as measured by flow cytometry. In some cases, the cell compositions of the present disclosure have at most about 35% cells expressing VMAT1 and not expressing C-peptide, as measured by flow cytometry. In some cases, the expression of VMAT1 and absence of C-peptide in a cell of the cell compositions suggest that the cell is a SC-EC cell. In some cases, the cell compositions have at most about 35%, 32%, 31%, 30%, 28%, 25%, 24%, 23%, 22%, 21%, or 20% cells expressing VMAT1 and not expressing C-peptide, as measured by flow cytometry. In some cases, the cell compositions have about 35%, 32%, 31%, 30%, 28%, 25%, 24%, 23%, 22%, 21%, 20%, 19%, 18%, 17%, 16%, or 15% cells expressing VMAT1 and not expressing C-peptide, as measured by flow cytometry. In some cases, the cell compositions have about 15% to about 30%, about 16% to 25%, about 17% to about 22%, about 18% to about 20% cells expressing VMAT1 and not expressing C-peptide, as measured by flow cytometry.

In some cases, the cell composition include at least about 20% cells expressing glucagon, as measured by flow cytometry. In some cases, the cell composition include at least about 15% cells expressing glucagon and not expressing somatostatin, as measured by flow cytometry. In some cases, the expression of glucagon and not expressing somatostatin in a cell of the cell composition suggest that the cell is a SC-α cell. In some cases, the cell composition include at least about 12%, 13%, 14%, 15%, 16%, 17%, 18%, 19%, 20%, 21%, or 22% cells expressing glucagon and not expressing somatostatin, as measured by flow cytometry. In some cases, the cell composition include about 10% to about 30%, about 12% to about 25%, about 13% to about 22%, about 15% to about 20%, or about 16% to about 18% cells expressing glucagon and not expressing somatostatin, as measured by flow cytometry. In some cases, the cell composition include about 12%, 13%, 14%, 15%, 16%, 17%, 18%, 19%, 20%, 21%, or 22% cells expressing glucagon and not expressing somatostatin, as measured by flow cytometry.

In some cases, the cell composition include at least about 4% cells expressing somatostatin and not expressing glucagon, as measured by flow cytometry. In some cases, the expression of glucagon and not expressing somatostatin in a cell of the cell composition suggest that the cell is a SC-δ cell. In some cases, the cell composition include at least about 2%, 3%, 4%, 5%, 6%, 7%, or 8% cells expressing somatostatin and not expressing glucagon, as measured by flow cytometry. In some cases, the cell composition include about 1% to about 9%, about 2% to about 8%, about 3% to about 7%, or about 4% to about 6% cells expressing somatostatin and not expressing glucagon, as measured by flow cytometry. In some cases, the cell composition include about 2%, 3%, 4%, 5%, 6%, 7%, or 8% cells expressing somatostatin and not expressing glucagon, as measured by flow cytometry.

In some cases, the cell composition have at least about 35% cells expressing C-peptide and not expressing VMAT1, at most about 30% cells expressing VMAT1, and at least about 20% cells expressing glucagon, as measured by flow cytometry. In some cases, the cell composition have at least about 35% cells expressing C-peptide and not expressing VMAT1, at most about 30% cells expressing VMAT1, at least about 20% cells expressing glucagon, and at least 4% cells expressing somatostatin and not expressing glucagon, as measured by flow cytometry.

In some cases, the cell composition provided herein include (a) at least about 35% cells expressing C-peptide and not expressing VMAT1; and (b) at least about 10% cells expressing somatostatin, as measured by flow cytometry. In some cases, there are at least about 15% cells expressing somatostatin in the cell composition, as measured by flow cytometry.

In some cases, provided herein is a composition comprising a population of cells, wherein: (a) 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the population of cells express C-peptide and ISL1 but not VMAT1; (b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and/or (c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

In some cases, provided herein is a composition comprising a population of cells, wherein: (a) 30-90%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, 70-90%, 70-80%, or 80-90% of the cells in the population of cells express C-peptide and ISL1 but not VMAT1; (b) 5-40%, 5-35%, 5-30%, 5-25%, 5-20%, 5-15%, 5-10%, 10-40%, 10-35%, 10-30%, 10-25%, 10-20%, 10-15%, 15-40%, 15-35%, 15-30%, 15-25%, 15-20%, 20-40%, 20-35%, 20-30%, 20-25%, 25-40%, 25-35%, 25-30%, 30-40%, 30-35% or 35-40% of the cells in the population of cells express glucagon but not somatostatin; and (c) 3-20%, 3-15%, 3-12%, 3-10%, 3-8%, 3-5%, 4-20%, 4-15%, 4-12%, 4-10%, 4-8%, 4-5%, 5-20%, 5-15%, 5-12%, 5-10%, 5-8%, 7-20%, 7-15%, 7-12%, 7-10%, 9-20%, 9-15%, 9-12%, 8-10%, 8-12%, 8-15%, 8-20%, 10-20%, 10-12%, 10-15%, 12-20%, 12-15% or 15-20% of the cells in the population of cells express somatostatin but not glucagon.

In some cases, in the population of cells provided herein, 40-60% of the cells express C-peptide and ISL1 but not VMAT1; 10-25%, of the cells express glucagon but not somatostatin; and 4-10% of the cells express somatostatin but not glucagon. In some cases, less than 25%, less than 20%, less than 18%, less than 15%, less than 12%, or less than 10% of the cells in the population of cells provided herein express VMAT1 but not C-peptide.

Still other embodiments of the present disclosure relate to compositions, such as isolated cell populations or cell cultures, comprising mixtures of SC-β cells and insulin-positive endocrine cells or precursors thereof from which they were differentiated from. For example, cell cultures or cell populations comprising at least about 5 SC-β cells for about every 95 insulin-positive endocrine cells or precursors thereof can be produced. In other embodiments, cell cultures or cell populations comprising at least about 95 SC-β cells for about every 5 insulin-positive endocrine cells or precursors thereof can be produced. Additionally, cell cultures or cell populations comprising other ratios of SC-β cells to insulin-positive endocrine cells or precursors thereof are contemplated. For example, compositions comprising at least about one SC-β cell for about every 1,000,000, or at least 100,000 cells, or at least 10,000 cells, or at least 1000 cells or 500, or at least 250 or at least 100 or at least 10 insulin-positive endocrine cells or precursors thereof can be produced.

In some cases, cell populations or cell clusters disclosed herein are unsorted, e.g., isolated cell populations or cell clusters that have not been through cell sorting process. In some embodiments, the cell cluster disclosed herein can refer to a cell cluster formed by self-aggregation of cells cultured in a given environment, for instance, in a 3D suspension culture. In some embodiments, cell clusters disclosed herein are intermediate cell clusters formed during the differentiation process as described herein. In some cases, the intermediate cell clusters, e.g., cell clusters comprising PDX1-positive, NKX6.1-negative pancreatic progenitor cells (e.g., Stage 3 cell clusters) or cell clusters comprising PDX1-positive, NKX6.1-positive pancreatic progenitor cells (e.g., Stage 4 cell clusters), are not subjected to cell sorting. In some case, cell populations going through cell sorting may not be able to form the intermediate cell clusters disclosed herein. For instance, PDX1-positive pancreatic progenitor cells, after going through cell sorting, may not be able to form a cell cluster as disclosed herein.

Cell sorting as described herein can refer to a process of isolating a group of cells from a plurality of cells by relying on differences in cell size, shape (morphology), surface protein expression, endogenous signal protein expression, or any combination thereof. In some cases, cell sorting comprises subjecting the cells to flow cytometry. Flow cytometry can be a laser- or impedance-based, biophysical technology. During flow cytometry, one can suspend cells in a stream of fluid and pass them through an electronic detection apparatus. In one type of flow cytometry, fluorescent-activated cell sorting (FACS), based on one or more parameters of the cells' optical properties (e.g., emission wave length upon laser excitation), one can physically separate and thereby purify cells of interest using flow cytometry. As described herein, an unsorted cell cluster can be cell cluster that formed by a plurality of cells that have not been subject to an active cell sorting process, e.g., flow cytometry. In some cases, flow cytometry as discussed herein can be based on one or more signal peptides expressed in the cells. For example, a cell cluster can comprise cells that express a signal peptide (e.g., a fluorescent protein, e.g., green fluorescent protein (GFP) or tdTomato). In some cases, the signal peptide is expressed as an indicator of insulin expression in the cells. For instance, a cell cluster can comprise cell harboring an exogenous nucleic acid sequence coding for GFP under the control of an insulin promoter. The insulin promoter can be an endogenous or exogenous promoter. In some cases, the expression of GFP in these cells can be indicative of insulin expression in the cells. The GFP signal can thus be a marker of a pancreatic β cell. In some cases, cell sorting as described herein can comprise magnetic-activated flow cytometry, where magnetic antibody or other ligand is used to label cells of different types, and the differences in magnetic properties can be used for cell sorting.

The percentage of cells expressing one or more particular markers, like PDX1, NKX6.1, insulin, NGN3, or CHGA, described herein can be the percentage value detected using techniques like flow cytometry assay. In some cases, during a flow cytometry assay, cell population or cell cluster discussed herein are dispersed into single-cell suspension by incubation in digesting enzyme like trypsin or TrypLE™ Express. Dispersed cell can be washed in suitable buffer like PBS, centrifuged and then re-suspended in fixation buffer like 4% PFA. Incubation with primary antibodies against the cell markers of interest can then be conducted, which can be followed by incubation with the secondary antibodies. After antibody incubation, the cells can be washed and the subject to segregation by flow cytometry. Techniques other than flow cytometry can also be used to characterize the cells described herein, e.g., determine the cell percentages. Non-limiting examples of cell characterization methods include gene sequencing, microscopic techniques (fluorescence microscopy, atomic force microscopy), karyotyping, isoenzyme analysis, DNA properties, and viral susceptibility.

In some aspects, the disclosure relates to a composition comprising a population of glucose-responsive insulin secreting cells, wherein the cells secrete a higher amount of insulin upon induction with KCl (e.g., about 20 to about 50 mM, e.g., about 30 mM) as compared to the amount of insulin secreted upon induction with glucose. In some embodiments, the population of glucose-responsive insulin secreting cells secrete at least 1.5 times, 2 times, 2.5 times, 3 times higher amount of insulin upon induction with KCl as compared to the amount of insulin secreted upon induction with glucose.

In some aspects, the disclosure relates to a composition comprising a population of glucose-responsive insulin secreting cells, wherein the cells secrete a higher amount of insulin upon induction with KCl and/or glucose, in the presence of a signaling factor as compared to comparable cells in the absence of the signaling factor. In some embodiments, the cells secrete higher amount of insulin in the presence of high glucose, but not in the presence of low glucose. In some embodiments, the high glucose concentration is about 10-20 mM. In some embodiments, the low glucose concentration is about 2-5 mM.

In some aspects, the disclosure relates to a composition comprising a population of differentiated pancreatic progenitor cells, wherein the population comprises at least 60% pancreatic β cells as determined by flow cytometry. In some embodiments, the population comprises at least 65%, 70%, 75%, 80%, 85%, or 90% pancreatic β cells. In some embodiments, the population comprises a higher percentage of pancreatic β cells upon being contacted with a predetermined basal medium component as compared to a comparable population not contacted with the basal medium component.

The in vitro-matured, SC-β cell (e.g., pancreatic β cells) generated according to the disclosed methods described herein demonstrate many advantages, for example, they perform glucose stimulated insulin secretion in vitro, resemble human islet β cells by gene expression and ultrastructure, secrete human insulin and ameliorate hyperglycemia when transplanted into mice, provide a new platform for cell therapy (e.g., transplantation into a subject in need of additional and/or functional β cells), drug screening (e.g., for insulin production/secretion, survival, dedifferentiation, etc.), research (e.g., determining the differences in function between normal and diabetic β cell), and tissue engineering (e.g., using the SC-β cells as the first cell type in reconstructing an islet).

Stem Cells and Reprogramming

Provided herein is use of stem cells for producing SC-β cells (e.g., mature pancreatic β cells or β-like cells) or precursors thereof. In an embodiment, germ cells may be used in place of, or with, the stem cells to provide at least one SC-β cell, using similar protocols as described in U.S. Patent Application Publication No. US20150240212 and US20150218522, each of which is herein incorporated by reference in its entirety. Suitable germ cells can be prepared, for example, from primordial germ cells present in human fetal material taken about 8-11 weeks after the last menstrual period. Illustrative germ cell preparation methods are described, for example, in Shamblott et al., Proc. Natl. Acad. Sci. USA 95:13726, 1998 and U.S. Pat. No. 6,090,622.

Provided herein are compositions and methods of generating SC-β cells (e.g., pancreatic β cells), as well as pancreatic α cells, and/or pancreatic δ cells. In some embodiments, the disclosure provides for methods of generating cell populations that are enriched for pancreatic α cells. In some embodiments, the disclosure provides for methods of generating cell populations that are enriched for pancreatic δ cells.

Generally, the at least one SC-β cell or precursor thereof, e.g., pancreatic progenitors produced according to the methods disclosed herein can comprise a mixture or combination of different cells, e.g., for example a mixture of cells such as primitive gut tube cells, PDX1-positive pancreatic progenitors, PDX1-positive, NKX6.1-positive pancreatic progenitors, Ngn3-positive endocrine progenitor cells, insulin-positive endocrine cell (e.g., NKX6.1-positive, ISL1-positive cells, or β-like cells), and/or other pluripotent or stem cells.

The at least one pancreatic α, β and/or δ cell or precursor thereof can be produced according to any suitable culturing protocol to differentiate a stem cell or pluripotent cell to a desired stage of differentiation. In some embodiments, the at least one pancreatic α, β and/or δ cell or the precursor thereof are produced by culturing at least one pluripotent cell for a period of time and under conditions suitable for the at least one pluripotent cell to differentiate into the at least one pancreatic α, β and/or δ cell or the precursor thereof.

In some embodiments, the at least one pancreatic α, β and/or δ cell or precursor thereof is a substantially pure population of pancreatic α, β and/or δ cells or precursors thereof. In some embodiments, a population of pancreatic α, β and/or δ cells or precursors thereof comprises a mixture of pluripotent cells or differentiated cells. In some embodiments, a population pancreatic α, β and/or δ cells or precursors thereof are substantially free or devoid of embryonic stem cells or pluripotent cells or iPS cells.

In some embodiments, a somatic cell, e.g., fibroblast can be isolated from a subject, for example as a tissue biopsy, such as, for example, a skin biopsy, and reprogrammed into an induced pluripotent stem cell for further differentiation to produce the at least one pancreatic α, β and/or δ cell or precursor thereof for use in the compositions and methods described herein. In some embodiments, a somatic cell, e.g., fibroblast is maintained in culture by methods known by one of ordinary skill in the art, and in some embodiments, propagated prior to being converted into pancreatic α, β and/or δ cells by the methods as disclosed herein.

In some embodiments, the at least one pancreatic α, β and/or δ cell or precursor thereof are maintained in culture by methods known by one of ordinary skills in the art, and in some embodiments, propagated prior to being converted into pancreatic α, β and/or δ cells by the methods as disclosed herein.

Further, at least one pancreatic α, β and/or δ cell or precursor thereof, e.g., pancreatic progenitor can be from any mammalian species, with non-limiting examples including a murine, bovine, simian, porcine, equine, ovine, or human cell. For clarity and simplicity, the description of the methods herein refers to a mammalian at least one pancreatic α, β and/or δ cell or precursor thereof but it should be understood that all of the methods described herein can be readily applied to other cell types of at least one pancreatic α, β and/or δ cell or precursor thereof. In some embodiments, the at least one pancreatic α, β and/or δ cell or precursor thereof is derived from a human individual.

Stem Cells

Embodiments of the present disclosure are related to use of stem cells for generation of pancreatic α, β and/or δ cells or precursors thereof. The term "stem cell" as used herein can refer to a cell (e.g., plant stem cell, vertebrate stem cell) that has the ability both to self-renew and to generate a differentiated cell type (Morrison et al., (1997) Cell 88:287-298). In the context of cell ontogeny, the adjective "differentiated", or "differentiating" is a relative term. A "differentiated cell" can be a cell that has progressed further down the developmental pathway than the cell it is being compared with. Thus, pluripotent stem cells can differentiate into lineage-restricted progenitor cells (e.g., mesodermal stem cells), which in turn can differentiate into cells that are further restricted (e.g., neuron progenitors), which can differentiate into end-stage cells (e.g., terminally differentiated cells, e.g., neurons, cardiomyocytes, etc.), which play a characteristic role in a certain tissue type, and can or cannot retain the capacity to proliferate further. Stem cells can be characterized by both the presence of specific markers (e.g., proteins, RNAs, etc.) and the absence of specific markers. Stem cells can also be identified by functional assays both in vitro and in vivo, particularly assays relating to the ability of stem cells to give rise to multiple differentiated progeny. In an embodiment, the host cell is an adult stem cell, a somatic stem cell, a non-embryonic stem cell, an embryonic stem cell, hematopoietic stem cell, an include pluripotent stem cells, and a trophoblast stem cell.

Stem cells of interest, e.g., that can be used in the method provided herein, can include pluripotent stem cells (PSCs). The term "pluripotent stem cell" or "PSC" as used herein can refer to a stem cell capable of producing all cell types of the organism. Therefore, a PSC can give rise to cells of all germ layers of the organism (e.g., the endoderm, mesoderm, and ectoderm of a vertebrate). Pluripotent cells can be capable of forming teratomas and of contributing to ectoderm, mesoderm, or endoderm tissues in a living organism. Pluripotent stem cells of plants can be capable of giving rise to all cell types of the plant (e.g., cells of the root, stem, leaves, etc.).

Embodiments of the present disclosure are related to use of PSCs for generation of pancreatic α, β and/or δ cells or precursors thereof. PSCs of animals can be derived in a number of different ways. For example, embryonic stem cells (ESCs) can be derived from the inner cell mass of an embryo (Thomson et. al, Science. 1998 Nov. 6; 282(5391): 1145-7) whereas induced pluripotent stem cells (iPSCs) can be derived from somatic cells (Takahashi et. al, Cell. 2007 Nov. 30; 131(5):861-72; Takahashi et. al, Nat Protoc. 2007; 2(12):3081-9; Yu et. al, Science. 2007 Dec. 21; 318(5858): 1917-20. Epub 2007 Nov. 20). Because the term PSC can refer to pluripotent stem cells regardless of their derivation, the term PSC can encompass the terms ESC and iPSC, as well as the term embryonic germ stem cells (EGSC), which are another example of a PSC. PSCs can be in the form of an established cell line, they can be obtained directly from primary embryonic tissue, or they can be derived from a somatic cell.

Embodiments of the present disclosure are related to use of ESCs for generation of pancreatic β cells or precursors thereof. By "embryonic stem cell" (ESC) can be meant a PSC that is isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells can be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs can grow as flat colonies with large nucleo-cytoplasmic ratios, defined borders and prominent nucleoli. In addition, ESCs can express SSEA-3, SSEA-4, TRA-1-60, TRA-1-81, and Alkaline Phosphatase, but not SSEA-1. Examples of methods of generating and characterizing ESCs can be found in, for example, U.S. Pat. Nos. 7,029,913, 5,843,780, and 6,200,806, each of which is incorporated herein by its entirety. Methods for proliferating hESCs in the undifferentiated form are described in WO 99/20741, WO 01/51616, and WO 03/020920, each of which is incorporated herein by its entirety.

By "embryonic germ stem cell" (EGSC) or "embryonic germ cell" or "EG cell", it can be meant a PSC that is derived from germ cells and/or germ cell progenitors, e.g. primordial germ cells, e.g. those that can become sperm and eggs. Embryonic germ cells (EG cells) are thought to have properties similar to embryonic stem cells as described above. Examples of methods of generating and characterizing EG cells may be found in, for example, U.S. Pat. No. 7,153,684;

Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, each of which are incorporated herein by its entirety.

Embodiments of the present disclosure are related to use of iPSCs for generation of pancreatic α, β and/or δ cells or precursors thereof. By "induced pluripotent stem cell" or "iPSC", it can be meant a PSC that is derived from a cell that is not a PSC (e.g., from a cell this is differentiated relative to a PSC). iPSCs can be derived from multiple different cell types, including terminally differentiated cells. iPSCs can have an ES cell-like morphology, growing as flat colonies with large nucleo-cytoplasmic ratios, defined borders and prominent nuclei. In addition, iPSCs can express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs can be found in, for example, U.S. Patent Publication Nos. US20090047263, US20090068742, US20090191159, US20090227032, US20090246875, and US20090304646, each of which are incorporated herein by its entirety. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

Embodiments of the present disclosure are related to use of somatic cells for generation of pancreatic α, β and/or δ cells or precursors thereof. By "somatic cell", it can be meant any cell in an organism that, in the absence of experimental manipulation, does not ordinarily give rise to all types of cells in an organism. In other words, somatic cells can be cells that have differentiated sufficiently that they may not naturally generate cells of all three germ layers of the body, e.g. ectoderm, mesoderm and endoderm. For example, somatic cells can include both neurons and neural progenitors, the latter of which is able to naturally give rise to all or some cell types of the central nervous system but cannot give rise to cells of the mesoderm or endoderm lineages In certain examples, the stem cells can be undifferentiated (e.g. a cell not committed to a specific lineage) prior to exposure to at least one differentiation factor or composition according to the methods as disclosed herein, whereas in other examples it can be desirable to differentiate the stem cells to one or more intermediate cell types prior to exposure of the at least one differentiation factor or composition described herein. For example, the stems cells can display morphological, biological or physical characteristics of undifferentiated cells that can be used to distinguish them from differentiated cells of embryo or adult origin. In some examples, undifferentiated cells can appear in the two dimensions of a microscopic view in colonies of cells with high nuclear/cytoplasmic ratios and prominent nucleoli. The stem cells can be themselves (for example, without substantially any undifferentiated cells being present) or can be used in the presence of differentiated cells. In certain examples, the stem cells can be cultured in the presence of) suitable nutrients and optionally other cells such that the stem cells can grow and optionally differentiate. For example, embryonic fibroblasts or fibroblast-like cells can be present in the culture to assist in the growth of the stem cells. The fibroblast can be present during one stage of stem cell growth but not necessarily at all stages. For example, the fibroblast can be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells can have the characteristic of being capable under appropriate conditions of producing progeny of different cell types, e.g. derivatives of all of at least one of the 3 germinal layers (endoderm, mesoderm, and ectoderm). These cell types can be provided in the form of an established cell line, or they can be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, FISF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into mature, insulin positive cells did not involve destroying a human embryo. In some embodiments, the source of human stem cells or pluripotent stem cells used for chemically-induced differentiation into mature, insulin positive cells do not involve destroying a human embryo.

In another example, the stem cells can be isolated from tissue including solid tissue. In some embodiments, the tissue is skin, fat tissue (e.g. adipose tissue), muscle tissue, heart or cardiac tissue. In other embodiments, the tissue is for example but not limited to, umbilical cord blood, placenta, bone marrow, or chondral.

Stem cells that can be used in the methods provided herein can also include embryonic cells of various types, exemplified by human embryonic stem (hES) cells, as described by Thomson et al, (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., Proc. Natl. Acad. Sci. USA 95:13726, 1998). Also applicable to the methods provided herein can be lineage committed stem cells, such as mesodermal stem cells and other early cardiogenic cells (see Reyes et al, (2001) Blood 98:2615-2625; Eisenberg & Bader (1996) Circ Res. 78(2):205-16; etc.) The stem cells can be obtained from any mammalian species, e.g. human, equine, bovine, porcine, canine, feline, rodent, e.g. mice, rats, hamster, primate, etc. In some embodiments, a human embryo was not destroyed for the source of pluripotent cell used on the methods and compositions as disclosed herein. In some embodiments, a human embryo is not destroyed for the source of pluripotent cell used on the methods and compositions as disclosed herein.

A mixture of cells from a suitable source of endothelial, muscle, and/or neural stem cells can be harvested from a mammalian donor for the purpose of the present disclosure. A suitable source is the hematopoietic microenvironment. For example, circulating peripheral blood, preferably mobilized (e.g., recruited), may be removed from a subject. In an embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

In some embodiments, the pancreatic α, β and/or δ cell as described herein can be derived from one or more of trichocytes, keratinocytes, gonadotropes, corticotropes, thyrotropes, somatotropes, lactotrophs, chromaffin cells, parafollicular cells, glomus cells melanocytes, nevus cells, Merkel cells, odontoblasts, cementoblasts corneal keratocytes, retina Muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells (e.g., PP cells), pancreatic ε cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, splenocytes (e.g., T lymphocytes, B lymphocytes, dendritic cells, microphages, leukocytes), trophoblast stem cells, or any combination thereof.

Reprogramming

The term "reprogramming" as used herein can refer to the process that alters or reverses the differentiation state of a somatic cell. The cell can either be partially or terminally differentiated prior to the reprogramming Reprogramming can encompass complete reversion of the differentiation state of a somatic cell to a pluripotent cell. Such complete reversal of differentiation can produce an induced pluripotent (iPS) cell. Reprogramming as used herein can also encompass partial reversion of a cells differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming can involve alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

As used herein, the term "reprogramming factor" can refer to a molecule that is associated with cell "reprogramming," that is, differentiation, and/or de-differentiation, and/or transdifferentiation, such that a cell converts to a different cell type or phenotype. Reprogramming factors generally affect expression of genes associated with cell differentiation, de-differentiation and/or transdifferentiation. Transcription factors are examples of reprogramming factors.

The term "differentiation" and their grammatical equivalents as used herein can refer to the process by which a less specialized cell (e.g., a more naive cell with a higher cell potency) becomes a more specialized cell type (e.g., a less naive cell with a lower cell potency); and that the term "de-differentiation" can refer to the process by which a more specialized cell becomes a less specialized cell type (e.g., a more naive cell with a higher cell potency); and that the term "transdifferentiation" refers to the process by which a cell of a particular cell type converts to another cell type without significantly changing its "cell potency" or "naivety" level. Without wishing to be bound by theory, it is thought that cells "transdifferentiate" when they convert from one lineage-committed cell type or terminally differentiated cell type to another lineage-committed cell type or terminally differentiated cell type, without significantly changing their "cell potency" or "naivety" level.

As used herein, the term "cell potency" is to be understood as referring to the ability of a cell to differentiate into cells of different lineages. For example, a pluripotent cell (e.g., a stem cell) has the potential to differentiate into cells of any of the three germ layers, that is, endoderm (interior stomach lining, gastrointestinal tract, the lungs), mesoderm (muscle, bone, blood, urogenital), or ectoderm (epidermal tissues and nervous system), and accordingly has high cell potency; a multipotent cell (e.g., a stem cell or an induced stem cell of a certain type) has the ability to give rise to cells from a multiple, but limited, number of lineages (such as hematopoietic stem cells, cardiac stem cells, or neural stem cells, etc.) comparatively has a lower cell potency than pluripotent cells. Cells that are committed to a particular lineage or are terminally differentiated can have yet a lower cell potency. Specific examples of transdifferentiation known in the art include the conversion of e.g., fibroblasts beta cells or from pancreatic exocrine cells to beta cells etc.

Accordingly, the cell may be caused to differentiate into a more naive cell (e.g., a terminally differentiated cell may be differentiated to be multipotent or pluripotent); or the cell may be caused to de-differentiate into a less naive cell (e.g., a multipotent or pluripotent cell can be differentiated into a lineage-committed cell or a terminally differentiated cell). However, in an embodiment, the cell may be caused to convert or transdifferentiate from one cell type (or phenotype) to another cell type (or phenotype), for example, with a similar cell potency level. Accordingly, in an embodiment of the present disclosure, the inducing steps of the present disclosure can reprogram the cells of the present disclosure to differentiate, de-differentiate and/or transdifferentiate. In an embodiment of the present disclosure, the inducing steps of the present disclosure may reprogram the cells to transdifferentiate.

Methods of reprogramming or inducing a particular type of cell to become another type of cell, for example, by differentiation, de-differentiation and/or transdifferentiation using one or more exogenous polynucleotide or polypeptide reprogramming factors are known to the person skilled in the art. Such methods may rely on the introduction of genetic material encoding one or more transcription factor(s) or other polypeptide(s) associated with cell reprogramming. For example, PDX1, Ngn3 and MafA, or functional fragments thereof are all known to encode peptides that can induce cell differentiation, de-differentiation and/or transdifferentiation of the cells of the present disclosure. In some methods known to the person skilled in the art, exogenous polypeptides (e.g. recombinant polypeptides) encoded by reprogramming genes (such as the above genes) are contacted with the cells to induce, for example, cells of the present disclosure. The person skilled in the art will appreciate that other genes may be associated with reprogramming of cells, and exogenous molecules encoding such genes (or functional fragments thereof) and the encoded polypeptides are also considered to be polynucleotide or polypeptide reprogramming factors (e.g. polynucleotides or polypeptides that in turn affect expression levels of another gene associated with cell reprogramming) For example, it has been shown that the introduction of exogenous polynucleotide or polypeptide epigenetic gene silencers that decrease p53 inactivation increase the efficiency of inducing induced pluripotent stem cells (iPSC). Accordingly, exogenous polynucleotides or polypeptides encoding epigenetic silencers and other genes or proteins that may be directly or indirectly involved in cell reprogramming or increasing cell programming efficiency would be considered to constitute an exogenous polynucleotide or polypeptide reprogramming factor. The person skilled in the art will appreciate that other methods of influencing cell reprogramming exist, such as introducing RNAi molecules (or genetic material encoding RNAi molecules) that can knock down expression of genes involved in inhibiting cell reprogramming. Accordingly, any exogenous polynucleotide molecule or polypeptide molecule that is associated with cell reprogramming, or enhances cell reprogramming, is to be understood to be an exogenous polynucleotide or polypeptide reprogramming factor as described herein.

In some embodiments of the present disclosure, the method excludes the use of reprogramming factor(s) that are not small molecules. However, it will be appreciated that the method can utilize "routine" tissue culture components such as culture media, serum, serum substitutes, supplements, antibiotics, etc, such as RPMI, Renal Epithelial Basal Medium (REBM), Dulbecco's Modified Eagle Medium (DMEM), MCDB131 medium, CMRL 1066 medium, F12, foetal calf serum (FCS), foetal bovine serum (FBS), bovine serum albumin (BSA), D-glucose, L-glutamine, GlutaMAX™-1 (dipeptide, L-alanine-L-glutamine), B27, heparin, progesterone, putrescine, laminin, nicotinamide, insulin, transferrin, sodium selenite, selenium, ethanolamine, human epidermal growth factor (hEGF), basic fibroblast growth factor (bFGF), hydrocortisone, epinephrine, normacin, penicillin, streptomycin, gentamicin and amphotericin, etc. It is to be understood that these typical tissue culture components (and other similar tissue culture components that are routinely used in tissue culture) are not small molecule reprogramming molecules for the purposes of the present disclosure. These components are either not small molecules as defined herein and/or are not reprogramming factors as defined herein.

Accordingly, in an embodiment, the present disclosure does not involve a culturing step of the cell(s) with one or more exogenous polynucleotide or polypeptide reprogramming factor(s). Accordingly, in an embodiment, the method of the present disclosure does not involve the introduction of one or more exogenous polynucleotide or polypeptide reprogramming factor(s), e.g., by introducing transposons, viral transgenic vectors (such as retroviral vectors), plasmids, mRNA, miRNA, peptides, or fragments of any of these molecules, that are involved in producing induced α, β and/or δ cells or, otherwise, inducing cells of the present disclosure to differentiate, de-differentiation and/or transdifferentiate.

That is, in an embodiment, the method occurs in the absence of one or more exogenous polynucleotide or polypeptide reprogramming factor(s). Accordingly, it is to be understood that in an embodiment, the method of the present disclosure utilizes small molecules (e.g., HDAC inhibitors) to reprogram cells, without the addition of polypeptide transcription factors; other polypeptide factors specifically associated with inducing differentiation, de-differentiation, and/or transdifferentiation; polynucleotide sequences encoding polypeptide transcription factors, polynucleotide sequences encoding other polypeptide factors specifically associated with inducing differentiation, de-differentiation, and/or transdifferentiation; mRNA; interference RNA; microRNA and fragments thereof.

Methods of Generating Stem Cell Derived β Cells

Provided herein are methods of generating SC-β cells (e.g., non-native pancreatic β cells). The detailed protocols of generating endocrine cells the stem cells to provide at least one SC-β cell are described in U.S. Patent Application Publication No. US20150240212 and US20150218522, each of which is herein incorporated by reference in its entirety.

The endoderm can give rise to digestive and respiratory tracts, thyroid, liver, and pancreas. Representative disease of endoderm lineages is type 1 diabetes resulting from destruction of the insulin-producing β cells. Generation of functional β cells from human pluripotent stem cells (hPSC) in vitro can be practical, renewable cell source for replacement cell therapy for type 1 diabetes. The embryotic stem (ES) cells that are generated from the inner cell mass of blastocyst-stage embryos represent a promising source of cells for transplantation or cell-based therapy of any damaged cells. They can be maintained in culture, renew for themselves, and proliferate unlimitedly as undifferentiated ES cells. The ES cells are capable of differentiating into all cell types of the body as the ectoderm, mesoderm, and endoderm lineage cells or tissues. The major benefit of ES cells is stable self-renewal in culture and the potential to differentiate.

The definitive endoderm can be generated in vivo from the inner cell mass by the process of gastrulation of embryogenesis, in which epiblast cells are instructed to form the three germ layers. Definitive endoderm can give rise to diverse cells and tissues that contribute to vital organs as the pancreatic β cells, liver hepatocytes, lung alveolar cells, thyroid, thymus, and the epithelial lining of the alimentary and respiratory tract. It is different from the primitive endoderm of extraembryonic tissues, which can give rise to the visceral and parietal endoderm. The definitive endoderm derived from ES cells is theoretically capable of becoming any endoderm derivatives, and directing ES cells into the endoderm lineage is a prerequisite for generating therapeutic endoderm derivatives.

Precise patterning of anterior-posterior axis of the definitive endoderm can eventually form the primitive gut tube. The definitive endoderm-derived primitive gut tube induces the pharynx, esophagus, stomach, duodenum, small and large intestine along the anterior-posterior axis as well as associated organs, including pancreas, lung, thyroid, thymus, parathyroid, and liver. The anterior portion of the foregut of the primitive gut tube becomes lung, thyroid, esophagus, and stomach. The pancreas, liver, and duodenum originate from the posterior portion of the foregut. The midgut and hindgut of primitive gut tube gives rise to the small and large intestine. The anterior foregut expresses developmental markers, NK2 homeobox 1 (NKX2-1) and SRY (sex determining region Y)-box 2 (50X2); the posterior foregut expresses hematopoietically expressed homeobox (HHEX), pancreatic and duodenal homeobox 1 (PDX1), one cut homeobox 1 (ONECUT1, known as HNF6), and hepatocyte nuclear factor 4 alpha (HNF4A); and the midgut/hindgut expresses caudal type homeobox 1 (CDX1), caudal type homeobox 2 (CDX2), and motor neuron and pancreas homeobox 1 (MNX1) (3, 19, 20).

The successful differentiation to pancreatic β cells should require that differentiated cells synthesize and secrete physiologically appropriate amounts of insulin. An exemplary stepwise protocol directing hPSC cell differentiation is developed, which entails differentiation processes that recapitulates the major stages of normal pancreatic endocrine development (for instance, the Version A protocol in EXAMPLE 1). The differentiation of hPSC cells to hormone-expressing pancreatic endocrine cells is conducted by transiting hPSC cells through major stages of embryonic development; differentiation to mesendoderm and definitive endoderm, establishment of the primitive gut endoderm, patterning of the posterior foregut, and specification and maturation of pancreatic endoderm and endocrine precursors. Through these stages, hPSC cells can obtain pancreatic endocrine phenotype and ability of glucose responsive insulin secretion in vitro.

Generally, the at least one pancreatic α, β and/or δ cell or precursor thereof, e.g., pancreatic progenitors produced according to the methods disclosed herein can comprise a mixture or combination of different cells, e.g., for example a mixture of cells such as a PDX1-positive pancreatic progenitors, pancreatic progenitors co-expressing PDX1 and NKX6-1, a Ngn3-positive endocrine progenitor cell, an insulin-positive endocrine cell (e.g., NKX6.1-positive, ISL1-positive cells, or β-like cells), and/or other pluripotent or stem cells.

The at least one pancreatic α, β and/or δ cell or precursor thereof can be produced according to any suitable culturing protocol to differentiate a stem cell or pluripotent cell to a desired stage of differentiation. In some embodiments, the at least one pancreatic α, β and/or δ cell or the precursor thereof are produced by culturing at least one pluripotent cell for a period of time and under conditions suitable for the at least one pluripotent cell to differentiate into the at least one pancreatic α, β and/or δ cell or the precursor thereof.

In some embodiments, the at least one pancreatic α, β and/or δ cell or precursor thereof is a substantially pure population of pancreatic α, β and/or δ cells or precursors thereof. In some embodiments, a population of pancreatic α, β and/or δ cells or precursors thereof comprises a mixture of pluripotent cells or differentiated cells. In some embodiments, a population pancreatic α, β and/or δ cells or precursors thereof are substantially free or devoid of embryonic stem cells or pluripotent cells or iPS cells.

In some embodiments, a somatic cell, e.g., fibroblast can be isolated from a subject, for example as a tissue biopsy, such as, for example, a skin biopsy, and reprogrammed into an induced pluripotent stem cell for further differentiation to produce the at least one pancreatic α, β and/or δ cell or precursor thereof for use in the compositions and methods described herein. In some embodiments, a somatic cell, e.g., fibroblast is maintained in culture by methods known by one of ordinary skill in the art, and in some embodiments, propagated prior to being converted into pancreatic α, β and/or δ cells by the methods as disclosed herein.

In some embodiments, the at least one pancreatic α, β and/or δ cell or precursor thereof are maintained in culture by methods known by one of ordinary skill in the art, and in some embodiments, propagated prior to being converted into pancreatic α, β and/or δ cells by the methods as disclosed herein.

Further, at least one pancreatic α, β and/or δ cell or precursor thereof, e.g., pancreatic progenitor can be from any mammalian species, with non-limiting examples including a murine, bovine, simian, porcine, equine, ovine, or human cell. For clarity and simplicity, the description of the methods herein refers to a mammalian at least one pancreatic α, β and/or δ cell or precursor thereof but it should be understood that all of the methods described herein can be readily applied to other cell types of at least one pancreatic α, β and/or δ cell or precursor thereof. In some embodiments, the at least one SC-β cell or precursor thereof is derived from a human individual.

Definitive Endoderm Cells

Aspects of the disclosure involve definitive endoderm cells. Definitive endoderm cells of use herein can be derived from any source or generated in accordance with any suitable protocol. In some aspects, pluripotent stem cells, e.g., iPSCs or hESCs, are differentiated to endoderm cells. In some aspects, the endoderm cells (stage 1) are further differentiated, e.g., to primitive gut tube cells (stage 2), PDX1-positive pancreatic progenitor cells (stage 3), NKX6.1-positive pancreatic progenitor cells (stage 4), or Ngn3-positive endocrine progenitor cells or insulin-positive endocrine cells (stage 5), followed by induction or maturation to SC-β cells (stage 6).

In some cases, definitive endoderm cells can be obtained by differentiating at least some pluripotent cells in a population into definitive endoderm cells, e.g., by contacting a population of pluripotent cells with i) at least one growth factor from the TGF-β superfamily, and ii) a WNT signaling pathway activator, to induce the differentiation of at least some of the pluripotent cells into definitive endoderm cells, wherein the definitive endoderm cells express at least one marker characteristic of definitive endoderm.

Any growth factor from the TGF-β superfamily capable of inducing the pluripotent stem cells to differentiate into definitive endoderm cells (e.g., alone, or in combination with a WNT signaling pathway activator) can be used in the method provided herein. In some cases, the growth factor from the TGF-β superfamily comprises Activin A. In some cases, the growth factor from the TGF-β superfamily comprises growth differentiating factor 8 (GDF8). Any WNT signaling pathway activator capable of inducing the pluripotent stem cells to differentiate into definitive endoderm cells (e.g., alone, or in combination with a growth factor from the TGF-β superfamily) can be used in the method provided herein. In some cases, the WNT signaling pathway activator comprises CHIR99Q21. In some cases, the WNT signaling pathway activator comprises Wnt3a recombinant protein.

In some cases, differentiating at least some pluripotent cells in a population into definitive endoderm cells is achieved by a process of contacting a population of pluripotent cells with i) Activin A, and ii) CH1R99021 for a suitable period of time, e.g., about 2 days, about 3 days, about 4 days, or about 5 days to induce the differentiation of at least some of the pluripotent cells in the population into definitive endoderm cells, wherein the definitive endoderm cells express at least one marker characteristic of definitive endoderm.

In some examples, the method comprises differentiating pluripotent cells into definitive endoderm cells by contacting a population of pluripotent cells with a suitable concentration of the growth factor from the TGF-β superfamily (e.g., Activin A), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some cases, the method comprises use of about 100 ng/mL Activin A for differentiation of pluripotent cells into definitive endoderm cells. In some cases, the method comprises use of about 200 ng/mL Activin A for differentiation of pluripotent cells into definitive endoderm cells.

In some examples, the method comprises differentiating pluripotent cells into definitive endoderm cells by contacting a population of pluripotent cells with a suitable concentration of the WNT signaling pathway activator (e.g., CHIR99021), such as, about 0.01 µM, about 0.05 µM, about 0.1 µM, about 0.2 µM, about 0.5 µM, about 0.8 µM, about 1 µM, about 1.5 µM, about 2 µM, about 2.5 µM, about 3 µM, about 3.5 µM, about 4 µM, about 5 µM, about 8 µM, about 10 µM, about 12 µM, about 15 µM, about 20 µM, about 30 µM, about 50 µM, about 100 µM, or about 200 µM. In some cases, the method comprises use of about 2 µM CHIR99021 for differentiation of pluripotent cells into definitive endoderm cells. In some cases, the method comprises use of about 5 µM CHIR99021 for differentiation of pluripotent cells into definitive endoderm cells.

In some cases, a definitive endoderm cell produced by the methods as disclosed herein expresses at least one marker selected from the group consisting of: Noda1, Tmprss2, Tmem30b, St14, Spink3, Sh3gl2, Ripk4, Rab1S, Npnt, Clic6, Cldn5, Cacna1b, Bnip1, Anxa4, Emb, FoxA1, Sox17, and Rbm35a, wherein the expression of at least one marker is upregulated to by a statistically significant amount in the definitive endoderm cell relative to the pluripotent stem cell from which it was derived. In some cases, a definitive endoderm cell produced by the methods as disclosed herein does not express by a statistically significant amount at least one marker selected the group consisting of: Gata4, SPARC, AFP and Dab2 relative to the pluripotent stem cell from which it was derived. In some cases, a definitive endoderm cell produced by the methods as disclosed herein does not express by a statistically significant amount at least one marker selected the group consisting of: Zic1, Pax6, Flk1 and CD31 relative to the pluripotent stem cell from which it was derived. In some cases, a definitive endoderm cell produced by the methods as disclosed herein has a higher level of phosphorylation of Smad2 by a statistically significant amount relative to the pluripotent stem cell from which it was derived. In some cases, a definitive endoderm cell produced by the methods as disclosed herein has the capacity to form gut tube in vivo. In some cases, a definitive endoderm cell produced by the methods as disclosed herein can differentiate into a cell with morphology characteristic of a gut cell, and wherein a cell with morphology characteristic of a gut cell expresses FoxA2 and/or Claudin6, In some cases, a definitive endoderm cell produced by the methods as disclosed herein can be further differentiated into a cell of endoderm origin.

In some cases, a population of pluripotent stem cells are cultured in the presence of at least one β cell differentiation factor prior to any differentiation or during the first stage of differentiation. One can use any pluripotent stem cell, such as a human pluripotent stem cell, or a human iPS cell or any of pluripotent stem cell as discussed herein or other suitable pluripotent stem cells. In some cases, a β cell differentiation factor as described herein can be present in the culture medium of a population of pluripotent stem cells or may be added in bolus or periodically during growth (e.g. replication or propagation) of the population of pluripotent stem cells. In certain examples, a population of pluripotent stem cells can be exposed to at least one β cell differentiation factor prior to any differentiation. In other examples, a population of pluripotent stem cells may be exposed to at least one β cell differentiation factor during the first stage of differentiation.

Primitive Gut Tube Cells

Aspects of the disclosure involve primitive gut tube cells. Primitive gut tube cells of use herein can be derived from any source or generated in accordance with any suitable protocol. In some aspects, definitive endoderm cells are differentiated to primitive gut tube cells. In some aspects, the primitive gut tube cells are further differentiated, e.g., to PDX1-positive pancreatic progenitor cells, NKX6.1-positive pancreatic progenitor cells, Ngn3-positive endocrine progenitor cells, insulin-positive endocrine cells, followed by induction or maturation to SC-β cells.

In some cases, primitive gut tube cells can be obtained by differentiating at least some definitive endoderm cells in a population into primitive gut tube cells, e.g., by contacting definitive endoderm cells with at least one growth factor from the fibroblast growth factor (FGF) family, to induce the differentiation of at least some of the definitive endoderm cells into primitive gut tube cells, wherein the primitive gut tube cells express at least one marker characteristic of primitive gut tube cells.

Any growth factor from the FGF family capable of inducing definitive endoderm cells to differentiate into primitive gut tube cells (e.g., alone, or in combination with other factors) can be used in the method provided herein. In some cases, the at least one growth factor from the FGF family comprises keratinocyte growth factor (KGF). In some cases, the at least one growth factor from the FGF family comprises FGF2. In some cases, the at least one growth factor from the FGF family comprises FGF8B. In some cases, the at least one growth factor from the FGF family comprises FGF 10. In some cases, the at least one growth factor from the FGF family comprises FGF21.

In some cases, primitive gut tube cells can be obtained by differentiating at least some definitive endoderm cells in a population into primitive gut tube cells, e.g., by contacting definitive endoderm cells with KGF for a certain period of time, e.g., about 1 day, about 2 days, about 3 days, or about 4 days, to induce the differentiation of at least some of the definitive endoderm cells into primitive gut tube cells.

In some cases, the method comprises differentiating definitive endoderm cells into primitive gut tube cells by contacting definitive endoderm cells with a suitable concentration of the growth factor from the FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL. In some cases, the method comprises use of about 50 ng/mL KGF for differentiation of definitive endoderm cells into primitive gut tube cells. In some cases, the method comprises use of about 100 ng/mL KGF for differentiation of definitive endoderm cells into primitive gut tube cells.

PDX1-Positive Pancreatic Progenitor Cells

Aspects of the disclosure involve PDX1-positive pancreatic progenitor cells. PDX1-positive pancreatic progenitor cells of use herein can be derived from any source or generated in accordance with any suitable protocol. In some aspects, primitive gut tube cells are differentiated to PDX1-positive pancreatic progenitor cells. In some aspects, the PDX1-positive pancreatic progenitor cells are further differentiated, e.g., NKX6.1-positive pancreatic progenitor cells, Ngn3-positive endocrine progenitor cells, insulin-positive endocrine cells, followed by induction or maturation to SC-β cells, In some aspects, PDX1-positive pancreatic progenitor cells can be obtained by differentiating at least some primitive gut tube cells in a population into PDX1-positive pancreatic progenitor cells, e.g., by contacting primitive gut tube cells with i) at least one BMP signaling pathway inhibitor, ii) a growth factor from TGF-β superfamily, iii) at least one growth factor from the FGF family, iv) at least one SHH pathway inhibitor, v) at least one retinoic acid (RA) signaling pathway activator; vi) at least one protein kinase C activator, and vii) ROCK inhibitor to induce the differentiation of at least some of the primitive gut tube cells into PDX1-positive pancreatic progenitor cells, wherein the PDX1-positive pancreatic progenitor cells express PDX1.

In some aspects, PDX1-positive pancreatic progenitor cells can be obtained by differentiating at least some primitive gut tube cells in a population into PDX1-positive pancreatic progenitor cells, e.g., by contacting primitive gut tube cells with i) at least one BMP signaling pathway inhibitor, ii) a growth factor from TGF-β superfamily, iii) at least one growth factor from the FGF family, iv) at least one SHH pathway inhibitor, v) at least one retinoic acid (RA) signaling pathway activator; and vi) at least one protein kinase C activator, to induce the differentiation of at least some of the primitive gut tube cells into PDX1-positive pancreatic progenitor cells, wherein the PDX1-positive pancreatic progenitor cells express PDX1.

In some cases, PDX1-positive pancreatic progenitor cells can be obtained by differentiating at least some primitive gut tube cells in a population into PDX1-positive pancreatic progenitor cells, e.g., by contacting primitive gut tube cells with i) at least one BMP signaling pathway inhibitor, ii) at least one growth factor from the FGF family, iii) at least one SHH pathway inhibitor, iv) at least one retinoic acid (RA) signaling pathway activator; and v) at least one protein kinase C activator, to induce the differentiation of at least some of the primitive gut tube cells into PDX1-positive pancreatic progenitor cells, wherein the PDX1-positive pancreatic progenitor cells express PDX1.

In some cases, PDX1-positive pancreatic progenitor cells can be obtained by differentiating at least some primitive gut tube cells in a population into PDX1-positive pancreatic progenitor cells, e.g., by contacting primitive gut tube cells with i) at least one SHH pathway inhibitor, ii) at least one retinoic acid (RA) signaling pathway activator; and iii) at least one protein kinase C activator, wherein the PDX1-positive pancreatic progenitor cells express PDX1.

In some cases, PDX1-positive pancreatic progenitor cells can be obtained by differentiating at least some primitive gut tube cells in a population into PDX1-positive pancreatic progenitor cells, e.g., by contacting primitive gut tube cells with i) at least one growth factor from the FGF family, and ii) at least one retinoic acid (RA) signaling pathway activator, to induce the differentiation of at least some of the primitive gut tube cells into PDX1-positive pancreatic progenitor cells, wherein the PDX1-positive pancreatic progenitor cells express PDX1.

Any BMP signaling pathway inhibitor capable of inducing primitive gut tube cells to differentiate into PDX1-positive pancreatic progenitor cells (e.g., alone, or with any combination of a growth factor from TGF-β superfamily, at least one growth factor from the FGF family, at least one SHH pathway inhibitor, at least one retinoic acid signaling pathway activator, at least one protein kinase C activator, and ROCK inhibitor) can be used in the method provided herein. In some cases, the BMP signaling pathway inhibitor comprises LDN193189 or DMH-1. In some examples, the method comprises contacting primitive gut tube cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 µM. In some examples, the method comprises contacting primitive gut tube cells with a concentration of BMP signaling pathway inhibitor (e.g., DMH-1), such as, about 0.01 µM, about 0.02 µM, about 0.05 µM, about 0.1 µM, about 0.2 µM, about 0.5 µM, about 0.8 µM, about 1 µM, about 1.2 µM, about 1.5 µM, about 1.7 µM, about 2 µM, about 2.2 µM, about 2.5 µM, about 2.75 µM, about 3 µM, about 3.25 µM, about 3.5 µM, about 3.75 µM, about 4 µM, about 4.5 µM, about 5 µM, about 8 µM, about 10 µM, about 15 µM, about 20 µM, about 30 µM, about 40 µM, about 50 µM, or about 100 µM.

Any growth factor from the TGF-β superfamily capable of inducing primitive gut tube cells to differentiate into PDX1-positive pancreatic progenitor cells (e.g., alone, or with any combination of at least one BMP signaling pathway inhibitor, a growth factor from the FGF family, at least one SHH pathway inhibitor, at least one retinoic acid signaling pathway activator, at least one protein kinase C activator, and ROCK inhibitor) can be used. In some cases, the growth factor from TGF-β family comprises Activin A. In some cases, the growth factor from TGF-β family comprises Activin A or GDF8. In some examples, the method comprises contacting primitive gut tube cells with a concentration of a growth factor from TGF-β superfamily (e.g., Activin A), such as, about 5 ng/mL, about 7.5 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 21 ng/mL, about 22 ng/mL, about 23 ng/mL, about 24 ng/mL, about 25 ng/mL, about 26 ng/mL, about 27 ng/mL, about 28 ng/mL, about 29 ng/mL, about 30 ng/mL, about 35 ng/mL, about 40 ng/mL, about 50 ng/mL, or about 100 ng/mL.

Any growth factor from the FGF family capable of inducing primitive gut tube cells to differentiate into PDX1-positive pancreatic progenitor cells (e.g., alone, or with any combination of at least one BMP signaling pathway inhibitor, a growth factor from TGF-β superfamily, at least one SHH pathway inhibitor, at least one retinoic acid signaling pathway activator, at least one protein kinase C activator, and ROCK inhibitor) can be used. In some cases, the at least one growth factor from the FGF family comprises keratinocyte growth factor (KGF). In some cases, the at least one growth factor from the FGF family is selected from the group consisting of FGF2, FGF8B, FGF 10, and FGF21. In some examples, the method comprises contacting primitive gut tube cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL.

Any SHH pathway inhibitor capable of inducing primitive gut tube cells to differentiate into PDX1-positive pancreatic progenitor cells (e.g., alone, or with any combination of at least one BMP signaling pathway inhibitor, at least one growth factor from the FGF family, a growth factor from TGF-β superfamily, at least one retinoic acid signaling pathway activator, at least one protein kinase C activator, and ROCK inhibitor) can be used. In some cases, the SHH pathway inhibitor comprises Sant1. In some examples, the method comprises contacting primitive gut tube cells with a concentration of a SHH pathway inhibitor (e.g., Sant1), such as, about 0.001 µM, about 0.002 µM, about 0.005 µM, about 0.01 µM, about 0.02 µM, about 0.03 µM, about 0.05 µM, about 0.08 µM, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM.

Any RA signaling pathway activator capable of inducing primitive gut tube cells to differentiate into PDX1-positive pancreatic progenitor cells (e.g., alone, or with any combination of at least one BMP signaling pathway inhibitor, at least one growth factor from the FGF family, at least one SHH pathway inhibitor, at least one protein kinase C activator, and ROCK inhibitor) can be used. In some cases, the RA signaling pathway activator comprises retinoic acid. In some examples, the method comprises contacting primitive gut tube cells with a concentration of an RA signaling pathway activator (e.g., retinoic acid), such as, about 0.02 µM, about 0.1 µM, about 0.2 µM, about 0.25 µM, about 0.3 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM.

Any PKC activator capable of inducing primitive gut tube cells to differentiate into PDX1-positive pancreatic progenitor cells (e.g., alone, or with any combination of at least one BMP signaling pathway inhibitor, at least one growth factor from the FGF family, at least one SHH pathway inhibitor, at least one RA signaling pathway activator, and ROCK inhibitor) can be used. In some cases, the PKC activator comprises PdBU. In some cases, the PKC activator comprises TPPB. In some examples, the method comprises contacting primitive gut tube cells with a concentration of a PKC activator (e.g., PdBU or TPPB), such as, about 10 nM, 50 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 10 µM, about 20 µM, about 50 µM, about 75 µM, about 80 µM, about 100 µM, about 120 µM, about 140 µM, about 150 µM, about 175 µM, about 180 µM, about 200 µM, about 210 µM, about 220 µM, about 240 µM, about 250 µM, about 260 µM, about 280 µM, about 300 µM, about 320 µM, about 340 µM, about 360 µM, about 380 µM, about 400 µM, about 420 µM, about 440 µM, about 460 µM, about 480 µM, about 500 µM, about 520 µM, about 540 µM, about 560 µM, about 580 µM, about 600 µM, about 620 µM, about 640 µM, about 660 µM, about 680 µM, about 700 µM, about 750 µM, about 800 µM, about 850 µM, about 900 µM, about 1 mM, about 2 mM, about 3 mM, about 4 mM, or about 5 mM. In some embodiments, the method comprises contacting primitive gut tube cells with a concentration of a PKC activator (e.g., PdBU or TPPB) of 10 nM-1 mM, 10 nM-500 µM, 10 nM-1 µM, 10-800 nM, 100-900 nM, 300-800 nM, 300-600 nM, 400-600 nM, 450-550 nM, or about 500 nM. In some embodiments, primitive gut tube cells are not treated with a PKC activator (e.g., PDBU).

Any ROCK inhibitor capable of inducing primitive gut tube cells to differentiate into PDX1-positive pancreatic progenitor cells (e.g., alone, or with any combination of at least one BMP signaling pathway inhibitor, at least one growth factor from the FGF family, at least one SHH pathway inhibitor, PKC activator, and at least one RA signaling pathway activator) can be used. In some cases, the ROCK inhibitor comprises Thiazovivin, Y-27632, Fasudil/HA1077, or H-1152. In some cases, the ROCK inhibitor comprises Y-27632. In some cases, the ROCK inhibitor comprises Thiazovivin. In some examples, the method comprises contacting primitive gut tube cells with a concentration of a ROCK inhibitor (e.g., Y-27632 or Thiazovivin), such as, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 µM.

In some cases, PDX1-positive pancreatic progenitor cells can be obtained by differentiating at least some primitive gut tube cells in a population into PDX1-positive pancreatic progenitor cells, e.g., by contacting primitive gut tube cells with retinoic acid, KGF, Sant1, DMH-1, PdBU, thiazovivin, and Activin A, for a suitable period of time, e.g., about 1 day, about 2 days, about 3 days, or about 4 days. In some cases, PDX1-positive pancreatic progenitor cells can be obtained by differentiating at least some primitive gut tube cells in a population into PDX1-positive pancreatic progenitor cells, e.g., by contacting primitive gut tube cells with retinoic acid, KGF, Sant1, DMH-1, PdBU, thiazovivin, and Activin A, for about 2 days.

NKX6.1-Positive Pancreatic Progenitor Cells

Aspects of the disclosure involve NKX6.1-positive pancreatic progenitor cells. NKX6.1-positive pancreatic progenitor cells of use herein can be derived from any source or generated in accordance with any suitable protocol. In some aspects, PDX1-positive pancreatic progenitor cells are differentiated to NKX6.1-positive pancreatic progenitor cells. In some aspects, the NKX6.1-positive pancreatic progenitor cells are further differentiated, e.g., to Ngn3-positive endocrine progenitor cells, or insulin-positive endocrine cells, followed by induction or maturation to SC-β cells.

In some aspects, a method of producing a NKX6.1-positive pancreatic progenitor cell from a PDX1-positive pancreatic progenitor cell comprises contacting a population of cells (e.g., under conditions that promote cell clustering and/or promoting cell survival) comprising PDX1-positive pancreatic progenitor cells with at least two β cell-differentiation factors comprising a) at least one growth factor from the fibroblast growth factor (FGF) family, b) a sonic hedgehog pathway inhibitor, and optionally c) a low concentration of a retinoic acid (RA) signaling pathway activator, to induce the differentiation of at least one PDX1-positive pancreatic progenitor cell in the population into NKX6.1- positive pancreatic progenitor cells, wherein the NKX6.1-positive pancreatic progenitor cells expresses NKX6.1.

In some cases, the PDX1-positive, NKX6.1-positive pancreatic progenitor cells are obtained by contacting PDX1-positive pancreatic progenitor cells with i) at least one growth factor from the FGF family, ii) at least one SHH pathway inhibitor, and optionally iii) a low concentration of a RA signaling pathway activator, to induce the differentiation of at least some of the PDX1-positive pancreatic progenitor cells into PDX1-positive, NKX6.1-positive pancreatic progenitor cells, wherein the PDX1-positive, NKX6.1-positive pancreatic progenitor cells expresses PDX1 and NKX6.1.

In some cases, the PDX1-positive, NKX6.1-positive pancreatic progenitor cells are obtained by contacting PDX1-positive pancreatic progenitor cells with i) at least one growth factor from the FGF family, ii) at least one SHH pathway inhibitor, and optionally iii) a low concentration of a RA signaling pathway activator, iv) ROCK inhibitor, and v) at least one growth factor from the TGF-β superfamily, to induce the differentiation of at least some of the PDX1-positive pancreatic progenitor cells into PDX1-positive, NKX6.1-positive pancreatic progenitor cells. In some embodiments, following 3, 4, or 5 days of contacting the PDX1-positive, NKX6.1-positive pancreatic progenitor cells are obtained by contacting PDX1-positive pancreatic progenitor cells with i) at least one growth factor from the FGF family, ii) at least one SHH pathway inhibitor, and optionally iii) a low concentration of a RA signaling pathway activator, iv) ROCK inhibitor, and v) at least one growth factor from the TGF-β superfamily; the cells are then contacted with i) at least one growth factor from the FGF family, ii) at least one SHH pathway inhibitor, and optionally iii) a low concentration of a RA signaling pathway activator, iv) ROCK inhibitor, and v) at least one growth factor from the TGF-β superfamily, and vi) a PKC activator and optionally a gamma-secretase inhibitor. In some cases, the PDX1-positive, NKX6.1-positive pancreatic progenitor cells are obtained by contacting PDX1-positive pancreatic progenitor cells under conditions that promote cell clustering with at least one growth factor from the FGF family. In some cases, the growth factor from the FGF family is KGF.

In some cases, the PDX1-positive pancreatic progenitor cells are produced from a population of pluripotent cells. In some cases, the PDX1-positive pancreatic progenitor cells are produced from a population of iPS cells. In some cases, the PDX1-positive pancreatic progenitor cells are produced from a population of ESC cells. In some cases, the PDX1-positive pancreatic progenitor cells are produced from a population of definitive endoderm cells. In some cases, the PDX1-positive pancreatic progenitor cells are produced from a population of primitive gut tube cells.

Any growth factor from the FGF family capable of inducing PDX1-positive pancreatic progenitor cells to differentiate into NKX6.1-positive pancreatic progenitor cells (e.g., alone, or with any combination of at least one SHH pathway inhibitor, a ROCK inhibitor, a growth factor from the TGF-β superfamily, and at least one retinoic acid signaling pathway activator) can be used in the method provided herein. In some cases, the at least one growth factor from the FGF family comprises keratinocyte growth factor (KGF). In some cases, the at least one growth factor from the FGF family is selected from the group consisting of FGF8B, FGF 10, and FGF21. In some examples, the method comprises contacting PDX1-positive pancreatic progenitor cells with a concentration of a growth factor from FGF family (e.g., KGF), such as, about 10 ng/mL, about 20 ng/mL, about 50 ng/mL, about 75 ng/mL, about 80 ng/mL, about 90 ng/mL, about 95 ng/mL, about 100 ng/mL, about 110 ng/mL, about 120 ng/mL, about 130 ng/mL, about 140 ng/mL, about 150 ng/mL, about 175 ng/mL, about 180 ng/mL, about 200 ng/mL, about 250 ng/mL, or about 300 ng/mL.

Any SHH pathway inhibitor capable of inducing PDX1-positive pancreatic progenitor cells to differentiate into NKX6.1-positive pancreatic progenitor cells (e.g., alone, or with any combination of at least one growth factor from the FGF family, at least one retinoic acid signaling pathway activator, ROCK inhibitor, and at least one growth factor from the TGF-β superfamily) can be used in the method provided herein. In some cases, the SHH pathway inhibitor comprises Sant1. In some examples, the method comprises contacting PDX1-positive pancreatic progenitor cells with a concentration of a SHH pathway inhibitor (e.g., Sant1), such as, about 0.001 μM, about 0.002 μM, about 0.005 μM, about 0.01 μM, about 0.02 μM, about 0.03 μM, about 0.05 μM, about 0.08 μM, about 0.1 μM, about 0.12 μM, about 0.13 μM, about 0.14 μM, about 0.15 μM, about 0.16 μM, about 0.17 μM, about 0.18 μM, about 0.19 μM, about 0.2 μM, about 0.21 μM, about 0.22 μM, about 0.23 μM, about 0.24 μM, about 0.25 μM, about 0.26 μM, about 0.27 μM, about 0.28 μM, about 0.29 μM, about 0.3 μM, about 0.31 μM, about 0.32 μM, about 0.33 μM, about 0.34 μM, about 0.35 μM, about 0.4 μM, about 0.45 μM, about 0.5 μM, about 0.6 μM, about 0.8 μM, about 1 μM, about 2 μM, or about 5 μM.

Any RA signaling pathway activator capable of inducing PDX1-positive pancreatic progenitor cells to differentiate into NKX6.1-positive pancreatic progenitor cells (e.g., alone, or with any combination of at least one growth factor from the FGF family, at least one SHH pathway inhibitor, ROCK inhibitor, and at least one growth factor from the TGF-β superfamily) can be used. In some cases, the RA signaling pathway activator comprises retinoic acid. In some examples, the method comprises contacting PDX1-positive pancreatic progenitor cells with a concentration of an RA signaling pathway activator (e.g., retinoic acid), such as, about 0.02 μM, about 0.1 μM, about 0.2 μM, about 0.25 μM, about 0.3 μM, about 0.4 μM, about 0.45 μM, about 0.5 μM, about 0.55 μM, about 0.6 μM, about 0.65 μM, about 0.7 μM, about 0.75 μM, about 0.8 μM, about 0.85 μM, about 0.9 μM, about 1 μM, about 1.1 μM, about 1.2 μM, about 1.3 μM, about 1.4 μM, about 1.5 μM, about 1.6 μM, about 1.7 μM, about 1.8 μM, about 1.9 μM, about 2 μM, about 2.1 μM, about 2.2 μM, about 2.3 μM, about 2.4 μM, about 2.5 μM, about 2.6 μM, about 2.7 μM, about 2.8 μM, about 3 μM, about 3.2 μM, about 3.4 μM, about 3.6 μM, about 3.8 μM, about 4 μM, about 4.2 μM, about 4.4 μM, about 4.6 μM, about 4.8 μM, about 5 μM, about 5.5 μM, about 6 μM, about 6.5 μM, about 7 μM, about 7.5 μM, about 8 μM, about 8.5 μM, about 9 μM, about 9.5 μM, about 10 μM, about 12 μM, about 14 μM, about 15 μM, about 16 μM, about 18 μM, about 20 μM, about 50 μM, or about 100 μM.

Any ROCK inhibitor capable of inducing PDX1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and at least one growth factor from the TGF-β superfamily) can be used. In some cases, the ROCK inhibitor comprises Thiazovivin, Y-27632, Fasudil/HA1077, or 14-1152. In some examples, the method comprises contacting PDX1-positive pancreatic progenitor cells with a concentration of a ROCK inhibitor (e.g., Y-27632 or Thiazovivin), such as about 0.2 μM, about 0.5 μM, about 0.75

μM, about 1 μM, about 2 μM, about 3 μM, about 4 μM, about 5 μM, about 6 μM, about 7 μM, about 7.5 μM, about 8 μM, about 9 μM, about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 26 μM, about 27 μM, about 28 μM, about 29 μM, about 30 μM, about 35 μM, about 40 μM, about 50 μM, or about 100 μM.

Any activator from the TGF-β superfamily capable of inducing PDX1-positive pancreatic progenitor cells to differentiate into NKX6.1-positive pancreatic progenitor cells (e.g., alone, or with any combination of at least one growth factor from the FGF family, at least one SHH pathway inhibitor, a RA signaling pathway activator, and ROCK inhibitor) can be used. In some cases, the activator from the TGF-β superfamily comprises Activin A or GDF8. In some examples, the method comprises contacting PDX1-positive pancreatic progenitor cells with a concentration of a growth factor from TGF-β superfamily (e.g., Activin A), such as, about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 1 ng/mL, about 1.2 ng/mL, about 1.4 ng/mL, about 1.6 ng/mL, about 1.8 ng/mL, about 2 ng/mL, about 2.2 ng/mL, about 2.4 ng/mL, about 2.6 ng/mL, about 2.8 ng/mL, about 3 ng/mL, about 3.2 ng/mL, about 3.4 ng/mL, about 3.6 ng/mL, about 3.8 ng/mL, about 4 ng/mL, about 4.2 ng/mL, about 4.4 ng/mL, about 4.6 ng/mL, about 4.8 ng/mL, about 5 ng/mL, about 5.2 ng/mL, about 5.4 ng/mL, about 5.6 ng/mL, about 5.8 ng/mL, about 6 ng/mL, about 6.2 ng/mL, about 6.4 ng/mL, about 6.6 ng/mL, about 6.8 ng/mL, about 7 ng/mL, about 8 ng/mL, about 9 ng/mL, about 10 ng/mL, about 20 ng/mL, about 30 ng/mL, or about 50 ng/mL. In some examples, the method comprises contacting PDX1-positive pancreatic progenitor cells with a concentration of a growth factor from TGF-β superfamily (e.g., Activin A), such as, about 5 ng/mL.

In some cases, the PDX1-positive, NKX6.1-positive pancreatic progenitor cells are obtained by contacting PDX1-positive pancreatic progenitor cells under conditions that promote cell clustering with KGF, Sant1, and RA, for a period of 5 days or 6 days. In some cases, the PDX1-positive, NKX6.1-positive pancreatic progenitor cells are obtained by contacting PDX1-positive pancreatic progenitor cells under conditions that promote cell clustering with KGF, Sant1, RA, thiazovivin, and Activin A, for a period of 5 or 6 days. In some cases, the PDX1-positive, NKX6.1-positive pancreatic progenitor cells are obtained by contacting PDX1-positive pancreatic progenitor cells under conditions that promote cell clustering with KGF for a period of 5 days. In some embodiments, the PDX1-positive, NKX6.1-positive pancreatic progenitor cells are obtained by: a) contacting PDX1-positive pancreatic progenitor cells with KGF, Sant1, RA, thiazovivin, and Activin A, for a period of 3, 4 or 5 days, followed by; b) contacting the cells of a) with PDBU, XXI, KGF, Sant1, RA, thiazovivin, and Activin A for a period of 1, 2 or 3 days.

Insulin Positive Endocrine Cells

Aspects of the disclosure involve insulin-positive endocrine cells (e.g., NKX6.1-positive, ISL1-positive cells, or β-like cells). Insulin-positive endocrine cells of use herein can be derived from any source or generated in accordance with any suitable protocol, In some aspects, NKX6.1-positive pancreatic progenitor cells are differentiated to insulin-positive endocrine cells (e.g., NKX6.1-positive, ISL1-positive cells, or β-like cells), In some aspects, the insulin-positive endocrine cells are further differentiated, e.g., by induction or maturation to SC-β cells.

In some aspects, a method of producing an insulin-positive endocrine cell from an NKX6.1-positive pancreatic progenitor cell comprises contacting a population of cells (e.g., under conditions that promote cell clustering) comprising NKX6-1-positive pancreatic progenitor cells with a) a TGF-β signaling pathway inhibitor, and b) a thyroid hormone signaling pathway activator, to induce the differentiation of at least one NKX6.1-positive pancreatic progenitor cell in the population into an insulin-positive endocrine cell, wherein the insulin-positive endocrine ceil expresses insulin. In some cases, insulin-positive endocrine cells express PDX1, NKX6.1, ISL1, NKX2.2, Mafb, glis3, Sur1, Kir6.2, Znt8, SLC2A1, SLC2A3 and/or insulin.

Any TGF-β signaling pathway inhibitor capable of inducing the differentiation of NKX6.1-positive pancreatic progenitor cells to differentiate into insulin-positive endocrine cells (e.g., alone, or in combination with other β cell-differentiation factors, e.g., a thyroid hormone signaling pathway activator) can be used. In some cases, the TGF-β signaling pathway comprises TGF-β receptor type I kinase signaling. In some cases, the TGF-β signaling pathway inhibitor comprises Alk5 inhibitor II.

Any thyroid hormone signaling pathway activator capable of inducing the differentiation of NKX6.1-positive pancreatic progenitor cells to differentiate into insulin-positive endocrine cells (e.g., alone, or in combination with other β cell-differentiation factors, e.g., a TGF-β signaling pathway inhibitor) can be used. In some cases, the thyroid hormone signaling pathway activator comprises triiodothyronine (T3). In some cases, the thyroid hormone signaling pathway activator comprises GC-1.

In some cases, the method comprises contacting the population of cells (e.g., NKX6.1-positive pancreatic progenitor cells) with at least one additional factor. In some cases, the method comprises contacting the PDX1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) a protein kinase inhibitor, vi) a TGF-β signaling pathway inhibitor, or vii) a thyroid hormone signaling pathway activator. In some embodiments, the method comprises contacting the population of cells (e.g., NKX6.1-positive pancreatic progenitor cells) with at least one additional factor. In some cases, the method comprises contacting the PDX1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) a protein kinase inhibitor, vi) a TGF-β signaling pathway inhibitor, vii) a thyroid hormone signaling pathway activator, or viii) a PKC activator.

In some cases, the method comprises contacting the PDX1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) a protein kinase inhibitor, or ix) a ROCK inhibitor.

In some cases, the method comprises contacting the PDX1-positive NKX6.1-positive pancreatic progenitor cells with at least one of i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound, ix) a protein kinase inhibitor, or x) a ROCK inhibitor.

In some embodiments, in the method of generating the insulin-positive endocrine cells from the PDX1-positive NKX6.1-postive pancreatic progenitor cells, some of the differentiation factors are present only for the first 1, 2, 3, 4, or 5 days during the differentiation step. In some cases, some of the differentiation factors, such as the SHH pathway inhibitor, the RA signaling pathway activator, the PKC activator, and the at least one growth factor from the EGF family are removed from the culture medium after the first 1, 2, or 3 days of incubation.

Any γ-secretase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator). In some cases, the γ-secretase inhibitor comprises XXI. In some cases, the γ-secretase inhibitor comprises DAPT. In some examples, the method comprises contacting NKX6.1-positive pancreatic progenitor cells with a concentration of a γ-secretase inhibitor (e.g., XXI), such as, about 0.01 µM, about 0.02 µM, about 0.05 µM, about 0.075 µM, about 0.1 µM, about 0.2 µM, about 0.3 µM, about 0.4 µM, about 0.5 µM, about 0.6 µM, about 0.7 µM, about 0.8 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 2.9 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.2 µM, about 5.4 µM, about 5.6 µM, about 5.8 µM, about 6 µM, about 6.2 µM, about 6.4 µM, about 6.6 µM, about 6.8 µM, about 7 µM, about 8 µM, about 9 µM, about 10 µM, about 20 µM, about 30 µM, or about 50 µM.

Any growth factor from the EGF family capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some cases, the at least one growth factor from the EGF family comprises betacellulin. In some cases, at least one growth factor from the EGF family comprises EGF. In some examples, the method comprises contacting NKX6.1-positive pancreatic progenitor cells with a concentration of a growth factor from EGF family (e.g., betacellulin), such as, about 1 ng/mL, about 2 ng/mL, about 4 ng/mL, about 6 ng/mL, about 8 ng/mL, about 10 ng/mL, about 12 ng/mL, about 14 ng/mL, about 16 ng/mL, about 18 ng/mL, about 20 ng/mL, about 22 ng/mL, about 24 ng/mL, about 26 ng/mL, about 28 ng/mL, about 30 ng/mL, about 40 ng/mL, about 50 ng/mL, about 75 ng/mL, about 80 ng/mL, about 90 ng/mL, about 95 ng/mL, about 100 ng/mL, about 150 ng/mL, about 200 ng/mL, about 250 ng/mL, or about 300 ng/mL.

Any RA signaling pathway activator capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some cases, the RA signaling pathway activator comprises RA. In some examples, the method comprises contacting NKX6.1-positive pancreatic progenitor cells with a concentration of an RA signaling pathway activator (e.g., retinoic acid), such as, about 0.02 µM, about 0.1 µM, about 0.2 µM, about 0.25 µM, about 0.3 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 1 µM, about 1.1 µM, about 1.2 µM, about 1.3 µM, about 1.4 µM, about 1.5 µM, about 1.6 µM, about 1.7 µM, about 1.8 µM, about 1.9 µM, about 2 µM, about 2.1 µM, about 2.2 µM, about 2.3 µM, about 2.4 µM, about 2.5 µM, about 2.6 µM, about 2.7 µM, about 2.8 µM, about 3 µM, about 3.2 µM, about 3.4 µM, about 3.6 µM, about 3.8 µM, about 4 µM, about 4.2 µM, about 4.4 µM, about 4.6 µM, about 4.8 µM, about 5 µM, about 5.5 µM, about 6 µM, about 6.5 µM, about 7 µM, about 7.5 µM, about 8 µM, about 8.5 µM, about 9 µM, about 9.5 µM, about 10 µM, about 12 µM, about 14 µM, about 15 µM, about 16 µM, about 18 µM, about 20 µM, about 50 µM, or about 100 µM.

Any SHH pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used in the method provided herein. In some cases, the SHH pathway inhibitor comprises Sant1. In some examples, the method comprises contacting NKX6.1-positive pancreatic progenitor cells with a concentration of a SHH pathway inhibitor (e.g., Sand), such as, about 0.001 µM, about 0.002 µM, about 0.005 µM, about 0.01 µM, about 0.02 µM, about 0.03 µM, about 0.05 µM, about 0.08 µM, about 0.1 µM, about 0.12 µM, about 0.13 µM, about 0.14 µM, about 0.15 µM, about 0.16 µM, about 0.17 µM, about 0.18 µM, about 0.19 µM, about 0.2 µM, about 0.21 µM, about 0.22 µM, about 0.23 µM, about 0.24 µM, about 0.25 µM, about 0.26 µM, about 0.27 µM, about 0.28 µM, about 0.29 µM, about 0.3 µM, about 0.31 µM, about 0.32 µM, about 0.33 µM, about 0.34 µM, about 0.35 µM, about 0.4 µM, about 0.45 µM, about 0.5 µM, about 0.6 µM, about 0.8 µM, about 1 µM, about 2 µM, or about 5 µM.

Any BMP signaling pathway inhibitor capable of inducing the differentiation of NKX6.1-positive pancreatic progenitor cells to differentiate into insulin-positive endocrine cells (e.g., alone, or in combination with any of a TGF-β signaling pathway inhibitor and/or a thyroid hormone signaling pathway activator) can be used. In some cases, the BMP signaling pathway inhibitor comprises LDN193189 or DMH-1. In some examples, the method comprises contacting NKX6.1-positive pancreatic progenitor cells with a concentration of BMP signaling pathway inhibitor (e.g., LDN1931189), such as, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 280 nM, about 300 nM, about 400 nM, about 500 nM, or about 1 µM.

Any ROCK inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some cases, the ROCK inhibitor comprises Thiazovivin, Y-27632, Fasudil/HA1077, or H-1152. In some cases, the ROCK inhibitor comprises Y-27632. In some cases, the ROCK inhibitor comprises Thiazovivin. In some examples, the method comprises contacting PDX1-positive, NKX6.1-positive pancreatic progenitor cells with a concentration of a ROCK inhibitor (e.g., Y-27632 or Thiazovivin), such as, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 35 µM, about 40 µM, about 50 µM, or about 100 µM.

Any epigenetic modifying compound that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator) can be used. In some cases, the epigenetic modifying compound comprises a histone methyltransferase inhibitor or a HDAC inhibitor. In some cases, the epigenetic modifying compound comprises a histone methyltransferase inhibitor, e.g., DZNep. In some cases, the epigenetic modifying compound comprises a HDAC inhibitor, e.g., KD5170. In some examples, the method comprises contacting PDX1-positive, NKX6.1-positive pancreatic progenitor cells with a concentration of an epigenetic modifying compound (e.g., DZNep or KD5170), such as, about 0.01 µM, about 0.025 µM, about 0.05 µM, about 0.075 µM, about 0.1 µM, about 0.15 µM, about 0.2 µM, about 0.5 µM, about 0.75 µM, about 1 µM, about 2 µM, about 3 µM, about 4 µM, about 5 µM, about 6 µM, about 7 µM, about 7.5 µM, about 8 µM, about 9 µM, about 10 µM, about 15 µM, about 20 µM, about 25 µM, about 30 µM, about 35 µM, about 40 µM, about 50 µM, or about 100 µM.

In some cases, the population of cells is optionally contacted with a protein kinase inhibitor. In some cases, the population of cells is not contacted with the protein kinase inhibitor. In some cases, the population of cells is contacted with the protein kinase inhibitor. Any protein kinase inhibitor that is capable of inducing the differentiation of NKX6.1-positive pancreatic progenitor cells in a population into insulin-positive endocrine cells (e.g., alone, or in combination with any of a TGF-β signaling pathway inhibitor and/or a thyroid hormone signaling pathway activator). In some cases, the protein kinase inhibitor comprises staurosporine.

In some cases, the method comprises contacting the population of cells (e.g., NKX6.1-positive pancreatic progenitor cells) with XXI, Alk5i, T3 or GC-1, RA, Sant1, and betacellulin for a period of 7 days, to induce the differentiation of at least one NKX6.1-positive pancreatic progenitor cell in the population into an insulin-positive endocrine cell, wherein the insulin-positive endocrine cell expresses insulin. In some cases, the method comprises contacting the population of cells (e.g., NKX6.1-positive pancreatic progenitor cells) with XXI, Alk5i, T3 or GC-1, RA, Sant1, betacellulin, and LDN193189 for a period of 7 days, to induce the differentiation of at least one NKX6.1-positive pancreatic progenitor cell in the population into an insulin-positive endocrine cell, wherein the insulin-positive endocrine cell expresses insulin. In some embodiments, one or more differentiation factors are added in a portion of the Stage 5, for instance, only the first 1, 2, 3, 4, 5, or 6 days of the period of time for Stage 5, or the last 1, 2, 3, 4, 5, or 6 days of the period of time for Stage 5. In one example, the cells are contacted with SHH signaling pathway inhibitor for only the first 2, 3, 4, or 5 days during Stage 5, after which the SHH signaling pathway inhibitor is removed from the culture medium. In another example, the cells are contacted with BMP signaling pathway inhibitor for only the first 1, 2, or 3 days during Stage 5, after which the BMP signaling pathway inhibitor is removed from the culture medium.

In some cases, the method comprises culturing the population of cells (e.g., NKX6.1-positive pancreatic progenitor cells) in a BE5 medium, to induce the differentiation of at least one NKX6.1-positive pancreatic progenitor cell in the population into an insulin-positive endocrine cell, wherein the insulin-positive endocrine cell expresses insulin.

Aspects of the disclosure involve treatment of cell population comprising PDX1-positive, NKX6.1-positive pancreatic progenitor cells with PKC activator, which can lead to increase in percentage of pancreatic α cells, increase in percentage of pancreatic δ cells, increase in percentage of pancreatic β cells, reduction in percentage of EC cells, or any combination thereof, in the cell population of pancreatic endocrine cells generated according to the method disclosed herein.

In some cases, the method comprises contacting a population of cells comprising PDX1-positive, NKX6.1-positive pancreatic progenitor cells with a first composition comprising the PKC activator, a ROCK inhibitor, a growth factor from TGFβ superfamily, a growth factor from FGF family, a RA signaling pathway activator, and a SHH pathway inhibitor, for one to two days, thereby obtaining a first transformation cell population comprising PDX1-positive, NKX6.1-positive pancreatic progenitor cells; and contacting the first transformation cell population comprising PDX1-positive, NKX6.1-positive pancreatic progenitor cells with a second composition comprising the PKC activator, a TGF-β signaling pathway inhibitor, a TH signaling pathway activator, and an epigenetic modifying compound, for one to two days, thereby obtaining a second transformation cell population comprising NKX6.1-positive, ISL1-positive endocrine cells.

In some cases, the method comprises (1) contacting PDX1-positive pancreatic progenitor cells with i) at least one growth factor from the FGF family, ii) at least one SHH pathway inhibitor, and optionally iii) a low concentration of a RA signaling pathway activator, iv) ROCK inhibitor, and v) at least one growth factor from the TGF-β superfamily, for about two to six days, to induce the differentiation of at least some of the PDX1-positive pancreatic progenitor cells into PDX1-positive, NKX6.1-positive pancreatic progenitor cells; and (2) after (1) contacting the population comprising the PDX1-positive, NKX6.1-positive pancreatic progenitor cells with i) at least one growth factor from the FGF family, ii) at least one SHH pathway inhibitor, iii) a low concentration of a RA signaling pathway activator, iv) ROCK inhibitor, v) at least one growth factor from the TGF-β superfamily, and vi) a PKC activator, for one to two days, thereby generating a first transformation cell population comprising PDX1-positive, NKX6.1-positive pancreatic progenitor cells.

In some cases, the method further comprises: (3) contacting first transformation cell population comprising PDX1-positive, NKX6.1-positive pancreatic progenitor cells with i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound, ix) a protein kinase inhibitor, x) a ROCK inhibitor, and xi) a PKC activator, for one to two days, thereby generating a second transformation cell population; and (4) contacting the second transformation cell population with i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound, ix) a protein kinase inhibitor, and x) a ROCK inhibitor, thereby generating a cell population comprising NKX6.1-positive, ISL1-positive endocrine cells.

Pancreatic β Cells

Aspects of the disclosure involve generating pancreatic β cells (e.g., non-native pancreatic β cells). Non-native pancreatic β cells, in some cases, resemble endogenous mature β cells in form and function, but nevertheless are distinct from native β cells.

In some cases, the insulin-positive pancreatic endocrine cells generated using the method provided herein can form a cell cluster, alone or together with other types of cells, e.g., precursors thereof, e.g., stem cell, definitive endoderm cells, primitive gut tube cell, PDX1-positive pancreatic progenitor cells, or NKX6.1-positive pancreatic progenitor cells.

In some embodiments, any of the cells or populations of cells disclosed herein are in a cell cluster. In some aspects, provided herein are cell clusters that resemble the functions and characteristics of endogenous pancreatic islets. Such cell clusters can mimic the function of endogenous pancreatic islets in regulating metabolism, e.g., glucose metabolism in a subject. Thus, the cell clusters can be transplanted to a subject for treating disease resulting from insufficient pancreatic islet function, e.g., diabetes. The terms "cluster" and "aggregate" can be used interchangeably, and refer to a group of cells that have close cell-to-cell contact, and in some cases, the cells in a cluster can be adhered to one another. A cell cluster comprises a plurality of cells. In some embodiments, a cell cluster comprises at least 10, at least 50, at least 200, at least 500, at least 750, at least 1000, at least 1500, at least 2000, at least 2500, at least 3000, at least 3500, at least 4000, at least 4500, at least 5000, at least 6000, at least 7000, at least 8000, at least 9000, at least 10,000, at least 20,000, at least 30,000, or at least 50,000 cells. In some embodiments, a cell cluster comprises between 10-10,000 cells, between 50-10,000, between 100-10,000, between 100-10,000, between 1,000-10,000, between 500 and 10,000, between 500 and 5,000, between 500 and 2,500, between 500 and 2,000, between 1,000 and 100,000, between 1,000 and 50,000, between 1,000 and 40,000, between 1,000 and 20,000, between 1,000 and 10,000, between 1,000 and 5,000 and between 1,000 and 3,000 cells. In some embodiments, a cell cluster comprises at least 500 cells. In some embodiments, a cell cluster comprises at least 1,000 cells. In some embodiments, a cell cluster comprises at least 2,000 cells. In some embodiments, a cell cluster comprises at least 5,000 cells. In some embodiments, a cell cluster comprises no more than 100,000, no more than 90,000, no more than 80,000, no more than 70,000, no more than 60,000, no more than 50,000, no more than 40,000, no more than 30,000, no more than 20,000, no more than 10,000, no more than 7,000, no more than 5,000, no more than 3,000, no more than 2,000 cells, or no more than 1,000 cells.

A cell cluster can be in a size similar to an endogenous pancreatic islet. For example, a cell cluster can have a diameter similar to an endogenous pancreatic islet. A diameter of a cell cluster can refer to the largest linear distance between two points on the surface of the cell cluster. In some cases, the diameter of a cell cluster is at most 300 μm, 200 μm, 150 μm, 100 μm, 90 μm, 80 μm, 70 μm, 60 μm, 50 μm, or 40 μm. The diameter of a cell cluster can be from about 75 μm to about 250 μm. The diameter of a cell cluster can be at most 100 μm.

In some embodiments, a cell cluster is between about 100 and about 250 microns in diameter (e.g., about 125, about 140, about 150, about 160, about 170, about 180, about 190, about 200, about 200, about 210, about 215, about 220, or about 225, microns in diameter). For example, in some embodiments, the cell cluster is between about 125 and about 225, between about 130 and about 160, between about 170 and about 225, between about 140 and about 200, between about 140 and about 170, between about 160 and about 220, between about 170 and about 215, or between about 170 and about 200, microns in diameter.

In some embodiments, a composition, cell or cell population of the present disclosure comprises cells having a genomic disruption in at least one gene sequence. In some embodiments, the genomic disruption reduces or eliminates expression of a protein encoded by said gene sequence. In some embodiments, the at least one gene sequence encodes an MHC-Class I gene. In some embodiments, the MHC-Class I gene encodes beta-2 microglobulin, HLA-A, HLA-B, or HLA-C. In some embodiments, the at least one gene sequence encodes for CIITA. For example, in some embodiments, the composition or cell population has a genomic disruption in the beta-2-microglobulin gene. Additional examples of genes and genomic disruptions thereof are described in more detail in International Publication No. WO2020/033879, the relevant content of which is incorporated herein by reference. In some embodiments, the genomic disruption is induced using a gene editing technology (e.g., CRISPR Cas).

In some embodiments, a composition or cell population of the present disclosure comprises NKX6.1-positive, ISL-positive cells that express lower levels of MAFA than NKX6.1-positive, ISL-positive cells from the pancreas of a healthy control adult subject. In some embodiments, the composition or cell population comprises NKX6.1-positive, ISL-positive cells that express higher levels of MAFB than NKX6.1-positive, ISL-positive cells from the pancreas of a healthy control adult subject. In some embodiments, the composition or cell population comprises NKX6.1-positive, ISL-positive cells that express higher levels of SIX2, HOPX, IAPP and/or UCN3 than NKX6.1-positive, ISL-positive cells from the pancreas of a healthy control adult subject.

In some embodiments, a composition or cell population of the present disclosure comprises NKX6.1-positive, ISL-positive cells that do not express MAFA. In some embodiments, the composition or cell population comprises NKX6.1-positive, ISL-positive cells that express MAFB.

In some cases, the cell population comprising the insulin-positive endocrine cells can be directly induced to mature into SC-β cells without addition of any exogenous differentiation factors (such as inhibitor of TGF-β signaling pathway, thyroid hormone signaling pathway activator, PKC activator, growth factors from TGF-β superfamily, FGF family, or EGF family, SHH signaling pathway inhibitor, γ-secretase inhibitor, ROCK inhibitor, or BMP signaling pathway inhibitor). In some embodiments, the method provided herein comprises contacting a cell population comprising NKX6.1-positive, ISL1-positive endocrine cells with a serum albumin protein, a TGF-β signaling pathway inhibitor, a SHH pathway inhibitor, a TH signaling pathway activator, a protein kinase inhibitor, a ROCK inhibitor, a BMP signaling pathway inhibitor, and/or an epigenetic modifying compound. In some embodiments, the method provided herein comprises contacting a cell population comprising NKX6.1-positive, ISL1-positive endocrine cells with human serum albumin protein. In some embodiments, the method provided herein comprises contacting a cell population comprising NKX6.1-positive, ISL1-positive endocrine cells with a PKC activator.

In some cases, the cell population comprising the insulin-positive endocrine cells can be induced to mature into SC-β cells by contacting the insulin-positive endocrine cells with differentiation factors. The differentiation factors can comprise at least one inhibitor of TGF-β signaling pathway and thyroid hormone signaling pathway activator as described herein. In some cases, SC-β cells can be obtained by contacting a population of cells comprising insulin-positive endocrine cells with Alk5i and T3 or GC-1.

In some cases, the method provided herein comprises contacting a cell population comprising NKX6.1-positive, ISL1-positive endocrine cells with (i) a growth factor from the FGF family, (ii) a TGF-β signaling pathway inhibitor, (iii) a thyroid hormone signaling pathway activator, (iv) an epigenetic modifying compound, (v) a protein kinase inhibitor, (vi) a ROCK inhibitor, (vii) a BMP signaling pathway inhibitor, and (viii) a lipase inhibitor for about one two five days. In some cases, the contacting is for about three days.

In some examples, insulin-positive endocrine cells can be matured in a NS-GFs medium, MCDB131 medium, DMEM medium, or CMRL medium. In some cases, the insulin-positive endocrine cells can be matured in a CMRLs medium supplemented with 10% FBS. In some cases, the insulin-positive endocrine cells can be matured in a DMEM/F12 medium supplemented with 1% HSA. In other cases, SC-β cells can be obtained by culturing the population of cells containing the insulin-positive endocrine cells in a MCDB131 medium that can be supplemented by 2% BSA. In some cases, the MCDB131 medium with 2% BSA for maturation of insulin-positive endocrine cells into SC-β cells can be comprise no small molecule factors as described herein. In some case, the MCDB131 medium with 2% BSA for maturation of insulin-positive endocrine cells into SC-β cells can comprise no serum (e.g., no FBS). In other cases, SC-β cells can be obtained by culturing the population of cells containing the insulin-positive endocrine cells in a MCDB131 medium that can be supplemented by 0.05% HSA and vitamin C In some cases, SC-β cells can be obtained by culturing the population of cells containing the insulin-positive endocrine cells in a MCDB131 medium that can be supplemented by 0.05% HSA, ITS-X, vitamin C, and glutamine (Gln, e.g., 4 mM). In some cases, the type of culture medium may be changed during S6. For instance, the S6 cells are cultured in a MCDB131 medium that can be supplemented by 0.05% HSA and vitamin C for the first two to four days, and then followed by a DMEM/F12 medium supplemented with 1% HSA. In some cases, additional factors are introduced into the culture medium. For instance, S6 cells can be cultured in a MCDB131 medium that can be supplemented by 0.05% HSA, ITS-X, vitamin C, and glutamine (Gln, e.g., 4 mM) throughout the 10-12 days, during which $ZnSO_4$ is introduced from day 4 of S6.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into PDX1-positive pancreatic progenitor cells by a process of contacting the primitive gut tube cells with i)retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the PDX1-positive pancreatic progenitor cells into PDX1-positive, NKX6.1-positive pancreatic progenitor cells by a process of contacting the PDX1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, for a period of 5 days; e) differentiating at least some of the PDX1-positive, NKX6.1-positive pancreatic progenitor cells into PDX1-positive, NKX6.1-positive, insulin-positive endocrine cells by a process of contacting the PDX1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, optionally vi) at least one growth factor from the epidermal growth factor (EGF) family, and optionally vii) a BMP signaling pathway inhibitor, for a period of between five and seven days; and f) differentiating at least some of the PDX1-positive, NKX6.1-positive, insulin-positive endocrine cells into SC-β cells by a process of culturing the PDX1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, for a period of between 7 and 14 days to induce the in vitro maturation of at least some of the PDX1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into PDX1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor, v) a PKC activator, vi) a ROCK inhibitor, and vii) a growth factor from TGFβ superfamily, for a period of 2 days; d) differentiating at least some of the PDX1-positive pancreatic progenitor cells into PDX1-positive, NKX6.1-positive pancreatic progenitor cells by a process of contacting the PDX1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, for a period of 5 days; e) differentiating at least some of the PDX1-positive, NKX6.1-positive pancreatic progenitor cells into PDX1-positive, NKX6.1-positive, insulin-positive endocrine cells by a process of contacting the PDX1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, optionally vi) at least one growth factor from the epidermal growth factor (EGF) family, and optionally vii) a BMP signaling pathway inhibitor, for a period of between five and seven days; and f) differentiating at least some of the PDX1-positive, NKX6.1-positive, insulin-positive endocrine cells into SC-β cells by a process of culturing the PDX1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, for a period of between 7 and 14 days to induce the in vitro maturation of at least some of the PDX1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into PDX1-positive pancreatic progenitor cells by a process of contacting the primitive gut tube cells with i) retinoic acid signaling pathway activator, ii) at least one factor from the FGF family, iii) a SHH pathway inhibitor, iv) a PKC activator, and v) a ROCK inhibitor; d) differentiating at least some of the PDX1-positive pancreatic progenitor cells into PDX1-positive, NKX6.1-positive pancreatic progenitor cells by a process of contacting the PDX1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, for a period of 5 days; e) differentiating at least some of the PDX1-positive, NKX6.1-positive pancreatic progenitor cells into PDX1-positive, NKX6.1-positive, insulin-positive endocrine cells by a process of contacting the PDX1-positive, NKX6.1-positive pancreatic progenitor cells with i) a TGF-β signaling pathway inhibitor, ii) a TH signaling pathway activator, iii) at least one SHH pathway inhibitor, iv) a RA signaling pathway activator, v) a γ-secretase inhibitor, and optionally vi) at least one growth factor from the epidermal growth factor (EGF) family, for a period of between five and seven days; and f) differentiating at least some of the PDX1-positive, NKX6.1-positive, insulin-positive endocrine cells into SC-β cells by a process of culturing the PDX1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, for a period of between 7 and 14 days to induce the in vitro maturation of at least some of the PDX1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into PDX1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the PDX1-positive pancreatic progenitor cells into PDX1-positive, NKX6.1-positive pancreatic progenitor cells by a process of contacting the PDX1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, for a period of 5 or 6 days; e) differentiating at least some of the PDX1-positive, NKX6.1-positive pancreatic progenitor cells into PDX1-positive, NKX6.1-positive, insulin-positive endocrine cells by a process of contacting the PDX1-positive, NKX6.1-positive pancreatic progenitor cells with i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound (e.g., DZNep or KD5170), ix) a protein kinase inhibitor, and x) a ROCK inhibitor, for a period of between five and seven days; and f) differentiating at least some of the PDX1-positive, NKX6.1-positive, insulin-positive endocrine cells into SC-β cells by a process of culturing the PDX1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, for a period of between 7 and 14 days to induce the in vitro maturation of at least some of the PDX1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into PDX1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the PDX1-positive pancreatic progenitor cells into PDX1-positive, NKX6.1-positive pancreatic progenitor cells by a process of contacting the PDX1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, for a period of 5 or 6 days; e) differentiating at least some of the PDX1-positive, NKX6.1-positive pancreatic progenitor cells into PDX1-positive, NKX6.1-positive, insulin-positive endocrine cells by a process of contacting the PDX1-positive, NKX6.1-positive pancreatic progenitor cells with i) a γ-secretase inhibitor, ii) at least one bone morphogenetic protein (BMP) signaling pathway inhibitor, iii) a TGF-β signaling pathway inhibitor, iv) a thyroid hormone signaling pathway activator, v) an epigenetic modifying compound (e.g., DZNep or KD5170), vi) a protein kinase inhibitor, and vii) a ROCK inhibitor, for a period of between five and seven days, and within first three days of the period of between five and seven days, contacting the PDX1-positive, NKX6.1-positive pancreatic progenitor cells with a SHH pathway inhibitor, a RA signaling pathway, and at least one growth factor from the EGF family, which are removed from the PDX1-positive, NKX6.1-positive pancreatic progenitor cells thereafter; and f) differentiating at least some of the PDX1-positive, NKX6.1-positive, insulin-positive endocrine cells into SC-β cells by a process of culturing the PDX1-positive, NKX6.1-positive, insulin-positive endocrine cells in a medium (e.g., NS-GFs medium, MCDB medium supplemented with BSA, MCDB131 medium, or DMEM/F12 medium) without exogenous differentiation factors, for a period of between 7 and 14 days to induce the in vitro maturation of at least some of the PDX1-positive, NKX6.1-positive, insulin-positive endocrine cells into SC-β cells, wherein the SC-β cells exhibit a GSIS response in vitro and/or in vivo. In some cases, the GSIS response resembles the GSIS response of an endogenous mature β cells.

In some aspects, the disclosure provides a method of generating SC-β cells from pluripotent cells, the method comprising: a) differentiating pluripotent stem cells in a population into definitive endoderm cells by contacting the pluripotent stem cells with at least one factor from TGFβ superfamily and a WNT signaling pathway activator for a period of 3 days; b) differentiating at least some of the definitive endoderm cells into primitive gut tube cells by a process of contacting the definitive endoderm cells with at least one factor from the FGF family for a period of 3 days; c) differentiating at least some of the primitive gut tube cells into PDX1-positive pancreatic progenitor cells by a process of contacting the primitive gut tube cells with i) retinoic acid signaling pathway activator, ii) at least one factor from the FGF family, iii) a SHH pathway inhibitor, iv) a BMP signaling pathway inhibitor (e.g., DMH-1 or LDN193189), v) a PKC activator, and vi) a ROCK inhibitor; d) differentiating at least some of the PDX1-positive pancreatic progenitor cells into PDX1-positive, NKX6.1-positive pancreatic progenitor cells by a process of contacting the PDX1-positive pancreatic progenitor cells under conditions that promote cell clustering with i) at least one growth factor from the FGF family, ii) at least one SHH pathway inhibitor, and optionally iii) a RA signaling pathway activator, and optionally iv) ROCK inhibitor and v) at least one factor from TGFβ superfamily, for a period of 3 or 4 days, followed by contacting with i) at least one growth factor from the FGF family, ii) at least one SHH pathway inhibitor, and optionally iii) a RA signaling pathway activator, and optionally iv) ROCK inhibitor, v) at least one factor from TGFβ superfamily, and vi) a PKC activator, and optionally vii) a gamma secretase inhibitor, for 1 to 2 days; e) differentiating at least some of the PDX1-positive, NKX6.1-positive pancreatic progenitor cells into PDX1-positive, NKX6.1-positive, insulin-positive endocrine cells by a process of contacting the PDX1-positive, NKX6.1-positive pancreatic progenitor cells with i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound (e.g., DZNep or KD5170), ix) a protein kinase inhibitor, x) a ROCK inhibitor, and xi) a PKC activator, for 1 to 2 days, followed by contacting with i) a SHH pathway inhibitor, ii) a RA signaling pathway activator, iii) a γ-secretase inhibitor, iv) at least one growth factor from the epidermal growth factor (EGF) family, v) at least one bone morphogenetic protein (BMP) signaling pathway inhibitor, vi) a TGF-β signaling pathway inhibitor, vii) a thyroid hormone signaling pathway activator, viii) an epigenetic modifying compound (e.g., DZNep or KD5170), ix) a protein kinase inhibitor, and x) a ROCK inhibitor, for a period of between three and six days; and f) differentiating at least some of the PDX1-positive, NKX6.1-positive, insulin-positive endocrine cells into SC-β cells.

The medium used to culture the cells dissociated from the first cell cluster can be xeno-free. A xeno-free medium for culturing cells and/or cell clusters of originated from an animal can have no product from other animals. In some cases, a xeno-free medium for culturing human cells and/or cell clusters can have no products from any non-human animals. For example, a xeno-free medium for culturing human cells and/or cell clusters can comprise human platelet lysate (PLT) instead of fetal bovine serum (PBS). For example, a medium can comprise from about 1% to about 20%, from about 5% to about 15%, from about 8% to about 12%, from about 9 to about 11% serum. In some cases, medium can comprise about 10% of serum. In some cases, the medium can be free of small molecules and/or FBS. For example, a medium can comprise MCDB131 basal medium supplemented with 2% BSA. In some cases, the medium is serum-free. In some examples, a medium can comprise no exogenous small molecules or signaling pathway agonists or antagonists, such as, growth factor from fibroblast growth factor family (FGF, such as FGF2, FGF8B, FGF 10, or FGF21), Sonic Hedgehog Antagonist (such as Sant1, Sant2, Sant4, Sant4, Cur61414, forskolin, tomatidine, AY9944, triparanol, cyclopamine, or derivatives thereof), Retinoic Acid Signaling agonist (e.g., retinoic acid, CD1530, AM580, TTHPB, CD437, Ch55, BMS961, AC261066, AC55649, AM80, BMS753, tazarotene, adapalene, or CD2314), inhibitor of Rho-associated, coiled-coil containing protein kinase (ROCK) (e.g., Thiazovivin, Y-27632, Fasudil/HA1077, or 14-1152), activator of protein kinase C (PKC) (e.g., phorbol 12,13-dibutyrate (PDBU), TPB, phorbol 12-myristate 13-acetate, bryostatin 1, or derivatives thereof), antagonist of TGF β super family (e.g., Alk5 inhibitor II (CAS 446859-33-2), A83-01, SB431542, D4476, GW788388, LY364947, LY580276, SB505124, GW6604, SB-525334, SD-208, SB-505124, or derivatives thereof), inhibitor of Bone Morphogenetic Protein (BMP) type 1 receptor (e.g., LDN193189 or derivatives thereof), thyroid hormone signaling pathway activator (e.g., T3, GC-1 or derivatives thereof), gamma-secretase inhibitor (e.g., XXI, DAPT, or derivatives thereof), activator of TGF-β signaling pathway (e.g., WNT3a or Activin A) growth factor from epidermal growth factor (EGF) family (e.g., betacellulin or EGF), broad kinase (e.g., staurosporine or derivatives thereof), non-essential amino acids, vitamins or antioxidants (e.g., cyclopamine, vitamin D, vitamin C, vitamin A, or derivatives thereof), or other additions like N-acetyl cysteine, zinc sulfate, or heparin. In some cases, the reaggregation medium can comprise no exogenous extracellular matrix molecule. In some cases, the reaggregation medium does not comprise Matrigel™. In some cases, the reaggregation medium does not comprise other extracellular matrix molecules or materials, such as, collagen, gelatin, poly-L-lysine, poly-D-lysine, vitronectin, laminin, fibronectin, PLO laminin, fibrin, thrombin, and RetroNectin and mixtures thereof, for example, or lysed cell membrane preparations.

A person of ordinary skill in the art will appreciate that that the concentration of serum albumin supplemented into the medium may vary. For example, a medium (e.g., MCDB131) can comprise about 0.01%, 0.05%, 0.1%, 1%, about 2%, about 3%, about 4%, about 5%, about 10%, or about 15% BSA. In other cases, a medium can comprise about 0.01%, 0.05%, 0.1%, 1%, about 2%, about 3%, about 4%, about 5%, about 10%, or about 15% HSA. The medium used (e.g., MCDB131 medium) can contain components not found in traditional basal media, such as trace elements, putrescine, adenine, thymidine, and higher levels of some amino acids and vitamins. These additions can allow the medium to be supplemented with very low levels of serum or defined components. The medium can be free of proteins and/or growth factors, and may be supplemented with EGF, hydrocortisone, and/or glutamine. The medium can comprise one or more extracellular matrix molecules (e.g., extracellular proteins). Non-limiting exemplary extracellular matrix molecules used in the medium can include collagen, placental matrix, fibronectin, laminin, merosin, tenascin, heparin, heparin sulfate, chondroitin sulfate, dermatan sulfate, aggrecan, biglycan, thrombospondin, vitronectin, and decorin. In some cases, the medium comprises laminin, such as LN-332. In some cases, the medium comprises heparin.

The medium can be changed periodically in the culture, e.g., to provide optimal environment for the cells in the medium. When culturing the cells dissociated from the first cell cluster for re-aggregation, the medium can be changed at least or about every 4 hours, 12 hours, 24 hours, 48 hours, 3 days or 4 days. For example, the medium can be changed about every 48 hours.

In some cases, cells can be cultured under dynamic conditions (e.g., under conditions in which the cells are subject to constant movement or stirring while in the suspension culture). For dynamic culturing of cells, the cells can be cultured in a container (e.g., an non-adhesive container such as a spinner flask (e.g., of 200 ml to 3000 ml, for example 250 ml; of 100 ml; or in 125 ml Erlenmeyer), which can be connected to a control unit and thus present a controlled culturing system. In some cases, cells can be cultured under non-dynamic conditions (e.g., a static culture) while preserving their proliferative capacity. For non-dynamic culturing of cells, the cells can be cultured in an adherent culture vessel. An adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used). The substrate for cell adhesion includes collagen, gelatin, poly-L-lysine, poly-D-lysine, vitronectin, laminin, fibronectin, PLO laminin, fibrin, thrombin, and RetroNectin and mixtures thereof, for example, Matrigel™, and lysed cell membrane preparations.

Medium in a dynamic cell culture vessel (e.g., a spinner flask) can be stirred (e.g., by a stirrer). The spinning speed can correlate with the size of the re-aggregated second cell cluster. The spinning speed can be controlled so that the size of the second cell cluster can be similar to an endogenous pancreatic islet. In some cases, the spinning speed is controlled so that the size of the second cell cluster can be from about 75 μm to about 250 μm. The spinning speed of a dynamic cell culture vessel (e.g., a spinner flask) can be about 20 rounds per minute (rpm) to about 100 rpm, e.g., from about 30 rpm to about 90 rpm, from about 40 rpm to about 60 rpm, from about 45 rpm to about 50 rpm. In some cases, the spinning speed can be about 50 rpm.

Stage 6 cells as provided herein may or may not be subject to the dissociation and reaggregation process as described herein. In some cases, the cell cluster comprising the insulin-positive endocrine cells can be reaggregated. The reaggregation of the cell cluster can enrich the insulin-positive endocrine cells. In some cases, the insulin-positive endocrine cells in the cell cluster can be further matured into pancreatic β cells. For example, after reaggregation, the second cell cluster can exhibit in vitro GSIS, resembling native pancreatic islet. For example, after reaggregation, the second cell cluster can comprise non-native pancreatic β cell that exhibits in vitro GSIS. In some embodiments, the reaggregation process can be performed according to the disclosure of PCT application PCT/US2018/043179, which is incorporated herein by reference in its entirety.

Stage 6 cells obtained according to methods provided herein can have high recovery yield after cryopreservation and reaggregation procedures. In some cases, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a higher recovery yield after cryopreservation post stage 5, as compared to a corresponding cell population without such treatment. In some cases, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a higher recovery yield after cryopreservation post stage 5, as compared to a corresponding cell population without treatment of a BMP signaling pathway inhibitor (e.g., DMH-1 or LDN) and a growth factor from TGF-β superfamily (e.g., Activin A) at stage 3. In some cases, stage 6 cells that are obtained in a differentiation process that involves treatment of a BMP signaling pathway inhibitor (e.g., DMH-1 or LDN) and a growth factor from TGF-β superfamily (e.g., Activin A) at stage 3 and treatment of an epigenetic modifying compound (e.g., histone methyltransferase inhibitor, e.g., EZH2 inhibitor, e.g., DZNep) at stage 5 can have a recovery yield after cryopreservation post stage 5 that is at least about 35%, 37.5%, 40%, 42.5%, 45%, 47.5%, 48%, 49%, or 50%. The recovery yield can be calculated as a percentage of cells that survive and form reaggregated cell clusters after cryopreservation, thawing and recovery, and reaggregation procedures, as compared to the cells before the cryopreservation.

In some embodiments, the present disclosure relates to cryopreservation of the non-native pancreatic β cells or precursors thereof obtained using the methods provided herein. In some embodiments, the cell population comprising non-native pancreatic β cells can be stored via cryopreservation. For instances, the cell population comprising non-native β cells, e.g., Stage 6 cells in some cases, can be dissociated into cell suspension, e.g., single cell suspension, and the cell suspension can be cryopreserved, e.g., frozen in a cryopreservation solution. The dissociation of the cells can be conducted by any of the technique provided herein, for example, by enzymatic treatment. The cells can be frozen at a temperature of at highest −20° C., at highest −30° C., at highest −40° C., at highest −50° C., at highest −60° C., at highest −70° C., at highest −80° C., at highest −90° C., at highest −100° C., at highest −110° C., at highest −120° C., at highest −130° C., at highest −140° C., at highest −150° C., at highest −160° C., at highest −170° C., at highest −180° C., at highest −190° C., or at highest −200° C. In some cases, the cells are frozen at a temperature of about −80° C. In some cases, the cells are frozen at a temperature of about −195° C. Any cooling methods can be used for providing the low temperature needed for cryopreservation, such as, but not limited to, electric freezer, solid carbon dioxide, and liquid nitrogen. In some cases, any cryopreservation solution available to one skilled in the art can be used for incubating the cells for storage at low temperature, including both custom made and commercial solutions. For example, a solution containing a cryoprotectant can be used. The cryoprotectant can be an agent that is configured to protect the cell from freezing damage. For instance, a cryoprotectant can be a substance that can lower the glass transition temperature of the cryopreservation solution. Exemplary cryoprotectants that can be used include DMSO (dimethyl sulfoxide), glycols (e.g., ethylene glycol, propylene glycol and glycerol), dextran (e.g., dextran-40), and trehalose. Additional agents can be added in to the cryopreservation solution for other effects. In some cases, commercially available cryopreservation solutions can be used in the method provided herein, for instance, FrostaLife™, pZerve™, Prime-XV®, Gibco Synth-a-Freeze Cryopreservation Medium, STEM-CELL-BANKER®, CryoStor® Freezing Media, HypoThermosol® FRS Preservation Media, and CryoDefend® Stem Cells Media.

During the differentiation process, the cells can be subject to irradiation treatment as provided herein. In some cases, the cell population at Stage 6, e.g., the cell population or cell cluster that has cells being differentiated from insulin-positive endocrine cells into pancreatic β cells, is irradiated for a period of time. In some cases, the cell population at Stage 6 after reaggregation following the recovery from cryopreservation is irradiated for a period of time. In some cases, the cryopreserved cells (e.g., the cells that are cryopreserved at the end of Stage 5) are irradiated for a certain period of time prior to thawing and recovery for subsequent differentiation process.

In some embodiments, the stage 6 cells comprise NKX6.1-positive, insulin-positive cells. In some embodiments, the stage 6 cells comprise NKX6.1-positive, insulin-negative cells. In some embodiments, the stage 6 cells comprise C-peptide positive cells. In some embodiments, Stage 6 cells or cells that have characteristics of stage 6 cells are incubated in NS-GFs medium, MCDB131 medium, DMEM medium, or CMRL medium. In some embodiments, the stage 6 cells or cells that have characteristics of stage 6 cells are contacted with any one or more of a vitamin or anti-oxidant (e.g., vitamin C), an albumin protein (e.g., a human serum albumin protein), a TGF-beta pathway inhibitor (e.g., an ALK5 inhibitor II), a bone morphogenic protein (BMP) type 1 receptor inhibitor (e.g., LDN193189), a Rho-associated coiled-coil containing protein kinase (ROCK) inhibitor (e.g., thiazovivin), a histone methyltransferase inhibitor (e.g., DZNEP), and a protein kinase inhibitor (e.g., staurosporine). In some embodiments, the stage 6 cells are contacted with a PKC activator (see, e.g., WO2019217487, which is incorporated by reference herein in its entirety).

Differentiation Factors

Aspects of the disclosure relate to contacting progenitor cells (e.g., stem cells, e.g., iPS cells, definitive endoderm cells, primitive gut tube cells, PDX1-positive pancreatic progenitor cells, NKX6.1-positive pancreatic progenitor cells, insulin-positive endocrine cells) with 0 cell differentiation factors, for example, to induce the maturation of the insulin-positive endocrine cells or differentiation of other progenitor cells into SC-β cells (e.g., mature pancreatic β cells). In some embodiments, the differentiation factor can induce the differentiation of pluripotent cells (e.g., iPSCs or hESCs) into definitive endoderm cells, e.g., in accordance with a method described herein. In some embodiments, the differentiation factor can induce the differentiation of definitive endoderm cells into primitive gut tube cells, e.g., in accordance with a method described herein. In some embodiments, the differentiation factor can induce the differentiation of primitive gut tube cells into PDX1-positive pancreatic progenitor cells, e.g., in accordance with a method described herein. In some embodiments, the differentiation factor can induce the differentiation of PDX1-positive pancreatic progenitor cells into NKX6-1-positive pancreatic progenitor cells, e.g., in accordance with a method described herein. In some embodiments, the differentiation factor can induce the differentiation of NKX6-1-positive pancreatic progenitor cells into insulin-positive endocrine cells, e.g., in accordance with a method described herein. In some embodiments, the differentiation factor can induce the maturation of insulin-positive endocrine cells into SC-β cells, e.g., in accordance with a method described herein.

At least one differentiation factor described herein can be used alone, or in combination with other differentiation actors, to generate SC-β cells according to the methods as disclosed herein. In some embodiments, at least two, at least three, at least four, at least five, at least six, at least seven, at least eight, at least nine, or at least ten differentiation factors described herein are used in the methods of generating SC-β cells.

Transforming Growth Factor-β (TGF-β) Superfamily

Aspects of the disclosure relate to the use of growth factors from the transforming growth factor-β (TGF-β) superfamily as differentiation factors. The "TGF-β superfamily" means proteins having structural and functional characteristics of known TGFβ family members. The TGFβ family of proteins can include the TGFβ series of proteins, the Inhibins (including Inhibin A and Inhibin B), the Activins (including Activin A, Activin B, and Activin AB), MIS (Müllerian inhibiting substance), BMP (bone morphogenetic proteins), dpp (decapentaplegic), Vg-1, MNSF (monoclonal nonspecific suppressor factor), and others. Activity of this family of proteins can be based on specific binding to certain receptors on various cell types. Members of this family can share regions of sequence identity, particularly at the C-terminus, that correlate to their function. The TGFβ family can include more than one hundred distinct proteins, all sharing at least one region of amino acid sequence identity. Members of the family that can be used in the method disclosed herein can include, but are not limited to, the following proteins, as identified by their GenBank accession numbers: P07995, P18331, P08476, Q04998, P03970, P43032, P55102, P27092, P42917, P09529, P27093, P04088, Q04999, P17491, P55104, Q9WUK5, P55103, O88959, O08717, P58166, O61643, P35621, P09534, P48970, Q9NR23, P25703, P30884, P12643, P49001, P21274, O46564, O19006, P22004, P20722, Q04906, Q07104, P30886, P18075, P23359, P22003, P34821, P49003, Q90751, P21275, Q06826, P30885, P34820, Q29607, P12644, Q90752, O46576, P27539, P48969, Q26974, P07713, P91706, P91699, P27091, O42222, Q24735, P20863, O18828, P55106, Q9PTQ2, O14793, O08689, O42221, O18830, O18831, O18836, O35312, O42220, P43026, P43027, P43029, O95390, Q9R229, O93449, Q9Z1W4, Q9BDW8, P43028, Q7Z4P5, P50414, P17246, P54831, P04202, P01137, P09533, P18341, O19011, Q9Z1Y6, P07200, Q9Z217, O95393, P55105, P30371, Q9MZE2, Q07258, Q96S42, P97737, AAA97415.1, NP-776788.1, NP-058824.1, EAL24001.1, 1 S4Y, NP-001009856.1, NP-1-032406.1, NP-999193.1, XP-519063.1, AAG17260.1, CAA40806.1, NP-1-001009458.1, AAQ55808.1, AAK40341.1, AAP33019.1, AAK21265.1, AAC59738.1, CAI46003.1, B40905, AAQ55811.1, AAK40342.1, XP-540364.1, P55102, AAQ55810.1, NP-990727.1, CAA51163.1, AAD50448.1, JC4862, PN0504, BAB17600.1, AAH56742.1, BAB17596.1, CAG06183.1, CAG05339.1, BAB17601.1, CAB43091.1, A36192, AAA49162.1, AAT42200.1, NP-789822.1, AAA59451.1, AAA59169.1, XP-541000.1, NP-990537.1, NP-1-002184.1, AAC14187.1, AAP83319.1, AAA59170.1, BAB16973.1, AAM66766.1, WFPGBB, 1201278C, AAH30029.1, CAA49326.1, XP-344131.1, AA-148845.1, XP-1-148966.3, 148235, B41398, AAH77857.1, AAB26863.1, 1706327A, BAA83804.1, NP-571143.1, CAG00858.1, BAB17599.1, BAB17602.1, AAB61468.1, PN0505, PN0506, CAB43092.1, BAB17598.1, BAA22570.1, BAB16972.1, BAC81672.1, BAA12694.1, BAA08494.1, B36192, C36192, BAB16971.1, NP-034695.1, AAA49160.1, CAA62347.1, AAA49161.1, AAD30132.1, CAA58290.1, NP-005529.1, XP-522443.1, AAM27448.1, XP-538247.1, AAD30133. I, AAC36741.1, AAH10404.1, NP-032408.1, AAN03682.1, XP-509161.1, AAC32311.1, NP-651942.2, AAL51005.1, AAC39083.1, AAH85547.1, NP-571023.1, CAF94113.1, EAL29247.1, AAW30007.1, AAH90232.1, A29619, NP-001007905.1, AAH73508.1, AADO2201.1, NP-999793.1, NP-990542.1, AAF19841.1, AAC97488.1, AAC60038.1, NP 989197.1, NP-571434.1, EAL41229.1, AAT07302.1, CAI19472.1, NP-031582.1, AAA40548.1, XP-535880.1, NP-1-037239.1, AAT72007.1, XP-418956.1, CAA41634.1, BAC30864.1, CAA38850.1, CAB81657.2, CAA45018.1, CAA45019.1, BAC28247.1, NP-031581.1, NP-990479.1, NP-999820.1, AAB27335.1, S45355, CAB82007.1, XP-534351.1, NP-058874.1, NP-031579.1, 1REW, AAB96785.1, AAB46367.1, CAA05033.1, BAA89012.1, IES7, AAP20870.1, BAC24087.1, AAG09784.1, BAC06352.1, AAQ89234.1, AAM27000.1, AAH30959.1, CAGO1491.1, NP-571435.1, 1REU, AAC60286.1, BAA24406.1, A36193, AAH55959.1, AAH54647.1, AAH90689.1, CAG09422.1, BAD16743.1, NP-032134.1, XP-532179.1, AAB24876.1, AAH57702.1, AAA82616.1, CAA40222.1, CAB90273.2, XP-342592.1, XP-534896.1, XP-534462.1, 1LXI, XP-417496.1, AAF34179.1, AAL73188.1, CAF96266.1, AAB34226.1, AAB33846.1, AAT12415.1, AA033819.1, AAT72008.1, AAD38402.1, BAB68396.1, CAA45021.1, AAB27337.1, AAP69917.1, AATI2416.1, NP-571396.1, CAA53513.1, AA033820.1, AAA48568.1, BAC02605.1, BAC02604.1, BAC02603.1, BAC02602.1, BAC02601.1, BAC02599.1, BAC02598.1, BAC02597.1, BAC02595.1, BAC02593.1, BAC02592.1, BAC02590.1, AAD28039.1, AAP74560.1, AAB94786.1, NP-001483.2, XP-528195.1, NP-571417.1, NP-001001557. I, AAH43222.1, AAM33143.1, CAG10381.1, BAA31132.1, EAL39680.1, EAA12482.2, P34820, AAP88972.1, AAP74559.1, CAI16418.1, AAD30538.1, XP-345502.1, NP-1-038554.1, CAG04089.1, CAD60936.2, NP-031584.1, B55452, AAC60285.1, BAA06410.1, AAH52846.1, NP-031580.1, NP-1-036959.1, CAA45836.1, CAA45020.1, Q29607, AAB27336.1, XP-547817.1, AAT12414.1, AAM54049.1, AAH78901.1, AA025745.1, NP-570912.1, XP-392194.1, AAD20829.1, AAC97113.1, AAC61694.1, AAH60340.1, AAR97906.1, BAA32227.1, BAB68395.1, BAC02895.1, AAWS 1451.1, AAF82188.1, XP-544189.1, NP-990568.1, BAC80211.1, AAW82620.1, AAF99597.1, NP-571062.1, CAC44179.1, AAB97467.1, AAT99303.1, AAD28038.1, AAH52168.1, NP-001004122.1, CAA72733.1, NP-032133.2, XP-394252.1, XP-224733.2, JH0801, AAP97721.1, NP-989669.1, S43296, P43029, A55452, AAH32495.1, XP-542974.1, NP-032135.1, AAK30842.1, AAK27794.1, BAC30847.1, EAA12064.2, AAP97720.1, XP-525704.1, AAT07301.1, BAD07014.1, CAF94356.1, AAR27581.1, AAG13400.1, AAC60127.1, CAF92055.1, XP-540103.1, AA020895.1, CAF97447.1, AAS01764.1, BAD08319.1, CAA10268.1, NP-998140.1, AAR03824.1, AAS48405.1, AAS48403.1, AAK53545.1, AAK84666.1, XP-395420.1, AAK56941.1, AAC47555.1, AAR88255.1, EAL33036.1, AAW47740.1, AAW29442.1, NP-722813.1, AARO8901.1, AAO 15420.2, CAC59700.1, AAL26886.1, AAK71708.1, AAK71707.1, CAC51427.2, AAK67984.1, AAK67983.1, AAK28706.1, P07713, P91706, P91699, CAG02450.1, AAC47552.1, NP-005802.1, XP-343149.1, AW34055.1, XP-538221.1, AAR27580.1, XP-125935.3, AAF21633.1, AAF21630.1, AAD05267.1, Q9Z1 W4, NP-1-031585.2, NP-571094.1, CAD43439.1, CAF99217.1, CAB63584.1, NP-722840.1, CAE46407.1, XP-1-417667.1, BAC53989.1, BAB19659.1, AAM46922.1, AAA81169.1, AAK28707.1, AAL05943.1, AAB17573.1, CAH25443.1, CAG10269.1, BAD16731.1, EAA00276.2, AAT07320.1, AAT07300.1, AAN15037.1, CAH25442.1, AAK08152.2, 2009388A, AAR12161.1, CAGO1961.1, CAB63656.1, CAD67714.1, CAF94162.1, NP-477340.1, EAL24792.1, NP-1-001009428.1, AAB86686.1, AAT40572.1, AAT40571.1, AAT40569.1, NP-033886.1, AAB49985.1, AAG39266.1, Q26974, AAC77461.1, AAC47262.1, BAC05509.1, NP-055297.1, XP-546146.1, XP-525772.1, NP-060525.2, AAH33585.1, AAH69080.1, CAG12751.1, AAH74757.2, NP-034964.1, NP-038639.1, 042221, AAF02773.1, NP-062024.1, AAR18244.1, AAR14343.1, XP-228285.2, AAT40573.1, AAT94456.1, AAL35278.1, AAL35277.1, AAL17640.1, AAC08035.1, AAB86692.1, CAB40844.1, BAC38637.1, BAB16046.1, AAN63522.1, NP-571041.1, AAB04986.2, AAC26791.1, AAB95254.1, BAA11835.1, AAR18246.1, XP-538528.1, BAA31853.1, AAK18000.1, XP-1-420540.1, AAL35276.1, AAQ98602.1, CAE71944.1, AAW50585.1, AAV63982.1, AAW29941.1, AAN87890.1, AAT40568.1, CAD57730.1, AAB81508.1, AAS00534.1, AAC59736.1, BAB79498.1, AAA97392.1, AAP85526.1, NP-999600.2, NP-878293.1, BAC82629.1, CAC60268.1, CAG04919.1, AAN10123.1, CAA07707.1 AAK20912.1, AAR88254.1, CAC34629.1, AAL35275.1, AAD46997. I, AAN03842.1, NP-571951.2, CAC50881.1, AAL99367.1, AAL49502.1, AAB71839.1, AAB65415.1, NP-624359.1, NP-990153.1, AAF78069.1, AAK49790.1, NP-919367.2, NP-001192.1, XP-544948.1, AAQ18013.1, AAV38739.1, NP-851298.1, CAA67685.1, AAT67171.1, AAT37502.1, AAD27804.1, AAN76665.1, BAC11909.1, XP-1-421648.1, CAB63704.1, NP-037306.1, A55706, AAF02780.1, CAG09623.1, NP-067589.1, NP-035707.1, AAV30547.1, AAP49817.1, BAC77407.1, AAL87199.1, CAG07172.1, B36193, CAA33024.1, NP-1-001009400.1, AAP36538.1, XP-512687.1, XP-510080.1, AAH05513.1, 1KTZ, AAH14690.1, AAA31526.1.

The growth factor from the TGF-β superfamily in the methods and compositions provided herein can be naturally obtained or recombinant. In some embodiments, the growth factor from the TGF-β superfamily comprises Activin A. The term "Activin A" can include fragments and derivatives of Activin A. The sequence of an exemplary Activin A is disclosed as SEQ ID NO: 1 in U.S. Pub. No. 2009/0155218 (the '218 publication). Other non-limiting examples of Activin A are provided in SEQ ID NO: 2-16 of the '218 publication, and non-limiting examples of nucleic acids encoding Activin A are provided in SEQ ID NO:33-34 of the '218 publication. In some embodiments, the growth factor from the TGF-β superfamily can comprise a polypeptide having an amino acid sequence at least 30%, at least 40%, at least 50%, at least 60%, at least 70%, at least 80%, at least 90%, at least 95%, or at least 99%, or greater identical to SEQ ID NO: 1 of the '218 publication.

In some embodiments, the growth factor from the TGF-β superfamily comprises growth differentiation factor 8 (GDF8). The term "GDF8" can include fragments and derivatives of GDF8. The sequences of GDF8 polypeptides are available to the skilled artisan. In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF8 polypeptide sequence (GenBank Accession EAX10880).

In some embodiments, the growth factor from the TGF-β superfamily comprises a growth factor that is closely related to GDF8, e.g., growth differentiation factor 11 (GDF11). In some embodiments, the growth factor from the TGF-β superfamily comprises a polypeptide having an amino acid sequence at least 30%, at least 40%, at least 50%, at least 60%, at least 70%, at least 80%, at least 90%, at least 95%, or at least 99%, or greater identical to the human GDF11 polypeptide sequence (GenBank Accession AAF21630).

In some embodiments, the growth factor from the TGF-β superfamily can be replaced with an agent mimics the at least one growth factor from the TGF-β superfamily. Exemplary agents that mimic the at least one growth factor from the TGF-β superfamily, include, without limitation, IDE1 and IDE2.

Bone Morphogenetic Protein (BMP) Signaling Pathway Inhibitors

Aspects of the disclosure relate to the use of BMP signaling pathway inhibitors as β cell differentiation factors. The BMP signaling family is a diverse subset of the TGF-β superfamily (Sebald et al. Biol. Chem. 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. Cell Signal 16:291-299, 2004). Soluble BMP antagonists such as noggin, chordin, gremlin, and follistatin limit BMP signaling by ligand sequestration.

In some embodiments, the BMP signaling pathway inhibitor in the methods and composition provided herein comprises DMH-1, or a derivative, analogue, or variant thereof. In some embodiments, the BMP signaling pathway inhibitor in the methods and composition provided herein comprises the following compound or a derivative, analogue, or variant of the following compound:

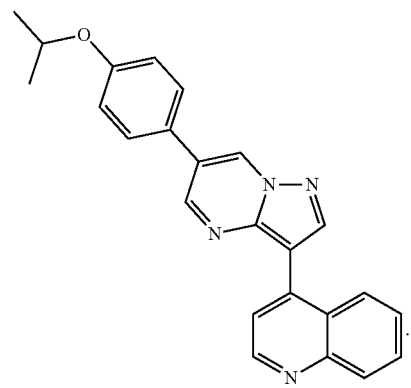 [SMILES: CC(C)Oc1ccc(-c2cnc3c(-c4ccnc5ccccc45)cnn3c2)cc1]

In some embodiments, the BMP signaling pathway inhibitor in the methods and composition provided herein comprises LDN193189 (also known as LDN193189, 1062368-24-4, LDN-193189, DM 3189, DM-3189, IUPAC Name: 4-[6-(4-piperazin-1-ylphenyl)pyrazolo[1,5-a]pyrimidin-3-yl]quinolone). In some embodiments, the BMP signaling pathway inhibitor in the methods and composition provided herein comprises the following compound or a derivative, analogue, or variant of the following compound:

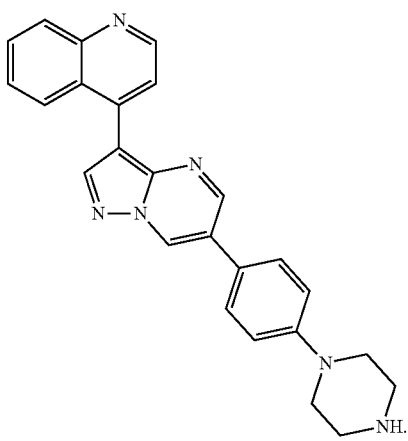 [SMILES: c1ccc2c(-c3cnn4cc(-c5ccc(N6CCNCC6)cc5)cnc34)ccnc2c1]

In some cases, DMH-1 can be more selective as compared to LDN193189. In some embodiments of the present disclosure, DMH-1 can be particularly useful for the methods provided herein. In some embodiments, the methods and compositions provided herein exclude use of LDN193189. In some embodiments, the methods and compositions provided herein exclude use of LDN193189, or a derivative, analogue, or variant thereof for generating PDX1-positive pancreatic progenitor cells from primitive gut tube cells. In some embodiments, the methods and compositions provided herein relate to use of DMH-1, or a derivative, analogue, or variant thereof for generating PDX1-positive pancreatic progenitor cells from primitive gut tube cells.

In some embodiments, the BMP signaling pathway inhibitor in the methods and composition provided herein comprise an analog or derivative of LDN193189, e.g., a salt, hydrate, solvent, ester, or prodrug of LDN193189. In some embodiments, a derivative (e.g., salt) of LDN193189 comprises LDN193189 hydrochloride.

In some embodiments, the BMP signaling pathway inhibitor in the methods and composition provided herein comprises a compound of Formula I from U.S. Patent Publication No. 2011/0053930.

TGF-β Signaling Pathway Inhibitors

Aspects of the disclosure relate to the use of TGF-β signaling pathway inhibitors as β cell differentiation factors.

In some embodiments, the TGF-β signaling pathway comprises TGF-β receptor type I kinase (TGF-β RI) signaling. In some embodiments, the TGF-β signaling pathway inhibitor comprises ALK5 inhibitor II (CAS 446859-33-2, an ATP-competitive inhibitor of TGF-B RI kinase, also known as RepSox, IUPAC Name: 2-[5-(6-methylpyridin-2-yl)-1H-pyrazol-4-yl]-1,5-naphthyridine. In some embodiments, the TGF-β signaling pathway inhibitor is an analog or derivative of ALK5 inhibitor II.

In some embodiments, the analog or derivative of ALK5 inhibitor II (also named "ALK5i") is a compound of Formula I as described in U.S. Patent Publication No. 2012/0021519, incorporated by reference herein in its entirety.

In some embodiments, the TGF-β signaling pathway inhibitor in the methods and compositions provided herein is a TGF-β receptor inhibitor described in U.S. Patent Publication No. 2010/0267731. In some embodiments, the TGF-β signaling pathway inhibitor in the methods and compositions provided herein comprises an ALK5 inhibitor described in U.S. Patent Publication Nos. 2009/0186076 and 2007/0142376. In some embodiments, the TGF-β signaling pathway inhibitor in the methods and compositions provided herein is A 83-01. In some embodiments, the TGF-β signaling pathway inhibitor in the methods and compositions provided herein is not A 83-01. In some embodiments, the compositions and methods described herein exclude A 83-01. In some embodiments, the TGF-β signaling pathway inhibitor in the methods and compositions provided herein is SB 431542. In some embodiments, the TGF-β signaling pathway inhibitor is not SB 431542. In some embodiments, the compositions and methods described herein exclude SB 431542. In some embodiments, the TGF-β signaling pathway inhibitor in the methods and compositions provided herein is D 4476. In some embodiments, the TGF-β signaling pathway inhibitor is not D 4476. In some embodiments, the compositions and methods described herein exclude D 4476. In some embodiments, the TGF-β signaling pathway inhibitor in the methods and compositions provided herein is GW 788388. In some embodiments, the TGF-β signaling pathway inhibitor is not GW 788388. In some embodiments, the compositions and methods described herein exclude GW 788388. In some embodiments, the TGF-β signaling pathway inhibitor in the methods and compositions provided herein is LY 364947. In some embodiments, the TGF-β signaling pathway inhibitor is not LY 364947. In some embodiments, the compositions and methods described herein exclude LY 364947. In some embodiments, the TGF-β signaling pathway inhibitor in the methods and compositions provided herein is LY 580276. In some embodiments, the TGF-β signaling pathway inhibitor is not LY 580276. In some embodiments, the compositions and methods described herein exclude LY 580276. In some embodiments, the TGF-β signaling pathway inhibitor in the methods and compositions provided herein is SB 525334. In some embodiments, the TGF-β signaling pathway inhibitor is not SB 525334. In some embodiments, the compositions and methods described herein exclude SB 525334. In some embodiments, the TGF-β signaling pathway inhibitor in the methods and compositions provided herein is SB 505124. In some embodiments, the TGF-β signaling pathway inhibitor is not SB 505124. In some embodiments, the compositions and methods described herein exclude SB 505124. In some embodiments, the TGF-β signaling pathway inhibitor in the methods and compositions provided herein is SD 208. In some embodiments, the TGF-β signaling pathway inhibitor is not SD 208. In some embodiments, the compositions and methods described herein exclude SD 208. In some embodiments, the TGF-β signaling pathway inhibitor in the methods and compositions provided herein is GW 6604. In some embodiments, the TGF-β signaling pathway inhibitor is not GW 6604. In some embodiments, the compositions and methods described herein exclude GW 6604. In some embodiments, the TGF-β signaling pathway inhibitor in the methods and compositions provided herein is GW 788388. In some embodiments, the TGF-β signaling pathway inhibitor in the methods and compositions provided herein is not GW 788388. In some embodiments, the compositions and methods described herein exclude GW 788388.

From the collection of compounds described above, the following can be obtained from various sources: LY-364947, SB-525334, SD-208, and SB-505124 available from Sigma, P.O. Box 14508, St. Louis, Mo., 63178-9916; 616452 and 616453 available from Calbiochem (EMD Chemicals, Inc.), 480 S. Democrat Road, Gibbstown, N.J., 08027; GW788388 and GW6604 available from GlaxoSmithKline, 980 Great West Road, Brentford, Middlesex, TW8 9GS, United Kingdom; LY580276 available from Lilly Research, Indianapolis, Ind. 46285; and SM16 available from Biogen Idec, P.O. Box 14627, 5000 Davis Drive, Research Triangle Park, N.C., 27709-4627.

WNT Signaling Pathway

Aspects of the disclosure relate to the use of activators of the WNT signaling pathway as β cell differentiation factors.

In some embodiments, the WNT signaling pathway activator in the methods and compositions provided herein comprises CHIR99021. In some embodiments, the WNT signaling pathway activator in the methods and compositions provided herein comprises a derivative of CHIR99021, e.g., a salt of CHIR99021, e.g., trihydrochloride, a hydrochloride salt of CHIR99021. In some embodiments, the WNT signaling pathway activator in the methods and compositions provided herein comprises Wnt3a recombinant protein. In some embodiments, the WNT signaling pathway activator in the methods and compositions provided herein comprises a glycogen synthase kinase 3 (GSK3) inhibitor. Exemplary GSK3 inhibitors include, without limitation, 3F8, A 1070722, AR-A 014418, BIO, BIO-acetoxime, FRATide, 10Z-Hymenialdisine, Indirubin-3'oxime, kenpaullone, L803, L803-mts, lithium carbonate, NSC 693868, SB 216763, SB 415286, TC-G 24, TCS 2002, TCS 21311, TWS 119, and analogs or derivatives of any of these. In certain embodiments, the methods, compositions, and kits disclosed herein exclude a WNT signaling pathway activator.

Fibroblast Growth Factor (FGF) Family

Aspects of the disclosure relate to the use of growth factors from the FGF family as β cell differentiation factors.

In some embodiments, the growth factor from the FGF family in the methods and compositions provided herein comprises keratinocyte growth factor (KGF). The polypeptide sequences of KGF are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human KGF polypeptide sequence (GenBank Accession AAB21431).

In some embodiments, the growth factor from the FGF family in the methods and composition provided herein comprises FGF2. The polypeptide sequences of FGF2 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF2 polypeptide sequence (GenBank Accession NP_001997).

In some embodiments, the at least one growth factor from the FGF family in the methods and composition provided herein comprises FGF8B. The polypeptide sequences of FGF8B are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF8B polypeptide sequence (GenBank Accession AAB40954).

In some embodiments, the at least one growth factor from the FGF family in the methods and composition provided herein comprises FGF10. The polypeptide sequences of FGF10 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF10 polypeptide sequence (GenBank Accession CAG46489).

In some embodiments, the at least one growth factor from the FGF family in the methods and composition provided herein comprises FGF21. The polypeptide sequences of FGF21 are available to the skilled artisan. In some embodiments, the growth factor from the FGF family comprises a polypeptide having an amino acid sequence at least 30%, at least 40%, at least 50%, at least 60%, at least 70%, at least 80%, at least 90%, at least 95%, or at least 99%, or greater identical to the human FGF21 polypeptide sequence (GenBank Accession AAQ89444.1).

Sonic Hedgehog (SHH) Signaling Pathway

Aspects of the disclosure relate to the use of SHH signaling pathway inhibitors as β cell differentiation factors.

In some embodiments, the SHH signaling pathway inhibitor in the methods and composition provided herein comprises Sant1. In some embodiments, the SHH signaling pathway inhibitor in the methods and composition provided herein comprises SANT2. In some embodiments, the SHH signaling pathway inhibitor in the methods and composition provided herein comprises SANT3. In some embodiments, the SHH signaling pathway inhibitor in the methods and composition provided herein comprises SANT4. In some embodiments, the SHH signaling pathway inhibitor comprises Cur61414. In some embodiments, the SHH signaling pathway inhibitor in the methods and composition provided herein comprises forskolin. In some embodiments, the SHH signaling pathway inhibitor in the methods and composition provided herein comprises tomatidine. In some embodiments, the SHH signaling pathway inhibitor in the methods and composition provided herein comprises AY9944. In some embodiments, the SHH signaling pathway inhibitor in the methods and composition provided herein comprises triparanol. In some embodiments, the SHH signaling pathway inhibitor in the methods and composition provided herein comprises compound A or compound B (as disclosed in U.S. Pub. No. 2004/0060568). In some embodiments, the SHH signaling pathway inhibitor in the methods and composition provided herein comprises a steroidal alkaloid that antagonizes hedgehog signaling (e.g., cyclopamine or a derivative thereof) as disclosed in U.S. Pub. No. 2006/0276391. In certain embodiments, the methods, compositions, and kits disclosed herein exclude a SHH signaling pathway inhibitor.

Rho Kinase (ROCK) Signaling Pathway

Aspects of the disclosure relate to the use of ROCK signaling pathway inhibitors (ROCK inhibitors) as β cell differentiation factors.

In some embodiments, the ROCK inhibitor in the methods and composition provided herein comprises Y-27632 or Thiazovivin. In some embodiments, the ROCK inhibitor in the methods and composition provided herein comprises Thiazovivin. In some embodiments, the ROCK inhibitor in the methods and composition provided herein comprises Y-27632. In some cases, the ROCK inhibitor in the methods and composition provided herein comprises the following compound or a derivative thereof:

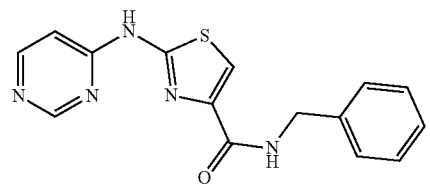 [SMILES: O=C(NCc1ccccc1)c1csc(Nc2ccncn2)n1]

In some cases, the ROCK inhibitor in the methods and composition provided herein comprises the following compound or a derivative thereof:

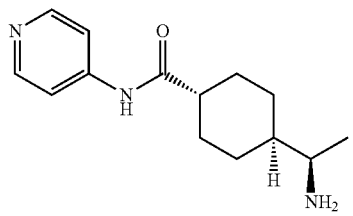

Non-limiting examples of ROCK inhibitor that can be used in the methods and compositions provided herein include Thiazovivin, Y-27632, Fasudil/HA1077, H-1152, Ripasudil, Y39983, Wf-536, SLx-2119, Azabenzimidazole-aminofurazans, DE-104, Olefins, Isoquinolines, Indazoles, and pyridinealkene derivatives, ROKα inhibitor, XD-4000, HMN-1152, 4-(1-aminoalkyl)-N-(4-pyridyl)cyclohexanecarboxamides, Rhostatin, BA-210, BA-207, BA-215, BA-285, BA-1037, Ki-23095, VAS-012, and quinazoline.

Retinoic Acid Signaling Pathway

Aspects of the disclosure relate to the use of modulators of retinoic acid signaling as β cell differentiation factors.

In some embodiments, the modulator of retinoic acid signaling in the methods and composition provided herein comprises an activator of retinoic acid signaling. In some embodiments, the RA signaling pathway activator in the methods and composition provided herein comprises retinoic acid. In some embodiments, the RA signaling pathway activator in the methods and composition provided herein comprises a retinoic acid receptor agonist. Exemplary retinoic acid receptor agonists in the methods and composition provided herein include, without limitation, CD 1530, AM 580, TTNPB, CD 437, Ch 55, BMS 961, AC 261066, AC 55649, AM 80, BMS 753, tazarotene, adapalene, and CD 2314.

In some embodiments, the modulator of retinoic acid signaling in the methods and composition provided herein comprises an inhibitor of retinoic acid signaling. In some embodiments, the retinoic acid signaling pathway inhibitor comprises DEAB (IUPAC Name: 2-[2-(diethylamino) ethoxy]-3-prop-2-enylbenzaldehyde). In some embodiments, the retinoic acid signaling pathway inhibitor comprises an analog or derivative of DEAB.

In some embodiments, the retinoic acid signaling pathway inhibitor in the methods and composition provided herein comprises a retinoic acid receptor antagonist. In some embodiments, the retinoic acid receptor antagonist in the methods and composition provided herein comprises (E)-4-[2-(5,6-dihydro-5,5-dimethyl-8-phenyl-2-naphthalenyl) ethenyl]benzoic acid, (E)-4-[[(5,6-dihydro-5,5-dimethyl-8-phenylethynyl)-2-naphthalenyl]ethenyl]benzoic acid, (E)-4-[2-[5,6-dihydro-5,5-dimethyl-8-(2-naphthalenyl)-2-naphthalenyl]ethenyl]-benzoic acid, and (E)-4-[2-[5,6-dihydro-5,5-dimethyl-8-(4-methoxyphenyl)-2-naphthalenyl]ethenyl]benzoic acid. In some embodiments, the retinoic acid receptor antagonist comprises BMS 195614 (CAS #253310-42-8), ER 50891 (CAS #187400-85-7), BMS 493 (CAS #170355-78-9), CD 2665 (CAS #170355-78-9), LE 135 (CAS #155877-83-1), BMS 453 (CAS #166977-43-1), or MM 11253 (CAS #345952-44-5).

In certain embodiments, the methods, compositions, and kits disclosed herein exclude a modulator of retinoic acid signaling. In certain embodiments, the methods, compositions, and kits disclosed herein exclude a retinoic acid signaling pathway activator. In certain embodiments, the methods, compositions, and kits disclosed herein exclude a retinoic acid signaling pathway inhibitor.

Protein Kinase C

Aspects of the disclosure relate to the use of protein kinase C activators as β cell differentiation factors. Protein kinase C is one of the largest families of protein kinase enzymes and is composed of a variety of isoforms. Conventional isoforms include a, βI, βII, γ; novel isoforms include δ, ε, η, Θ; and atypical isoforms include ξ, and ι/λ. PKC enzymes are primarily cytosolic but translocate to the membrane when activated. In the cytoplasm, PKC is phosphorylated by other kinases or autophosphorylated. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all. PKC activators that bind to the DAG site include, but are not limited to, bryostatin, picologues, phorbol esters, aplysiatoxin, and gnidimacrin. PKC activators that bind to the PS site include, but are not limited to, polyunsaturated fatty acids and their derivatives. It is contemplated that any protein kinase C activator that is capable, either alone or in combination with one or more other β cell differentiation factors, of inducing the differentiation of at least one insulin-producing, endocrine cell or precursor thereof into a SC-β cell can be used in the methods, compositions, and kits described herein.

In some embodiments, any of the PKC activators disclosed herein is a PKC activator capable of binding to a DAG binding site on a PKC. In some embodiments, the PKC activator is capable of binding to a C1 domain of a PKC. In some embodiments, the PKC activator is a benzolactam-derivative. In some embodiments, the benzolactam-derivative is ((2S,5S)-(E,E)-8-(5-(4-(Trifluoromethyl)phenyl)-2,4-pentadienoylamino)benzolactam), which may be referred to herein as TPPB or TPB. In some embodiments, contacting a population of cells with a benzolactam-derivative PKC activator (e.g., TPPB) increases cell yield as compared to a population of cells not treated with the benzolactam-derivative PKC activator. In some embodiments, the PKC activator is a phorbol ester. In some embodiments, the phorbol ester is Phorbol 12,13-dibutyrate, which may be referred to herein as PDBU or PdbU. In some embodiments, contacting a population of cells with a benzolactam-derivative PKC activator (e.g., TPPB) increases cell yield as compared to a population of cells treated with a phorbol ester PKC activator (e.g., PdbU). In some embodiments, the PKC activator in the methods and composition provided herein comprises PdbU. In some embodiments, the PKC activator in the methods and composition provided herein comprises TPB. In some embodiments, the PKC activator in the methods and composition provided herein comprises cyclopropanated polyunsaturated fatty acids, cyclopropanated monounsaturated fatty acids, cyclopropanated polyunsaturated fatty alcohols, cyclopropanated monounsaturated fatty alcohols, cyclopropanated polyunsaturated fatty acid esters, cyclopropanated monounsaturated fatty acid esters, cyclopropanated polyunsaturated fatty acid sulfates, cyclopropanated monounsaturated fatty acid sulfates, cyclopropanated polyunsaturated fatty acid phosphates, cyclopropanated monounsaturated fatty acid phosphates, macrocyclic lactones, DAG derivatives, isoprenoids, octylindolactam V, gnidimacrin, iripallidal, ingenol, napthalenesulfonamides, diacylglycerol kinase inhibitors, fibroblast growth factor 18 (FGF-18), insulin growth factor, hormones, and growth factor activators, as described in WIPO Pub. No. WO/2013/071282. In some embodiments, the bryostain comprises bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In certain embodiments, the methods, compositions, and kits disclosed herein exclude a protein kinase C activator.

γ-Secretase Inhibitors

Aspects of the disclosure relate to the use of γ-secretase inhibitors as β cell differentiation factors.

In some embodiments, the γ-secretase inhibitor in the methods and composition provided herein comprises XXI. In some embodiments, the γ-secretase inhibitor in the methods and composition provided herein comprises DAPT. Additional exemplary γ-secretase inhibitors in the methods and composition provided herein include, without limitation, the γ-secretase inhibitors described in U.S. Pat. Nos. 7,049,296, 8,481,499, 8,501,813, and WIPO Pub. No. WO/2013/052700. In certain embodiments, the methods, compositions, and kits disclosed herein exclude a γ-secretase inhibitor.

Thyroid Hormone Signaling Pathway Activators

Aspects of the disclosure relate to the use of thyroid hormone signaling pathway activators as β cell differentiation factors.

In some embodiments, the thyroid hormone signaling pathway activator in the methods and composition provided herein comprises triiodothyronine (T3). In some embodiments, the thyroid hormone signaling pathway activator in the methods and composition provided herein comprises GC-1. In some embodiments, the thyroid hormone signaling pathway activator in the methods and composition provided herein comprises an analog or derivative of T3 or GC-1. Exemplary analogs of T3 in the methods and composition provided herein include, but are not limited to, selective and non-selective thyromimetics, TRβ selective agonist-GC-1, GC-24,4-Hydroxy-PCB 106, MB07811, MB07344,3,5-diiodothyropropionic acid (DITPA); the selective TR-β agonist GC-1; 3-Iodothyronamine (T(1)AM) and 3,3',5-triiodothyroacetic acid (Triac) (bioactive metabolites of the hormone thyroxine (T(4)); KB-2115 and KB-141; thyronamines; SKF L-94901; DIBIT; 3'-AC-T2; tetraiodothyroacetic acid (Tetrac) and triiodothyroacetic acid (Triac) (via oxidative deamination and decarboxylation of thyroxine [T4] and triiodothyronine [T3] alanine chain), 3,3',5'-triiodothyronine (rT3) (via T4 and T3 deiodination), 3,3'-diiodothyronine (3,3'-T2) and 3,5-diiodothyronine (T2) (via T4, T3, and rT3 deiodination), and 3-iodothyronamine (T1AM) and thyronamine (T0AM) (via T4 and T3 deiodination and amino acid decarboxylation), as well as for TH structural analogs, such as 3,5,3'-triiodothyropropionic acid (Triprop), 3,5-dibromo-3-pyridazinone-1-thyronine (L-940901), N-[3,5-dimethyl-4-(4'-hydroxy-3'-isopropylphenoxy)-phenyl]-oxamic acid (CGS 23425), 3,5-dimethyl-4-[(4'-hydroxy-3'-isopropylbenzyl)-phenoxy]acetic acid (GC-1), 3,5-dichloro-4-[(4-hydroxy-3-isopropylphenoxy)phenyl]acetic acid (KB-141), and 3,5-diiodothyropropionic acid (DITPA).

In some embodiments, the thyroid hormone signaling pathway activator in the methods and composition provided herein comprises a prodrug or prohormone of T3, such as T4 thyroid hormone (e.g., thyroxine or L-3,5,3',5'-tetraiodothyronine).

In some embodiments, the thyroid hormone signaling pathway activator in the methods and composition provided herein is an iodothyronine composition described in U.S. Pat. No. 7,163,918.

Epidermal Growth Factor (EGF) Family

Aspects of the disclosure relate to the use of growth factors from the EGF family as β cell differentiation factors.

In some embodiments, the at least one growth factor from the EGF family in the methods and composition provided herein comprises betacellulin. In some embodiments, at least one growth factor from the EGF family in the methods and composition provided herein comprises EGF. Epidermal growth factor (EGF) is a 53 amino acid cytokine which is proteolytically cleaved from a large integral membrane protein precursor. In some embodiments, the growth factor from the EGF family in the methods and composition provided herein comprises a variant EGF polypeptide, for example an isolated epidermal growth factor polypeptide having at least 90% amino acid identity to the human wild-type EGF polypeptide sequence, as disclosed in U.S. Pat. No. 7,084,246. In some embodiments, the growth factor from the EGF family in the methods and composition provided herein comprises an engineered EGF mutant that binds to and agonizes the EGF receptor, as is disclosed in U.S. Pat. No. 8,247,531. In some embodiments, the at least one growth factor from the EGF family in the methods and composition provided herein is replaced with an agent that activates a signaling pathway in the EGF family. In some embodiments, the growth factor from the EGF family in the methods and composition provided herein comprises a compound that mimics EGF. In certain embodiments, the methods, compositions, and kits disclosed herein exclude a growth factor from the EGF family.

Epigenetic Modifying Compounds

Aspects of the disclosure relate to the use of epigenetic modifying compound as β cell differentiation factors.

The term "epigenetic modifying compound" can refer to a chemical compound that can make epigenetic changes genes, i.e., change gene expression(s) without changing DNA sequences. Epigenetic changes can help determine whether genes are turned on or off and can influence the production of proteins in certain cells, e.g., beta-cells. Epigenetic modifications, such as DNA methylation and histone modification, can alter DNA accessibility and chromatin structure, thereby regulating patterns of gene expression. These processes can be crucial to normal development and differentiation of distinct cell lineages in the adult organism. They can be modified by exogenous influences, and, as such, can contribute to or be the result of environmental alterations of phenotype or pathophenotype. Importantly, epigenetic modification can have a crucial role in the regulation of pluripotency genes, which become inactivated during differentiation. Non-limiting exemplary epigenetic modifying compound include a DNA methylation inhibitor, a histone acetyltransferase inhibitor, a histone deacetylase inhibitor, a histone methyltransferase inhibitor, a bromodomain inhibitor, or any combination thereof.

In an embodiment, the histone methyltransferase inhibitor is an inhibitor of enhancer of zeste homolog 2 (EZH2). EZH2 is a histone-lysine N-methyltransferase enzyme. Non-limiting examples of an EZH2 inhibitor that can be used in the methods provided herein include 3-deazaneplanocin A (DZNep), EPZ6438, EPZ005687 (an S-adenosylmethionine (SAM) competitive inhibitor), EI1, GSK126, and UNC1999. DZNep can inhibit the hydrolysis of S-adenosyl-L-homocysteine (SAH), which is a product-based inhibitor of all protein methyltransferases, leading to increased cellular concentrations of SAH which in turn inhibits EZH2. DZNep may not be specific to EZH2 and can also inhibit other DNA methyltransferases. GSK126 is a SAM-competitive EZH2 inhibitor that has 150-fold selectivity over EZH1. UNC1999 is an analogue of GSK126, and it is less selective than its counterpart GSK126.

In an embodiment, the histone methyltransferase inhibitor is DZNep. In an embodiment, the HDAC inhibitor is a class I HDAC inhibitor, a class II HDAC inhibitor, or a combination thereof. In an embodiment, the HDAC inhibitor is KD5170 (mercaptoketone-based HDAC inhibitor), MC1568 (class IIa HDAC inhibitor), TMP195 (class IIa HDAC inhibitor), or any combination thereof. In some embodiments, HDAC inhibitor is vorinostat, romidepsin (Istodax), chidamide, panobinostat (farydak), belinostat (PXD101), panobinostat (LBH589), valproic acid, mocetinostat (MGCD0103), abexinostat (PCI-24781), entinostat (MS-275), SB939, resminostat (4SC-201), givinostat (ITF2357), quisinostat (JNJ-26481585), HBI-8000, (a benzamide HDI), kevetrin, CUDC-101, AR-42, CHR-2845, CHR-3996, 4SC-202, CG200745, ACY-1215, ME-344, sulforaphane, or any variant thereof.

Protein Kinase Inhibitors

Aspects of the disclosure relate to the use of protein kinase inhibitors as β cell differentiation factors.

In some embodiments, the protein kinase inhibitor in the methods and composition provided herein comprises staurosporine. In some embodiments, the protein kinase inhibitor in the methods and composition provided herein comprises an analog of staurosporine. Exemplary analogs of staurosporine in the methods and composition provided herein include, without limitation, Ro-31-8220, a bisindolylmaleimide (Bis) compound, 10'-{5"-[(methoxycarbonyl)amino]-2"-methyl}-phenylaminocarbonylstaurosporine, a staralog (see, e.g., Lopez et al., "Staurosporine-derived inhibitors broaden the scope of analog-sensitive kinase technology", *J. Am. Chem. Soc.* 2013; 135(48):18153-18159), and, cgp41251.

In some embodiments, the protein kinase inhibitor in the methods and composition provided herein is an inhibitor of PKCβ. In some embodiments, the protein kinase inhibitor in the methods and composition provided herein is an inhibitor of PKCβ with the following structure or a derivative, analogue or variant of the compound as follows:

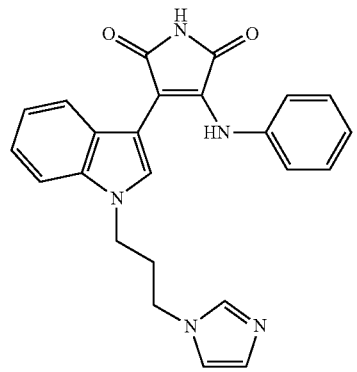 [SMILES: O=C1NC(=O)C(c2cn(CCCn3ccnc3)c3ccccc23)=C1Nc1ccccc1]

In some embodiments, the inhibitor of PKCβ is a GSK-2 compound with the following structure or a derivative, analogue or variant of the compound as follows:

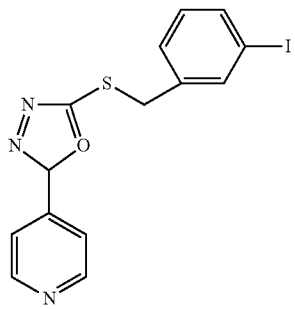

In some embodiments, the inhibitor of PKC in the methods and composition provided herein is a bisindolylmaleimide. Exemplary bisindolylmaleimides include, without limitation, bisindolylmaleimide I, bisindolylmaleimide II, bisindolylmaleimide III, hydrochloride, or a derivative, analogue or variant thereof.

In some embodiments, the PKC inhibitor in the methods and composition provided herein is a pseudohypericin, or a derivative, analogue, or variant thereof. In some embodiments, the PKC inhibitor in the methods and composition provided herein is indorublin-3-monoxime, 5-Iodo or a derivative, analogue or variant thereof. In certain embodiments, the methods, compositions, and kits disclosed herein exclude a protein kinase inhibitor.

Pharmaceutical Compositions

The present disclosure relates to a therapeutic composition containing cells produced by any of the foregoing methods or containing any of the foregoing cell populations. The therapeutic compositions can further comprise a physiologically compatible solution including, for example, artificial cerebrospinal fluid or phosphate-buffered saline. The therapeutic composition can be used to treat, prevent, or stabilize diabetes. For example, somatic cells or stem cells can be obtained from an individual in need of treatment or from a healthy individual and reprogrammed to stem cell derived beta cells by the method of the present disclosure. In one embodiment of the present disclosure the stem cell derived beta cells are sorted and enriched and introduced into the individual to treat the condition. In another embodiment the stem cells are cultured under conditions suitable for differentiation into beta cells prior to introduction into the individual, and can be used to replace or assist the normal function of diseased or damaged tissue. The great advantage of the present disclosure is that it provides an essentially limitless supply of patient specific human beta cells or compatible stem cell derived beta cells from healthy individuals with the same HLA type suitable for transplantation. The use of autologous and/or compatible cells in cell therapy offers a major advantage over the use of non-autologous cells, which are likely to be subject to immunological rejection. In contrast, autologous cells are unlikely to elicit significant immunological responses.

In some cases, the present disclosure provides pharmaceutical compositions that can utilize non-native pancreatic β cell (beta cells) populations and cell components and products in various methods for treatment of a disease (e.g., diabetes). Certain cases encompass pharmaceutical compositions comprising live cells (e.g., non-native pancreatic β cells alone or admixed with other cell types). Other cases encompass pharmaceutical compositions comprising non-native pancreatic β cell components (e.g., cell lysates, soluble cell fractions, conditioned medium, ECM, or components of any of the foregoing) or products (e.g., trophic and other biological factors produced by non-native pancreatic β cells or through genetic modification, conditioned medium from non-native pancreatic β cell culture). In either case, the pharmaceutical composition may further comprise other active agents, such as anti-inflammatory agents, exogenous small molecule agonists, exogenous small molecule antagonists, anti-apoptotic agents, antioxidants, and/or growth factors known to a person having skill in the art.

In some embodiments, any of the cells disclosed herein comprise a genomic disruption in at least one gene sequence, wherein said disruption reduces or eliminates expression of a protein encoded by said gene sequence. In some embodiments, said cells comprise a genomic disruption in at least one gene sequence, wherein said disruption reduces or eliminates expression of a protein encoded by said gene sequence. In some embodiments, said cells comprise a genomic disruption in at least one gene sequence, wherein said disruption reduces or eliminates expression of a protein encoded by said gene sequence. In some embodiments, any of the cells disclosed herein (e.g., any of the SC-derived beta cells or cells in any of the clusters disclosed herein) comprise a genomic disruption in at least one gene sequence, wherein said disruption reduces or eliminates expression of a protein encoded by said gene sequence. In some embodiments, said at least one gene sequence encodes an MHC-Class I gene. In some embodiments, said MHC-Class I gene encodes beta-2 microglobulin (B2M), HLA-A, HLA-B, or HLA-C. In some embodiments, said at least one gene sequence encodes CIITA. In some embodiments, said cells comprise a genomic disruption in a natural killer cell activating ligand gene. In some embodiments, said natural killer cell activating ligand gene encodes intercellular adhesion molecule 1 (ICAM1), CD58, CD155, carcinoembryonic antigen-related cell adhesion molecule 1 (CEACAM1), cell adhesion molecule 1 (CADM1), MHC-Class I polypeptide-related sequence A (MICA), or MHC-Class I polypeptide-related sequence B (MICB). In some embodiments, the genomic disruption is induced by use of a gene editing system, e.g., CRISPR Cas technology.

Pharmaceutical compositions of the present disclosure can comprise non-native pancreatic β cell, or components or products thereof, formulated with a pharmaceutically acceptable carrier (e.g. a medium or an excipient). The term pharmaceutically acceptable carrier (or medium), which may be used interchangeably with the term biologically compatible carrier or medium, can refer to reagents, cells, compounds, materials, compositions, and/or dosage forms that are not only compatible with the cells and other agents to be administered therapeutically, but also are suitable for use in contact with the tissues of human beings and animals without excessive toxicity, irritation, allergic response, or other complication. Suitable pharmaceutically acceptable carriers can include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical compositions comprising cellular components or products, but not live cells, can be formulated as liquids. Pharmaceutical compositions comprising living non-native pancreatic β cells can be formulated as liquids, semisolids (e.g., gels, gel capsules, or liposomes) or solids (e.g., matrices, scaffolds and the like).

As used here, the term "pharmaceutically acceptable" can refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" can refer to a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

The phrase "therapeutically-effective amount" as used herein in respect to a population of cells means that amount of relevant cells in a population of cells, e.g., SC-β cells or mature pancreatic β cells, or composition comprising SC-β cells of the present disclosure which is effective for producing some desired therapeutic effect in at least a sub-population of cells in an animal at a reasonable benefit/risk ratio applicable to any medical treatment. For example, an amount of a population of SC-β cells administered to a subject that is sufficient to produce a statistically significant, measurable change in at least one symptom of Type 1, Type 1.5 or Type 2 diabetes, such as glycosylated hemoglobin level, fasting blood glucose level, hypoinsulinemia, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In some instances, pharmaceutical compositions of the stem cell derived beta cells are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, a composition of the present disclosure can comprise the stem cell derived beta cells, in an amount that is effective to treat or prevent e.g., diabetes. A pharmaceutical composition can comprise the stem cell derived beta cells as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Pharmaceutical compositions can comprise auxiliary components as would be familiar to a person having skill in the art. For example, they can contain antioxidants in ranges that vary depending on the kind of antioxidant used. Reasonable ranges for commonly used antioxidants are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. Other representative compounds include mercaptopropionyl glycine, N-acetyl cysteine, β-mercaptoethylamine, glutathione and similar species, although other anti-oxidant agents suitable for renal administration, e.g. ascorbic acid and its salts or sulfite or sodium metabisulfite may also be employed.

A buffering agent can be used to maintain the pH of formulations in the range of about 4.0 to about 8.0; soas to minimize irritation in the target tissue. For direct intraperitoneal injection, formulations should be at pH 7.2 to 7.5, preferably at pH 7.35-7.45. The compositions may also include tonicity agents suitable for administration to the kidney. Among those suitable is sodium chloride to make formulations approximately isotonic with blood.

In certain cases, pharmaceutical compositions are formulated with viscosity enhancing agents. Exemplary agents are hydroxyethylcellulose, hydroxypropylcellulose, methylcellulose, and polyvinylpyrrolidone. The pharmaceutical compositions may have cosolvents added if needed. Suitable cosolvents may include glycerin, polyethylene glycol (PEG), polysorbate, propylene glycol, and polyvinyl alcohol. Preservatives may also be included, e.g., benzalkonium chloride, benzethonium chloride, chlorobutanol, phenylmercuric acetate or nitrate, thimerosal, or methyl or propylparabens.

Pharmaceutical compositions comprising cells, cell components or cell products may be delivered to the kidney of a patient in one or more of several methods of delivery known in the art. In some cases, the compositions are delivered to the kidney (e.g., on the renal capsule and/or underneath the renal capsule). In another embodiment, the compositions may be delivered to various locations within the kidney via periodic intraperitoneal or intrarenal injection. Alternatively, the compositions may be applied in other dosage forms known to those skilled in the art, such as pre-formed or in situ-formed gels or liposomes.

Pharmaceutical compositions comprising live cells in a semi-solid or solid carrier are may be formulated for surgical implantation on or beneath the renal capsule. It should be appreciated that liquid compositions also may be administered by surgical procedures. In particular cases, semi-solid or solid pharmaceutical compositions may comprise semipermeable gels, lattices, cellular scaffolds and the like, which may be non-biodegradable or biodegradable. For example, in certain cases, it may be desirable or appropriate to sequester the exogenous cells from their surroundings, yet enable the cells to secrete and deliver biological molecules (e.g., insulin) to surrounding cells or the blood stream. In these cases, cells may be formulated as autonomous implants comprising living non-native pancreatic β cells or cell population comprising non-native pancreatic β cell surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression.

In other cases, various degradable gels and networks can be used for the pharmaceutical compositions of the present disclosure. For example, degradable materials particularly suitable for sustained release formulations include biocompatible polymers, such as poly(lactic acid), poly (lactic-co-glycolic acid), methylcellulose, hyaluronic acid, collagen, and the like.

In other cases, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established.

Examples of scaffold or matrix (sometimes referred to collectively as "framework") material that may be used in the present disclosure include nonwoven mats, porous foams, or self-assembling peptides. Nonwoven mats, for example, may be formed using fibers comprising a synthetic absorbable copolymer of glycolic and lactic acids (PGA/PLA), foams, and/or poly(epsilon-caprolactone)/poly(glycolic acid) (PCL/PGA) copolymer.

In another embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures. In many of the abovementioned cases, the framework may be molded into a useful shape. Furthermore, it will be appreciated that non-native pancreatic β cells may be cultured on pre-formed, non-degradable surgical or implantable devices.

The matrix, scaffold or device may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In one aspect, the present disclosure provided devices comprising a cell cluster comprising at least one pancreatic β cell. A device provided herein can be configured to produce and release insulin when implanted into a subject. A device can comprise a cell cluster comprising at least one pancreatic β cell, e.g., a non-native pancreatic β cell. A cell cluster in the device can exhibit in vitro GSIS. A device can further comprise a semipermeable membrane. The semipermeable membrane can be configured to retain the cell cluster in the device and permit passage of insulin secreted by the cell cluster. In some cases of the device, the cell cluster can be encapsulated by the semipermeable membrane. The encapsulation can be performed by any technique available to one skilled in the art. The semipermeable membrane can also be made of any suitable material as one skilled in the art would appreciate and verify. For example, the semipermeable membrane can be made of polysaccharide or polycation. In some cases, the semipermeable membrane can be made of poly(lactide) (PLA), poly(glycolic acid) (PGA), poly(lactide-co-glycolide) (PLGA), and other polyhydroxyacids, poly(caprolactone), polycarbonates, polyamides, polyanhydrides, polyphosphazene, polyamino acids, poly-ortho esters, polyacetals, polycyanoacrylates, biodegradable polyurethanes, albumin, collagen, fibrin, polyamino acids, prolamines, alginate, agarose, agarose with gelatin, dextran, polyacrylates, ethylene-vinyl acetate polymers and other acyl-substituted cellulose acetates and derivatives thereof, polyurethanes, polystyrenes, polyvinyl chloride, polyvinyl fluoride, poly(vinyl imidazole), chlorosulphonated polyolefins, polyethylene oxide, or any combinations thereof. In some cases, the semipermeable membrane comprises alginate. In some cases, the cell cluster is encapsulated in a microcapsule that comprises an alginate core surrounded by the semipermeable membrane. In some cases, the alginate core is modified, for example, to produce a scaffold comprising an alginate core having covalently conjugated oligopeptides with an RGD sequence (arginine, glycine, aspartic acid). In some cases, the alginate core is modified, for example, to produce a covalently reinforced microcapsule having a chemoenzymatically engineered alginate of enhanced stability. In some cases, the alginate core is modified, for example, to produce membrane-mimetic films assembled by in-situ polymerization of acrylate functionalized phospholipids. In some cases, microcapsules are composed of enzymatically modified alginates using epimerases, In some cases, microcapsules comprise covalent links between adjacent layers of the microcapsule membrane. In some embodiment, the microcapsule comprises a subsieve-size capsule comprising alginate coupled with phenol moieties. In some cases, the microcapsule comprises a scaffold comprising alginate-agarose. In some cases, the SC-β cell is modified with PEG before being encapsulated within alginate. In some cases, the isolated populations of cells, e.g., SC-β cells are encapsulated in photoreactive liposomes and alginate. It should be appreciated that the alginate employed in the microcapsules can be replaced with other suitable biomaterials, including, without limitation, polyethylene glycol (PEG), chitosan, polyester hollow fibers, collagen, hyaluronic acid, dextran with ROD, BHD and polyethylene glycol-diacrylate (PEGDA), poly(MPC-co-n-butyl methacrylate-co-4-vinylphenyl boronic acid) (PMBV) and poly (vinyl alcohol) (PVA), agarose, agarose with gelatin, and multilayer cases of these. In some cases, the device provided herein comprise extracorporeal segment, e.g., part of the device can be outside a subject's body when the device is implanted in the subject. The extracorporeal segment can comprise any functional component of the device, with or without the cells or cell cluster provided herein.

Methods of Treatment

Further provided herein are methods for treating or preventing a disease in a subject. A composition comprising the cell clusters or cells provided herein or generated according to the methods provided herein can be administered into a subject to restore a degree of pancreatic function in the subject. For example, the cell clusters resembling endogenous pancreatic islets, or the cells resembling endogenous pancreatic α, β and/or δ cells (e.g., non-native pancreatic α, β and/or δ cells) or the precursors thereof can be transplanted to a subject to treat diabetes. Most typically, a composition to be administered into a subject comprises cells that are fully differentiated, or cells that are nearly fully differentiated. However, as further differentiation of cells can be achieved in vivo, the present disclosure is not limited in this respect. For example, in some embodiments, a composition to be encapsulated in a device and/or administered into a subject comprises cells that are not fully differentiated (e.g., a composition comprising PDX1-positive, NKX6.1-negative pancreatic progenitor cells, and PDX1-positive, NKX6.1-positive pancreatic progenitor cells).

The methods can comprise transplanting the cell cluster or the cell disclosed in the application to a subject, e.g., a subject in need thereof. The term "transplanting" can refer to the placement of cells or cell clusters, any portion of the cells or cell clusters thereof, or any compositions comprising cells, cell clusters or any portion thereof, into a subject, by a method or route which results in at least partial localization of the introduced cells or cell clusters at a desired site. The cells or cell clusters can be implanted directly to the pancreas, or alternatively be administered by any appropriate route which results in delivery to a desired location in the subject where at least a portion of the implanted cells or cell remain viable. The period of viability of the cells or cell clusters after administration to a subject can be as short as a few hours, e.g. twenty-four hours, to a few days, to as long as several years. In some instances, the cells or cell clusters, or any portion of the cells or cell clusters thereof, can also be transadministered at a non-pancreatic location, such as in the liver or subcutaneously, for example, in a capsule (e.g., microcapsule) to maintain the implanted cells or cell clusters at the implant location and avoid migration.

As used herein, the term "treating" and "treatment" can refer to administering to a subject an effective amount of a composition (e.g., cell clusters or a portion thereof) so that the subject as a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, stabilized (e.g., not worsening) state of disease, delay or slowing of disease progression, amelioration or palliation of the disease state, and remission (e.g., partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In preferred embodiments, the compositions are administered by intravenous infusion or injection.

By "treatment," "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Delaying the onset of diabetes in a subject refers to delay of onset of at least one symptom of diabetes, e.g., hyperglycemia, hypoinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

In some aspects, the disclosure relates to a method comprising implanting in a subject a device comprising a cell or cell cluster provided herein (e.g., insulin producing cells), wherein the device releases insulin in an amount sufficient for a reduction of blood glucose levels in the subject. In some embodiments, the insulin producing cells are glucose responsive insulin producing cells.

In some embodiments, the reduction of blood glucose levels in the subject, as induced by the transplantation of the cell or cell cluster, or the device provided herein, results in an amount of glucose which is lower than the diabetes threshold. In some embodiments, the subject is a mammalian subject. In some embodiments, the mammalian subject is human. In some embodiments, the amount of glucose is reduced to lower than the diabetes threshold in 1, 2, 3, 4, 5, 6, 7, 8, 9, or 10 days after the implanting.

As described in detail above, the pharmaceutical compositions of the present disclosure can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 35 3,270,960.

A subject that can be treated by the methods herein can be a human or a non-human animal. In some cases, a subject can be a mammal. Examples of a subject include but are not limited to primates, e.g., a monkey, a chimpanzee, a bamboo, or a human. In some cases, a subject is a human. A subject can be non-primate animals, including, but not limited to, a dog, a cat, a horse, a cow, a pig, a sheep, a goat, a rabbit, and the like. In some cases, a subject receiving the treatment is a subject in need thereof, e.g., a human in need thereof.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used as subjects that represent animal models of Type 1 diabetes, Type 2 Diabetes Mellitus, or pre-diabetic conditions. In addition, the methods described herein can be used to treat domesticated animals and/or pets. A subject can be male or female. A subject can be one who has been previously diagnosed with or identified as suffering from or having Diabetes (e.g., Type 1 or Type 2), one or more complications related to Diabetes, or a pre-diabetic condition, and optionally, but need not have already undergone treatment for the Diabetes, the one or more complications related to Diabetes, or the pre-diabetic condition. A subject can also be one who is not suffering from Diabetes or a pre-diabetic condition. A subject can also be one who has been diagnosed with or identified as suffering from Diabetes, one or more complications related to Diabetes, or a pre-diabetic condition, but who show improvements in known Diabetes risk factors as a result of receiving one or more treatments for Diabetes, one or more complications related to Diabetes, or the pre-diabetic condition. Alternatively, a subject can also be one who has not been previously diagnosed as having Diabetes, one or more complications related to Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to Diabetes or a pre-diabetic condition as defined herein, or alternatively, a subject can be one who has not been previously diagnosed with or identified as having one or more complications related to Diabetes or a pre-diabetic condition.

The methods can comprise transplanting the cell cluster to a subject using any means in the art. For example the methods can comprise transplanting the cell cluster via the intraperitoneal space, renal subcapsule, renal capsule, omentum, subcutaneous space, or via pancreatic bed infusion. For example, transplanting can be subcapsular transplanting, intramuscular transplanting, or intraportal transplanting, e.g., intraportal infusion. Immunoprotective encapsulation can be implemented to provide immunoprotection to the cell clusters. In some cases, the methods of treatment provided herein can comprise administer immune response modulator for modulating or reducing transplant rejection response or other immune response against the implant (e.g., the cells or the device). Examples of immune response modulator that can be used in the methods can include purine synthesis inhibitors like Azathioprine and Mycophenolic acid, pyrimidine synthesis inhibitors like Leflunomide and Teriflunomide, antifolate like Methotrexate, Tacrolimus, Ciclosporin, Pimecrolimus, Abetimus, Gusperimus, Lenalidomide, Pomalidomide, Thalidomide, PDE4 inhibitor, Apremilast, Anakinra, Sirolimus, Everolimus, Ridaforolimus, Temsirolimus, Umirolimus, Zotarolimus, Anti-thymocyte globulin antibodies, Anti-lymphocyte globulin antibodies, CTLA-4, fragment thereof, and fusion proteins thereof like Abatacept and Belatacept, TNF inhibitor like Etanercept and Pegsunercept, Aflibercept, Alefacept, Rilonacept, antibodies against complement component 5 like Eculizumab, anti-TNF antibodies like Adalimumab, Afelimomab, Certolizumab pegol, Golimumab, Infliximab, and Nerelimomab, antibodies against Interleukin 5 like Mepolizumab, anti-Ig E antibodies like Omalizumab, anti-Interferon antibodies like Faralimomab, anti-IL-6 antibodies like Elsilimomab, antibodies against IL-12 and IL-23 like Lebrikizumab and Ustekinumab, anti-IL-17A antibodies like Secukinumab, anti-CD3 antibodies like Muromonab-CD3, Otelixizumab, Teplizumab, and Visilizumab, anti-CD4 antibodies like Clenoliximab, Keliximab, and Zanolimumab, anti-CD11a antibodies like Efalizumab, anti-CD18 antibodies like Erlizumab, anti-CD20 antibodies like Obinutuzumab, Rituximab, Ocrelizumab and Pascolizumab, anti-CD23 antibodies like Gomiliximab and Lumiliximab, anti-CD40 antibodies like Teneliximab and Toralizumab, antibodies against CD62L/L-selectin like Aselizumab, anti-CD80 antibodies like Galiximab, anti-CD147/Basigin antibodies like Gavilimomab, anti-CD154 antibodies like Ruplizumab, anti-BLyS antibodies like Belimumab and Blisibimod, anti-CTLA-4 antibodies like Ipilimumab and Tremelimumab, anti-CAT antibodies like Bertilimumab, Lerdelimumab, and Metelimumab, anti-Integrin antibodies like Natalizumab, antibodies against Interleukin-6 receptor like Tocilizumab, anti-LFA-1 antibodies like Odulimomab, antibodies against IL-2 receptor/CD25 like Basiliximab, Daclizumab, and Inolimomab, antibodies against T-lymphocyte (Zolimomab aritox) like Atorolimumab, Cedelizumab, Fontolizumab, Maslimomab, Morolimumab, Pexelizumab, Reslizumab, Roveli-zumab, Siplizumab, Talizumab, Telimomab aritox, Vapaliximab, and Vepalimomab.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

EXAMPLES

These examples are provided for illustrative purposes only and not to limit the scope of the claims provided herein.

Example 1. Application of PKC Activator for Differentiation of Pancreatic Endocrine Cells This example demonstrates the effect of PKC activator on generation of different pancreatic endocrine cells, e.g., pancreatic β, α, δ, or EC cell.

Exemplary differentiation protocols, e.g., Version A and Version B, according to the present disclosure were tested for differentiating human stem cells into mature β cells capable of releasing insulin in response to glucose challenge in vitro.

Both Version A and Version B protocols are 6-stage stepwise protocols that share similar reagents and treatment timing. With Version A protocols, stem cells were treated with reagents in the following consecutive orders during the first five stages: Stage 1 (S1), Activin-A for 3 days and also CHIR99021 for the first 24 hr; Stage 2 (S2), KGF for 3 days; Stage 3 (S3), KGF, PDBU, Sant-1, retinoic acid (RA), Activin A, and Thiazovivin for 2 days, and also DMH-1 for the first day; Stage 4 (S4), KGF, Sant-1, Thiazovivin, Activin A, and RA for 6 days; Stage 5 (S5), XXI, Alk5i, GC-1, LDN-193189, Thiazovivin, Staurosporine, and DZNEP for 7 days, and also RA, Sant-1, and Betacellulin for the first 2 days. In Version B protocols, one difference from Version A protocols is that the cells were supplemented with PDBU from day 5 of Stage 4 (S4d5) to day 2 of Stage 5 (S5d2). In one experiment, 500 nM of PDBU was used to treat the cells during S4d5 to S5d2.

As illustrated in the schematics of single-cell RNA sequencing results in FIG. 1, upon completion of S5 differentiation, the cells (S5c cells) generated via a Version B protocol and S5c cells generated via a Version A protocol had comparable percentage of cells expressing CHGA (gene encoding chromogranin A; an exemplary marker of pancreatic endocrine cells), and comparable percentage of cells expressing ISL1 (an exemplary marker of pancreatic islet cells). In contrast, S5c cells generated via Version B protocol had much reduced percentage of cells expressing DDC (gene encoding dopa decarboxylase; an exemplary marker of enterochromaffin (EC) cells).

In one experiment, four different exemplary Stage 6 treatment paradigms were also tested at S6 in combination with the first five stages of Version A or Version B protocols. Briefly, i) with S6-a paradigm, S5c cells were cultured in DMEM/F12 medium containing 1% HSA for 7-14 days; ii) with S6-b paradigm, S5c cells were cultured in MCDB131 medium containing 0.05% HSA and the following supplements (per 1 L MCDB131): 0.44 g Glucose, 1.23 g NaHCO3, 0.044 g Vitamin C, 10 ml Glutamax, and 5 ml ITS-x; iii) with S6-c paradigm, S5c cells were cultured in MCDB131 medium containing 0.05% HSA and vitamin C for 7-14 days, during which the cells were treated with 10 µM Alk5i, 1 µM GC-1, 100 nM LDN-193189, 2.5 µM Thiazovivin, 3 nM SSP, and 100 nM DZNEP for the first four days; iv) with S6-d paradigm, S5c cells were cultured in MCDB131 medium (no glutamine base media) containing 0.05% HSA, ITS-X, vitamin C, and 4 mM Gln, as well as 10 µM Alk5i, 1 µM GC-1, 100 nM LDN-193189, 2.5 µM Thiazovivin, 3 nM SSP, and 100 nM DZNEP, for four days, followed by culturing in MCDB131 medium (no glutamine base media) containing 0.05% HSA, ITS-X, vitamin C, and 4 mM Gln with no additional factors for additional 3-10 days.

Figure 2A:
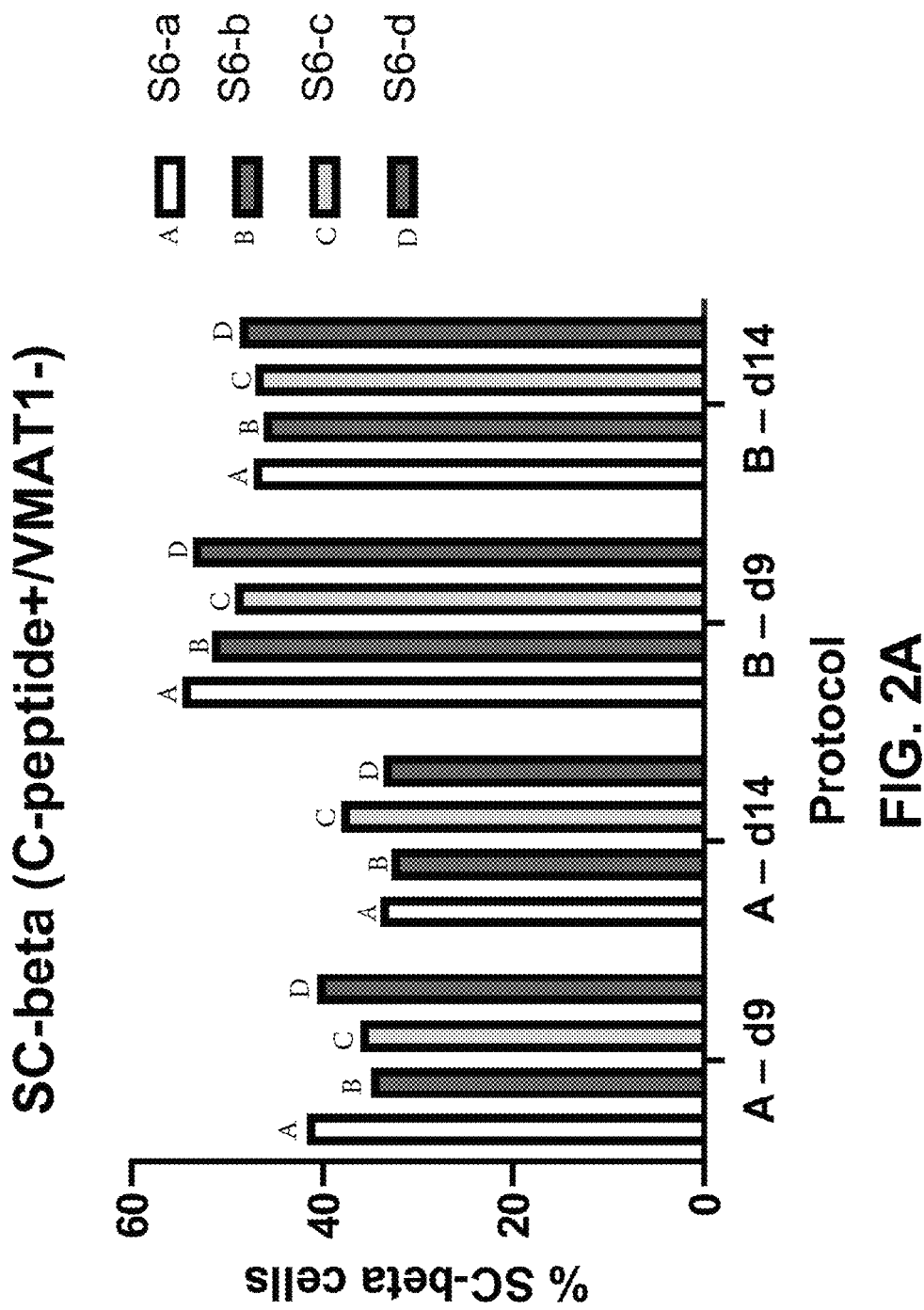
FIGS. 2A-2B summarize the percentage of C-peptide-positive, VMAT1-negative cells (FIG. 2A) in the in vitro endocrine cell populations generated according to two exemplary differentiation protocols, with or without PDBU applied on S4d5 to S5d2, as measured by flow cytometry (FIG. 2B).
Figure 2B:
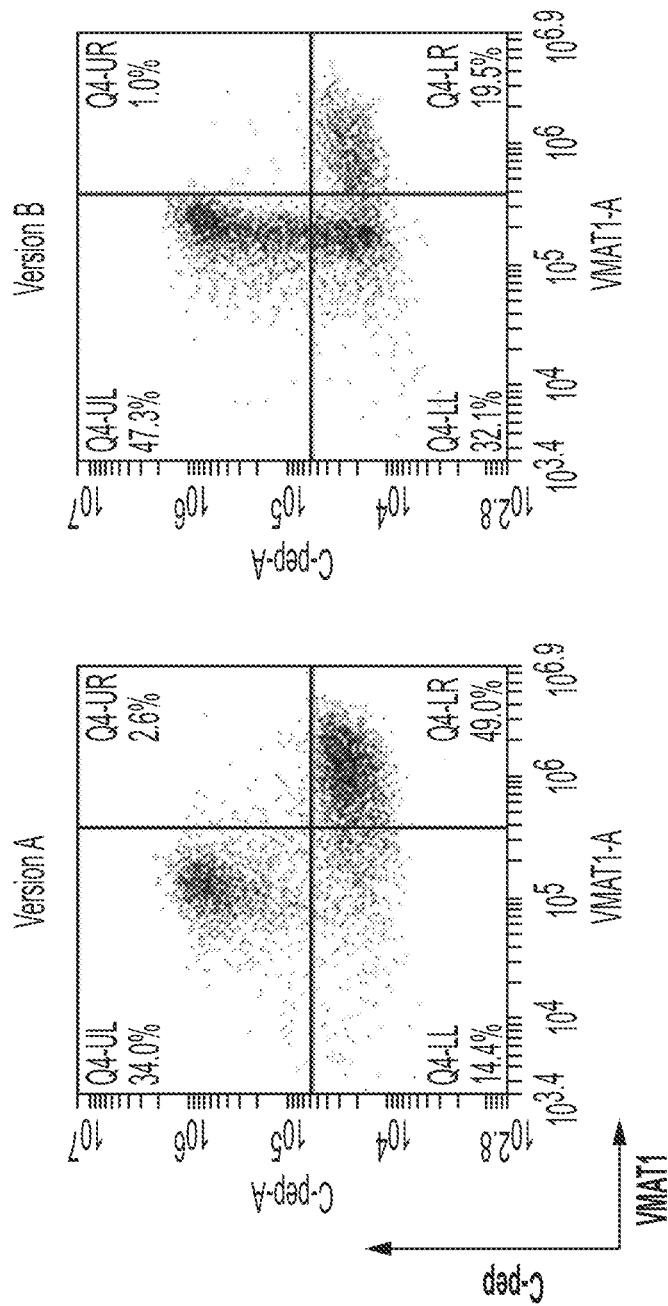

FIG. 2A demonstrates the increase in percentage of cells that express C-peptide and do not express VMAT1 (exemplary characteristic of Sc-β cells) generated by Version B protocols as compared to Version A protocols, as measured by flow cytometry (FIG. 2B). As shown in the figure, with Version A protocols, the percentage of C-peptide-positive, VMAT1-negative cells on S6d9 or S6d14 were all around 35%, except for VA/S6-a and VA/S6-d on S6d9 (both around 40%), whereas with Version B protocols, the percentage of C-peptide-positive, VMAT1-negative cells was from 45% to 55% on S6d9, and around 45% on S6d14.

Figures 3, 4:
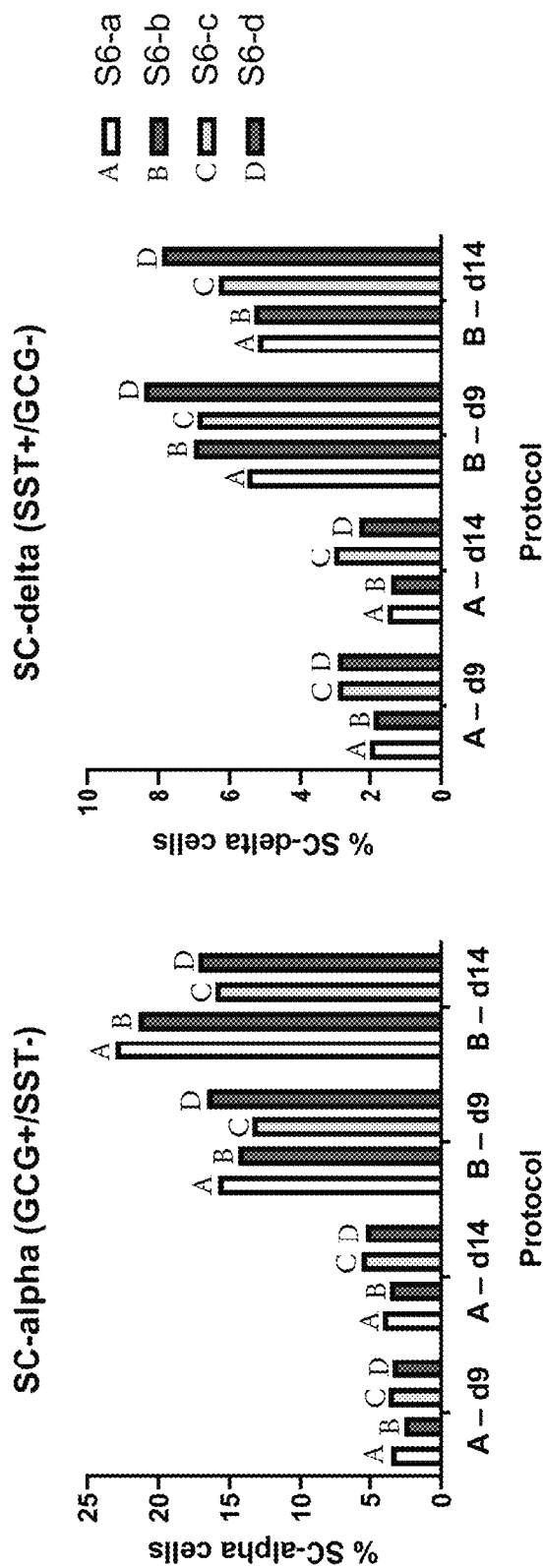
FIG. 3 summarizes the percentage of glucagon-positive, somatostatin-negative cells (GCG+/SST−) in the in vitro endocrine cell populations generated according to two exemplary differentiation protocols, with or without PDBU applied on S4d5 to S5d2.
FIG. 4 summarizes the percentage of somatostatin-positive, glucagon-negative cells (SST+/GCG−) in the in vitro endocrine cell populations generated according to two exemplary differentiation protocols, with or without PDBU applied on S4d5 to S5d2.
Figure 5:
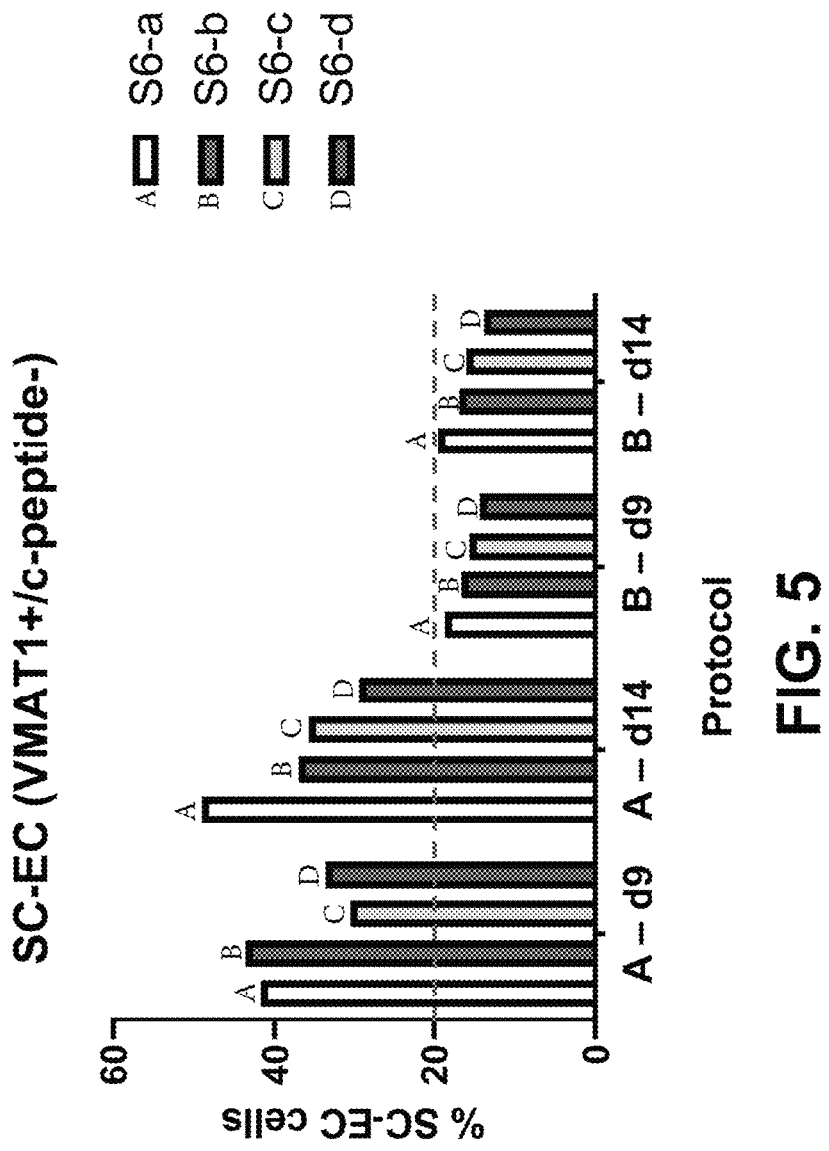
FIG. 5 summarizes the percentage of VMAT1-positive, C-peptide-negative cells (VMAT1+/c-peptide−) in the in vitro endocrine cell populations generated according to two exemplary differentiation protocols, with or without PDBU applied on S4d5 to S5d2.

FIGS. 3-5 demonstrate the changes in percentages of α cells (measured by cells that express glucagon (GCG) but do not express somatostatin (SST) via flow cytometry), δ cells (measured by cells that express SST but do not express GCG via flow cytometry), and EC cells (measured by cells that express VMAT1 but do not express C-peptide via flow cytometry) with Version B protocols as compared to Version A protocols. As shown in FIG. 3, with Version A protocols, the percentage of α cells on S6d9 or S6d14 was all below or around 5%, whereas with Version B protocols, the percentage of α cells was from 12.5% to 17% on S6d9, and around 15% (vB/S6-c and vB/S6-d) or around 22% (vB/S6-a and vB/S6-b) on S6d14. As shown in FIG. 4, with vA protocols, the percentage of δ cells on S6d9 or S6d14 was below or around 2% (vA/S6-a and vA/S6-b) or from 2% to 3% (vA/S6-c and vA/S6-d), whereas with Version B protocols, the percentage of δ cells was around 5% on S6d9 and S6d14 (vB/S6-a), around 7% on S6d9 and around 5% on S6d14 (vB/S6-b), from 6% to 7% on S6d9 and S6d14 (vB/S6-c), or around 8% on S6d9 and S6d14 (vB/S6-d). As shown in FIG. 5, with Version A protocols, the percentage of EC cells on S6d9 or S6d14 was from 40% to 50% (vA/S6-a), from 35% to 45% (vA/S6-b), or from 25% to 35% (vA/S6-c and vA/S6-d), whereas with vB protocols, the percentage of EC cells was all less than 20% on S6d9 and S6d14.

Figures 6A, 6B:
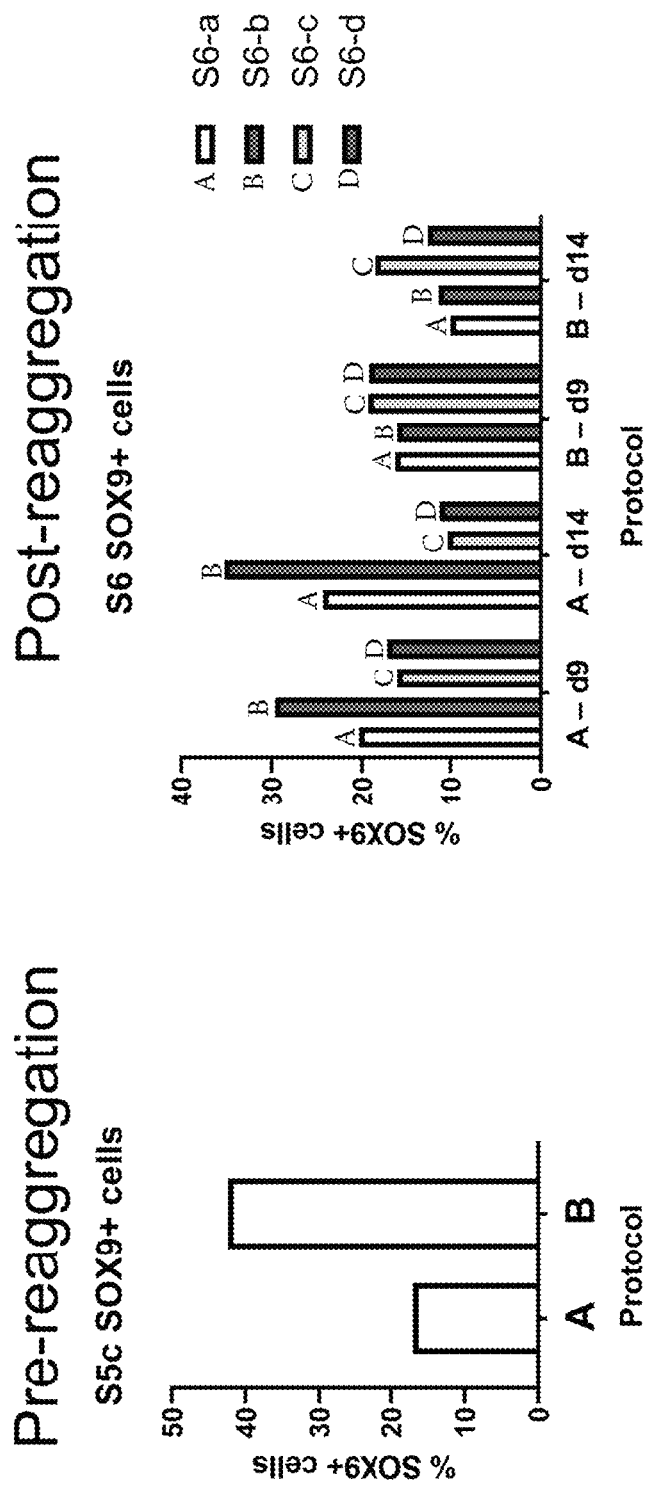
FIGS. 6A-6B summarize the percentage of SOX9-positive cells before (FIG. 6A) and after reaggregation (FIG. 6B) in the in vitro endocrine cell populations generated according to two exemplary differentiation protocols, with or without PDBU applied on S4d5 to S5d2, as measured by flow cytometry.
Figure 7:
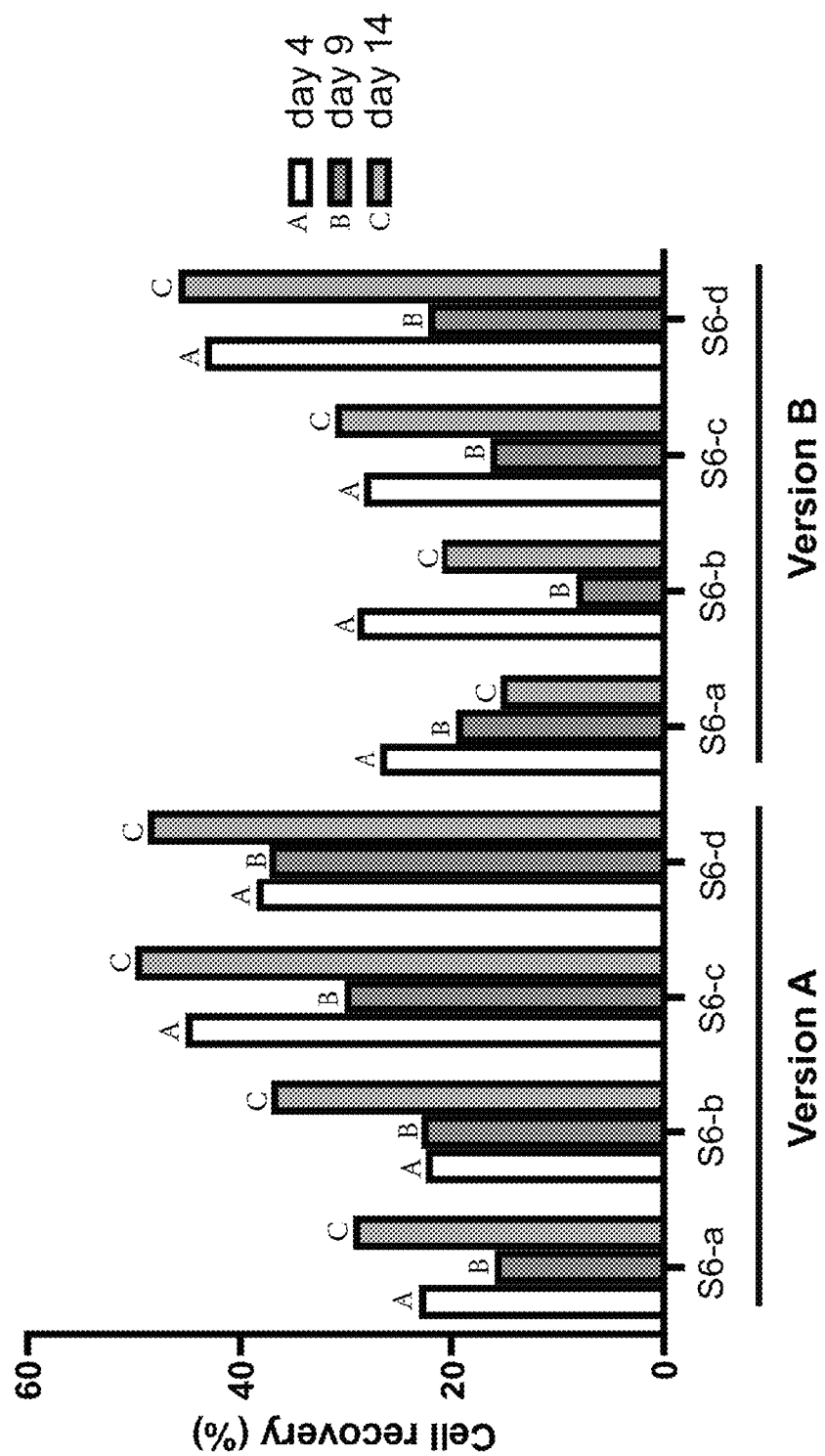
FIG. 7 summarizes the recovery ratio after reaggregation in the in vitro endocrine cell populations generated according to two exemplary differentiation protocols, with or without PDBU applied on S4d5 to S5d2.

In one experiment, SOX9 expression was compared between Version A and Version B protocols, and it was found that at the end of S5, there were increased cells expressing SOX9 with Version B protocols as compared to Version A protocols (FIG. 6A). In another experiment, a reaggregation step was introduced between the end of S5 and the beginning of S6. Briefly, S5c cell clusters were collected and dissociated into cell suspension with an enzyme and then cultured in S6 culture media to reaggregate into new cell clusters. FIG. 6B summarizes the percentage of cells expressing SOX9 during S6 after the reaggregation step with different differentiation protocols. In another experiment, the S6 cell recovery percentage was examined, which measured the ratio of the cell density at a certain time point of S6 (e.g., S6d4, S6d9, or S6d14) relative to the initial seed density at the beginning of S6 (after dissociation of S5c cells, e.g., 2 million/ml). As shown in FIG. 7, Version B protocols had similar S6 cell recovery percentage as compared to Version A protocols.

Figure 8:
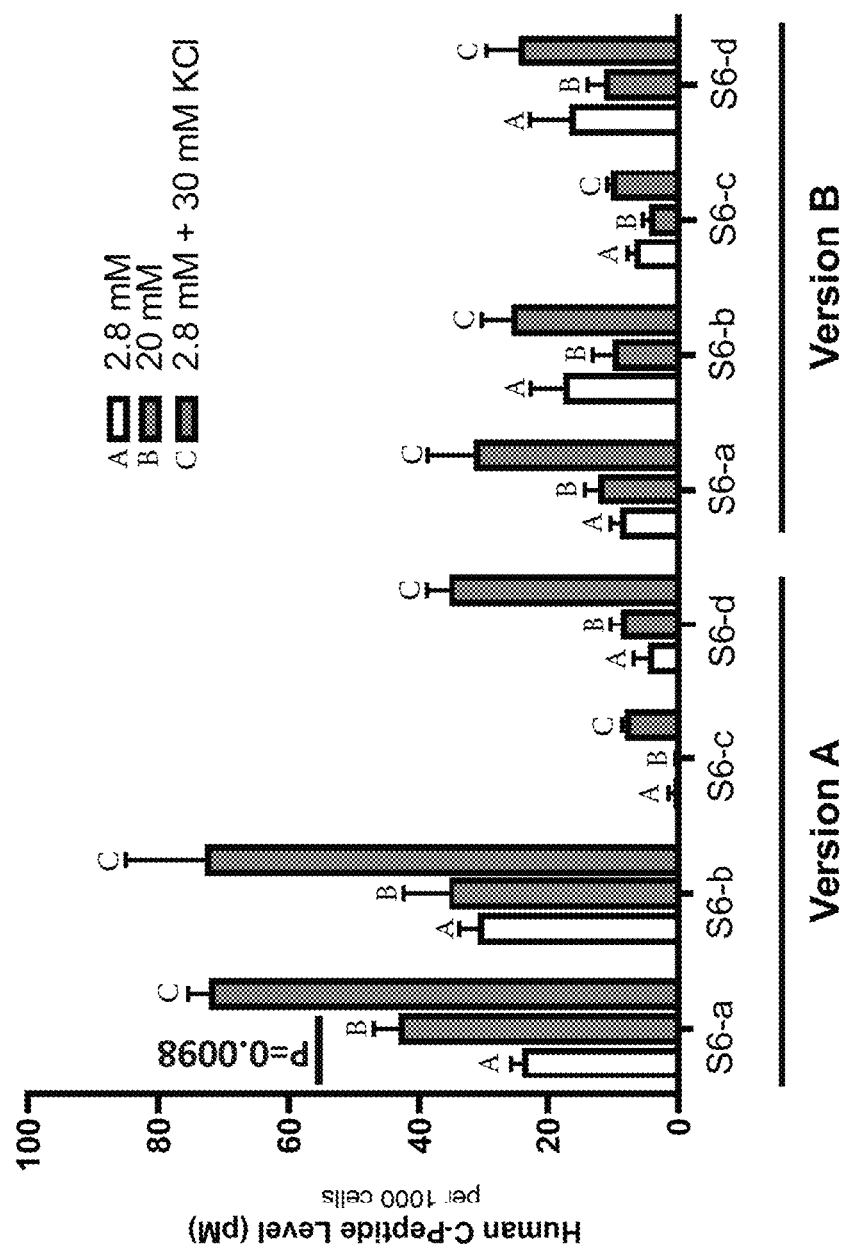
FIG. 8 summarizes glucose-stimulated insulin secretion (GSIS) response of the in vitro endocrine cell populations generated according to two exemplary differentiation protocols, with or without PDBU applied on S4d5 to S5d2.
Figure 9:
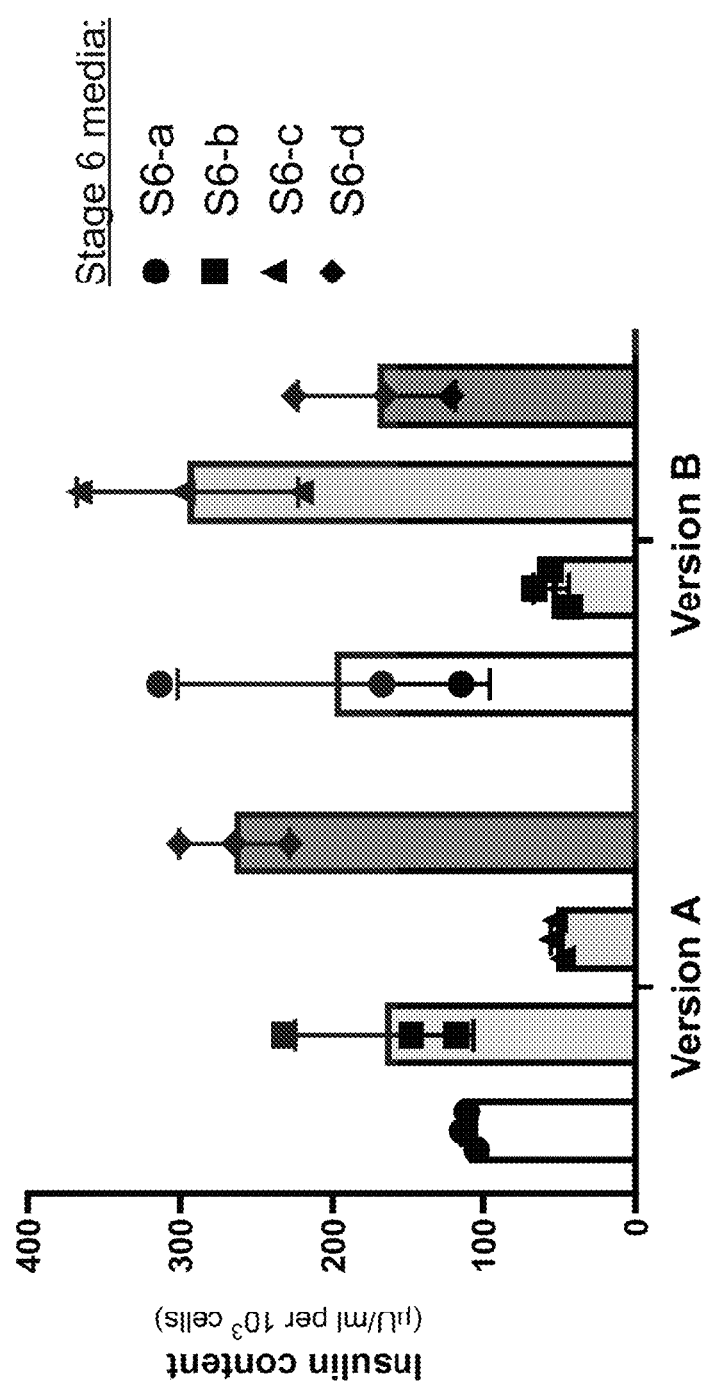
FIG. 9 summarizes the insulin content of the in vitro endocrine cell populations generated according to two exemplary differentiation protocols, with or without PDBU applied on S4d5 to S5d2.

In one experiment, in vitro glucose-stimulated insulin secretion response of S6d13 cells generated by Version A and Version B protocols was examined. As shown in FIG. 8, the cells generated with Version B protocols showed relatively low responsiveness to glucose challenges, and there was no clear increase in insulin secretion in response to 20 mM glucose challenge as compared to 2.8 mM glucose challenge. In contrast, cells generated with vA/S6-a protocol demonstrated sharp increase in insulin secretion in response to 20 mM as compared to 2.8 mM glucose challenge. On the other hand, insulin content in cells generated with Version B protocols was comparable with cells generated with Version B protocols (FIG. 9).

Figure 10A:
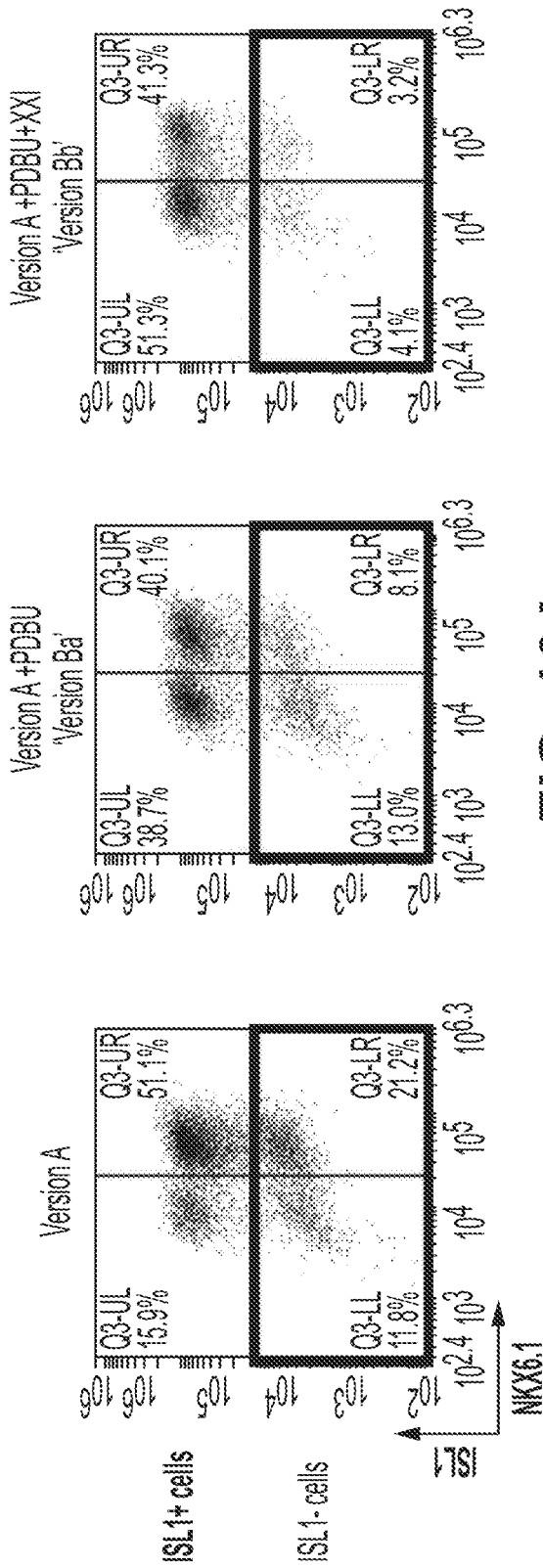
FIGS. 10A-10B summarize the percentage of NKX6.1-positive, ISL1-positive cells (FIG. 10B) in the in vitro cell populations generated according to three exemplary differentiation protocols, with or without PDBU or PDBU and XXI applied during S4d5 to S5d2, as measured by flow cytometry (FIG. 10A).
Figure 10B:
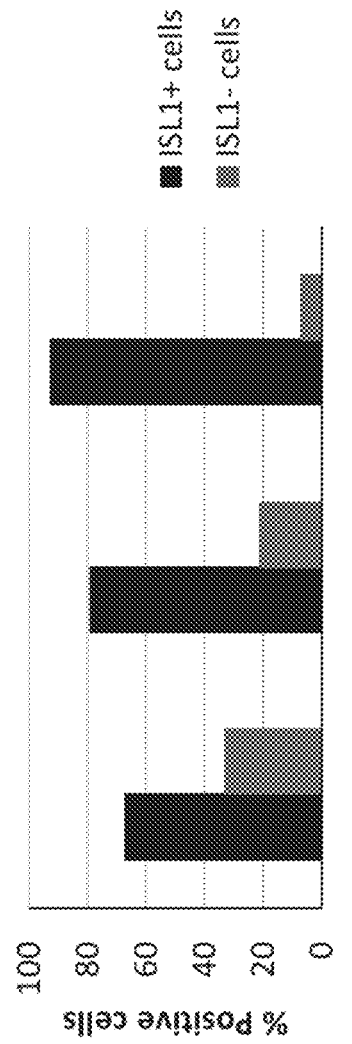

In one experiment, effect of application of PDBU and gamma secretase inhibitor, XXI, was tested. In this experiment, three differentiation conditions were examined and compared: Version A protocol; Version B; Version B+XXI (both PDBU and XXI was applied from S4d5 to S5d2, and XXI continued to be applied throughout S5). FIG. 10B summarizes the percentages of ISL 1-positive cells and ISL1-negative cells at S5c generated via different protocols, as measured by flow cytometry (exemplified in FIG. 10A). As shown in the figure, combined PKC activation and gamma secretase inhibition starting during S4 led to robust induction of ISL1-positive cells from about 65% to higher than 90%, whereas PKC activation alone led to about 80% ISL1-positive cells.

In another experiment, the effect of two different PKC activators on enterochromaffin cells and alpha cells was examined. In this experiment, three differentiation conditions were examined and compared: Version A protocol; Version A with PDBU applied at 0.5 µM on days S4d5, S5d1, and S5d2 (VA+PDBU); and Version A with ((2S,5S)-(E,E)-8-(5-(4-(Trifluoromethyl)phenyl)-2,4-pentadienoylamino)benzolactam) at 0.1 µM on days S4d5, S5d1, and S5d2 (VA+TPPB). FIG. 11B summarizes the percentages of NKX6.1-positive/ISL-negative cells and ISL1-positive/

Figure 11A:
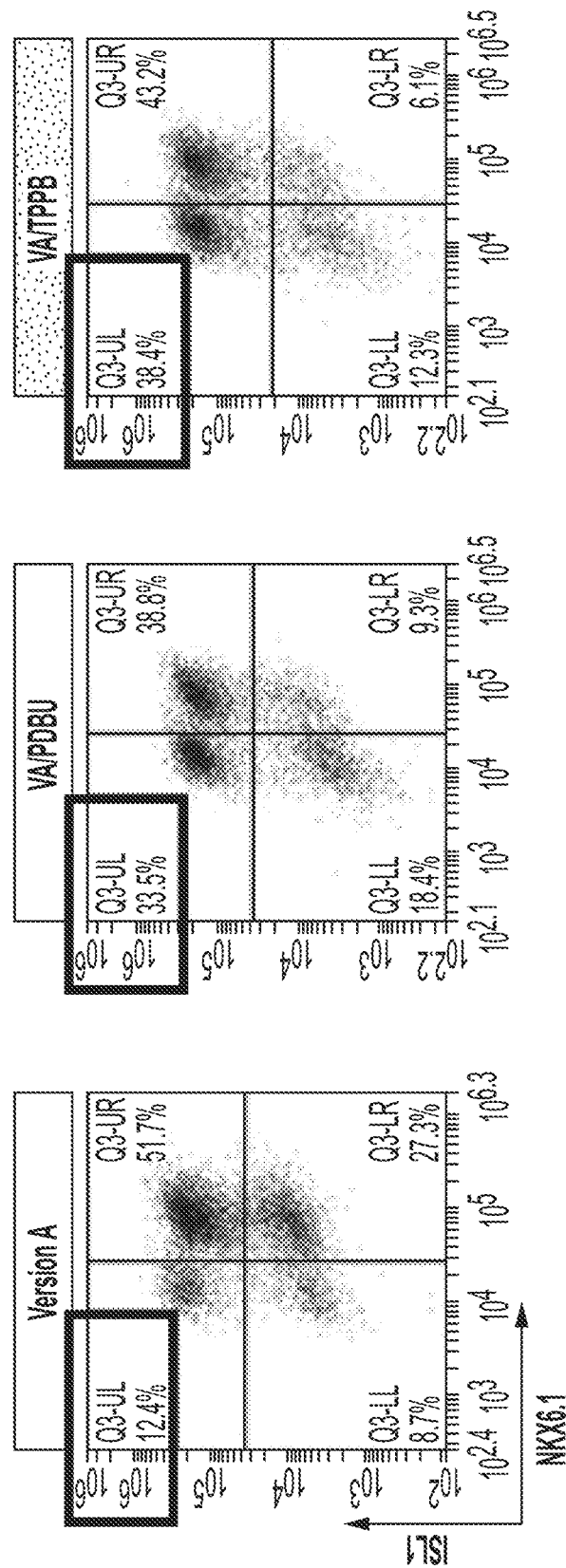
Figure 11B:
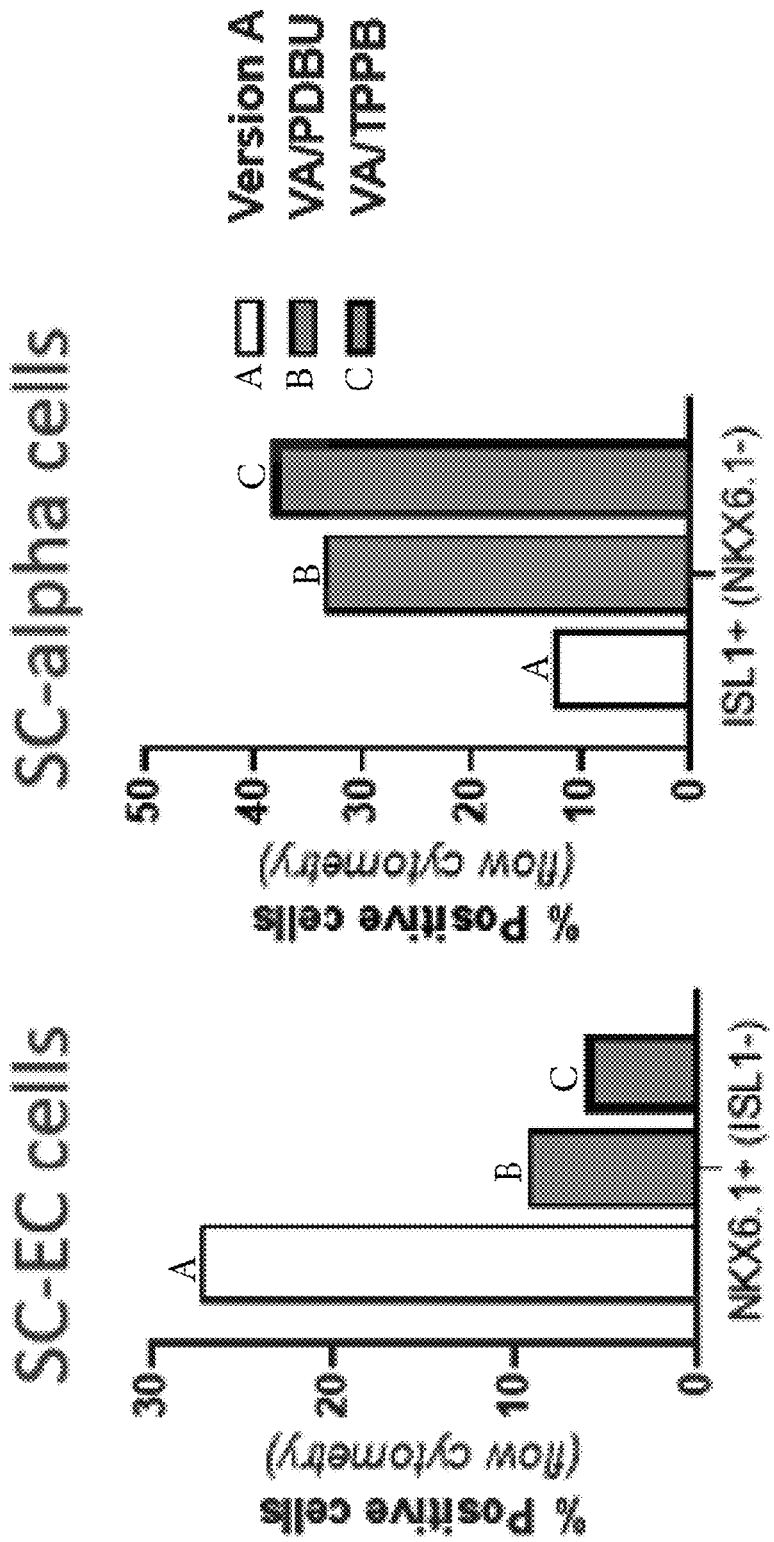

NKX6.1-negative cells at S5c generated via the different protocols, as measured by flow cytometry (exemplified in FIG. 11A). As shown in the figure, VA/TPPB was similarly effective as VA/PDBU at reducing sc-EC cells and increasing alpha cells. However, VA/TPPB surprisingly resulted in a more than 2-fold increase in yield of total cells as compared to VA/PDBU (FIG. 11C). Addition of XXI to VA/TPPB at days S4d5, S5d1, and S5d2 caused a reduction in in cell yield (FIG. 11C).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure can be employed in practicing the present disclosure. It is intended that the following claims define the scope of the present disclosure and that methods and structures within the scope of these claims and their equivalents be covered thereby.

What is claimed is:

1. A population of in vitro differentiated cells comprising NKX6.1-positive, ISL1-positive cells and NKX6.1-negative, ISL1-positive cells; wherein less than 6% of the cells in the population are NKX6.1-negative, ISL1-negative cells; wherein at least 70%, at least 73%, at least 75%, or at least 80% of the cells in the population are ISL1-positive cells; and wherein the population of cells are in one or more cell clusters.

2. The population of claim 1, wherein less than 4% of the cells in the population are NKX6.1-negative, ISL1-negative cells.

3. The population of claim 1, 3 to less than 6% or 3-5% of the cells in the population are NKX6.1-negative, ISL1-negative cells.

4. The population of claim 1, wherein 70-90%, 70-85%, 70-80%, 70-75%, 75-90%, 75-85%, 75-80%, 80-90%, 80-85%, or 85-90% of the cells in the population are ISL1-positive cells.

5. The population of claim 1, wherein at least 4% or at least 5% of the cells in the population are NKX6.1-negative, ISL1-negative cells.

6. The population of claim 1, wherein at least 40% of the cells in the population are NKX6.1-negative, ISL1-positive cells.

7. The population of claim 1, wherein at least 45%, at least 50%, about 40-50%, about 45-55%, or about 50-55% of the cells in the population are NKX6.1-negative, ISL1-positive cells.

8. The population of claim 1, wherein at least 74%, at least 75%, at least 80%, at least 85%, at least 90%, about 85-95%, or about 90-95% of the cells in the population are ISL1-positive cells.

9. The population of claim 1, wherein the population of cells is derived from stem cells in vitro.

10. The population of claim 1, further comprising a medium.

11. The population of claim 10, wherein the medium comprises a sugar.

12. The population of claim 10, wherein the medium comprises the sugar at a concentration of between about 0.05% and about 1.5%.

13. The population of claim 10, wherein the medium is a CMRL medium; or wherein the medium is a cryopreservation media.

14. The population of claim 1, wherein the cell cluster is between about 125 and about 225 microns in diameter, between about 130 and about 160 microns in diameter, between about 170 and about 225 microns in diameter, between about 140 and about 200 microns in diameter, between about 140 and about 170 microns in diameter, between about 160 and about 220 microns in diameter, between about 170 and about 215 microns in diameter, or between about 170 and about 200 microns in diameter.

15. The population of claim 1, wherein the population comprises cells having a genetic disruption in the beta-2-microglobulin gene.

16. The population of claim 1, wherein the population is in an implantable encapsulation device.

17. The population of claim 1, wherein a cluster of the one or more clusters comprises between 500-2500 cells.

18. The population of claim 1, wherein the population comprises NKX6.1-positive, ISL1-positive cells that display a glucose stimulated insulin secretion (GSIS) response similar or superior to that of an endogenous mature β cell if tested in vitro.

19. The population of claim 1, wherein at least about 35% of the cells in the population are C-peptide-positive, VMAT1-negative cells.

20. The population of claim 18, wherein the population comprises NKX6.1-positive, ISL1-positive cells that exhibit a stimulation index of 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 or greater.

21. The population of claim 20, wherein 80-95% of the cells in the population are ISL-positive cells.

* * * * *